(12) United States Patent
Herron-Olson et al.

(10) Patent No.: US 11,318,192 B2
(45) Date of Patent: May 3, 2022

(54) ENGINEERED PROTEINS AND METHODS OF USE

(71) Applicant: Epitopix, LLC, Willmar, MN (US)

(72) Inventors: Lisa Herron-Olson, St. Paul, MN (US); Patricia Tam, St. Paul, MN (US); Drew M. Catron, St. Paul, MN (US); Daryll A. Emery, Willmar, MN (US)

(73) Assignee: Epitopix, LLC, Willmar, MN (US)

( * ) Notice: Subject to any disclaimer, the term of this patent is extended or adjusted under 35 U.S.C. 154(b) by 0 days.

(21) Appl. No.: 16/963,920

(22) PCT Filed: Jan. 25, 2019

(86) PCT No.: PCT/US2019/015164
§ 371 (c)(1),
(2) Date: Jul. 22, 2020

(87) PCT Pub. No.: WO2019/147947
PCT Pub. Date: Aug. 1, 2019

(65) Prior Publication Data
US 2021/0213125 A1 Jul. 15, 2021

Related U.S. Application Data

(60) Provisional application No. 62/621,796, filed on Jan. 25, 2018.

(51) Int. Cl.
*A61K 39/108* (2006.01)
*A61K 39/39* (2006.01)

(52) U.S. Cl.
CPC .......... *A61K 39/0258* (2013.01); *A61K 39/39* (2013.01)

(58) Field of Classification Search
None
See application file for complete search history.

(56) References Cited

U.S. PATENT DOCUMENTS 8,133,496 B2    3/2012  Mobley
2003/0161889 A1* 8/2003  Reid ................... A61K 39/0258
                                                   424/491

FOREIGN PATENT DOCUMENTS

WO    WO 1996/01620 A1   1/1996
WO    WO 2001/37810 A2   5/2001

OTHER PUBLICATIONS

Boulianne et al., "Production of functional chimaeric mouse/human antibody", Dec. 13, 1984, *Nature* 312:643-646.
Bruggemann et al., "Production of human antibody repertoires in transgenic mice", 1997, *Current Opinion in Biotechnology* 8:455-458.
Chen et al., "Fusion Protein Linkers: Property, Design and Functionality," *Advanced Drug Delivery Review*, 65(2013) 1357-1369.
Daugherty et al., "Polymerase chain reaction facilitates the cloning, CDR-grafting, and rapid expression of a murine monoclonal antibody directed against the CD18 component of leukocyte integrins", Mar. 1991, *Nucleic Acids Research*, 19(9):2471-2476.
Jones et al., "Replacing the complementarity-determining regions in a human antibody with those from a mouse", May 1986, *Nature* 321:522-525.
Lonberg et al., "Antigen-specific human antibodies from mice comprising four distinct genetic modifications", Apr. 1994, *Nature* 368:856-859.
Longberg et al., "Human Antibodies from Transgenic Mice", *Immunol.*, 1995; 13(1):65-93.
Lobuglio et al., "Mouse/human chimeric monoclonal antibody in man: Kinetics and immune response", Jun. 1989, *Proc. Natl. Acad. Sci.*, 86:4220-4224.
Mehla et al., "Identification of Epitope-Based Peptide Vaccine Candidates Against Enterotoxigenic *Escherichia coli*: A Comparative Genomics and Immunoinformatics Approach", *Molecular BioSystems*, 206, 12, 890-901, 2016.
Morrison et al., "Chimeric human antibody molecules: Mouse antigen-binding domains with human constant region domains", 1984, *Proc. Natl. Acad. Sci.* 81:6851-6855.
Queen et al., "A humanized antibody that binds to the interleukin 2 receptor", Dec. 1989, *Proc. Natl. Acad. Sci.*, 86:10029-10033.
Riechmann et al., "Reshaping human antibodies for therapy" Mar. 1988, *Nature*, 332:323-327.
Tatusova et al., "BLAST 2 Sequences, a new tool for comparing protein and nucleotide sequences", 1999, *FEMS Microbiology Letters* 174:247-250.
Taylor et al., "A transgenic mouse that expresses a diversity of human sequence heavy and light chain immunoglobulins" 1992, *Nucleic Acids Research*, 20:23):6287-6295.
Van Goor et al., "A Recombinant Multi-Antigen Vaccine with Broad Protection Potential Against Avian Pathogenic *Escherichia coli*", *PLOS One*, vol. 12, No. 8, Aug. 24, 2017, p. E0183929.
Vedrhoeyen et al., "Reshaping Human Antibodies: Grafting an Anti-lysozyme Activity", *Science*, 1988, 239(4847):1534-6.
Wieser et al., "A Multiepitope Subunit Vaccine Conveys Protection Against Extraintestinal Pathogenic *Escherichia coli* in Mice", *Infection and Immunity*, Aug. 2010, 78(8):3432-3442.
Wieser et al., "A Multiepitope Subunit Vaccine Conveys Protection Against Extraintestinal Pathogenic *Escherichia coli* in Mice", *Infection and Immunity*, Aug. 2010, 78(8):3432-3442 Supplemental material, Supplemental file 1, available online [retrieved on May 6, 2021], Retrieved from the Internet: iai.asm.org/content/iai/suppl/2010/07/06/78.8.3432.DC1/Supplemental_figures _IAI00174_10_sent_to_IAI _25_04_2010.pdf, 13 pgs.
International Search Report and Written Opinion for PCT/US2019/015164 dated Aug. 29, 2019 (29 pages).
International Preliminary Report on Patentability for PCT/US0219/015164 dated Jul. 28, 2020 (15 pages).

* cited by examiner

*Primary Examiner* — Brian Gangle
(74) *Attorney, Agent, or Firm* — Mueting Raasch Group

(57) ABSTRACT

Provided herein are proteins that include at least one B cell domain and at least one T cell domain. Also provided are compositions that include one or more of the proteins and methods for using the proteins.

11 Claims, 24 Drawing Sheets

Specification includes a Sequence Listing.

FIGS. 12A-C
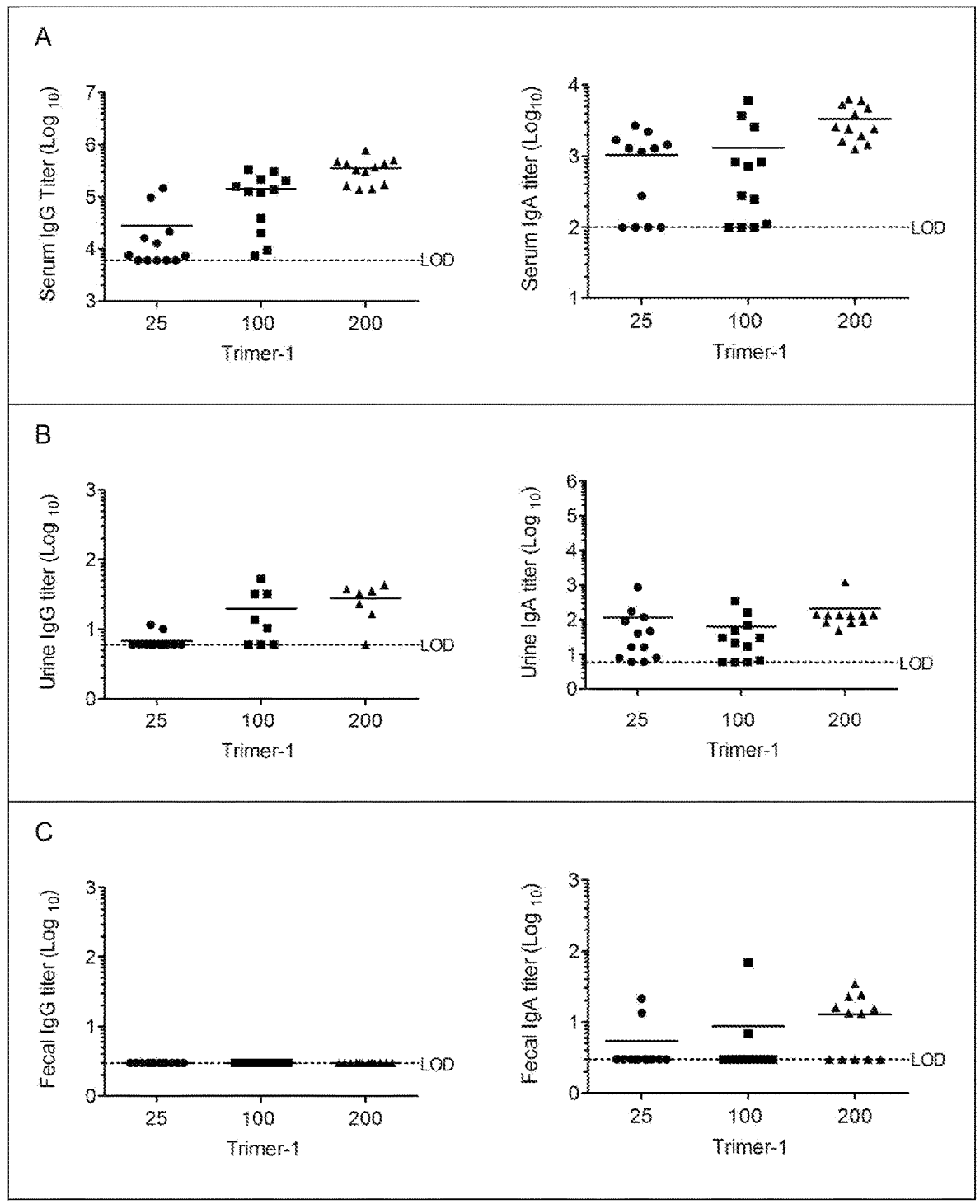

FIGS. 14A-B
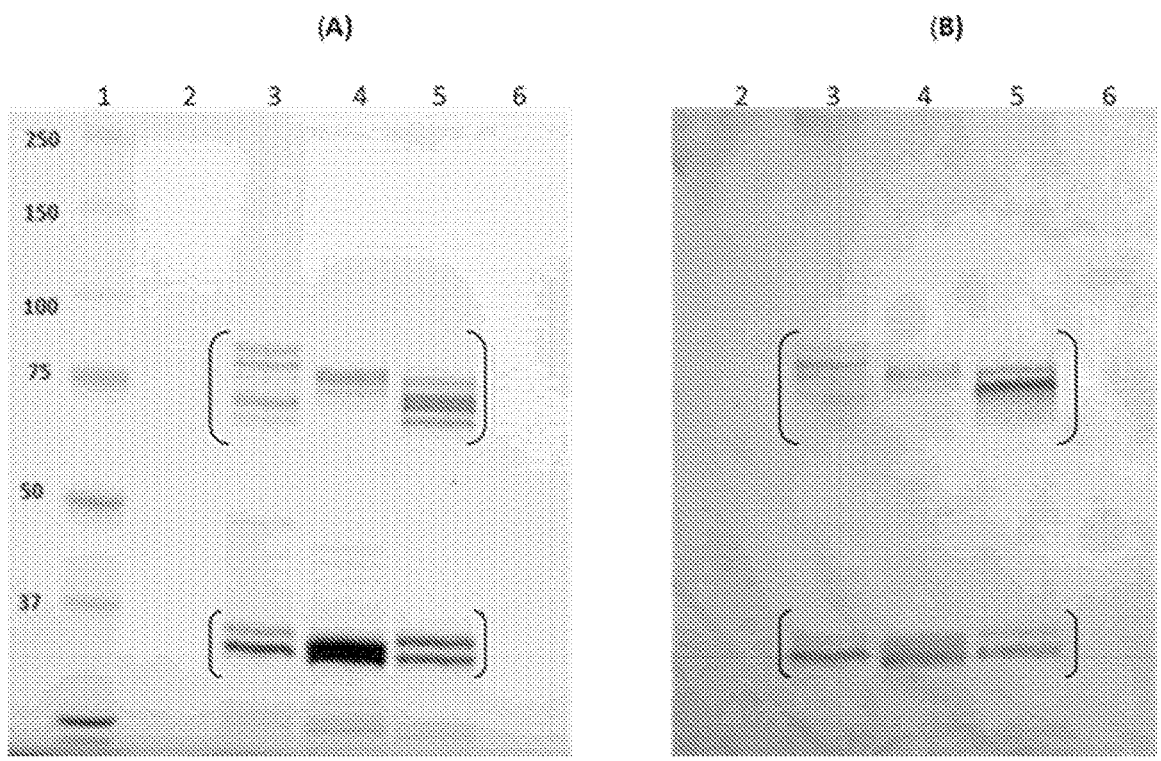

An example of a set of B cell and T cell domains referred to herein as module I, where the B cell and T cell domains are selected from SEQ ID NOs:12-17.

FDRDYTTVWGQRAPLYYSPGYGPASLYDYKGRGESRQLQLITQYYKSQSQGDDNYGLNLGKGFSAISGSSTPYVSKGLN
SDRIPGTERDPFNIDHIEVISGATDESLRFYPFPTVNANKQATAFSSSQQDTDQVAQQNDDNEIIVSAS (SEQ ID NO:1)

An example of a set of B cell and T cell domains referred to herein as module II, where the B cell and T cell domains are selected from SEQ ID NOs:18-22.

REVKSGKKDKYNHWDLNYESRKPGISITGGNEKPDISIKNNQVHTLTPGESLDAWTMRGNLKQPNSKRETHNSRSEKVI
REVKSGKKDKYQEHGKFGNSTT (SEQ ID NO:2)

An example of a module I, where the B cell and T cell domains are selected from SEQ ID NOs:12-17, and where each GSGS is an optional linker.

FDRDYTTVWGQRAPLYYSPGYGPASLYDYKGRGGSGSESRQLQLITQYYKSQGSGSSQGDDNYGLNLGKGFSAISGSST
PYVSKGLNSDRIPGTERGSGSDPFNIDHIEVISGATGSGSDESLRFYPFPTVNANKQATAFSSSQQDTDQGSGSVAQQN
DDNEIIVSAS (SEQ ID NO:3)

An example of a module II, where the B cell and T cell domains are selected from SEQ ID NOs:18-22, and where each GSGS is an optional linker.

REVKSGKKDKYNHWDLNYESRKPGSGSGISITGGNEKPDISIGSGSKNNQVHTLTPGESLDAWTMRGNLKQPNSKRET
HNSRSGSGSEKVIREVKSGKKDKYGSGSQEHGKFGNSTT (SEQ ID NO:4)

An example of a MoLE protein having three tandem repeats of module I, where each GSGS is an optional linker.

FDRDYTTVWGQRAPLYYSPGYGPASLYDYKGRGGSGSESRQLQLITQYYKSQGSGSSQGDDNYGLNLGKGFSAISGSST
PYVSKGLNSDRIPGTERGSGSDPFNIDHIEVISGATGSGSDESLRFYPFPTVNANKQATAFSSSQQDTDQGSGSVAQQN
DDNEIIVSASGSGSFDRDYTTVWGQRAPLYYSPGYGPASLYDYKGRGGSGSESRQLQLITQYYKSQGSGSSQGDDNYGL
NLGKGFSAISGSSTPYVSKGLNSDRIPGTERGSGSDPFNIDHIEVISGATGSGSDESLRFYPFPTVNANKQATAFSSSQQD

FIG. 24 (CONT.)

TDQGSGSVAQQNDDNEIIVSASGSGSFDRDYTTVWGQRAPLYYSPGYGPASLYDYKGRGGSGSESRQLQLITQYYKSQ
GSGSSQGDDNYGLNLGKGFSAISGSSTPYVSKGLNSDRIPGTERGSGSDPFNIDHIEVISGATGSGSDESLRFYPFPTVNA
NKQATAFSSSQQDTDQGSGSVAQQNDDNEIIVSAS (SEQ ID NO:5)

An example of a MoLE protein having three tandem repeats of module II, where each GSGS is an optional linker.

REVKSGKKDKYNHWDLNYESRKPGSGSGISITGGNEKPDISIGSGSKNNQVHTLTPGESLDAWTMRGNLKQPNSKRET
HNSRSGSGSEKVIREVKSGKKDKYGSGSQEHGKFGNSTTGSGSREVKSGKKDKYNHWDLNYESRKPGSGSGISITGGNE
KPDISIGSGSKNNQVHTLTPGESLDAWTMRGNLKQPNSKRETHNSRSGSGSEKVIREVKSGKKDKYGSGSQEHGKFGN
STTGSGSREVKSGKKDKYNHWDLNYESRKPGSGSGISITGGNEKPDISIGSGSKNNQVHTLTPGESLDAWTMRGNLKQ
PNSKRETHNSRSGSGSEKVIREVKSGKKDKYGSGSQEHGKFGNSTT (SEQ ID NO:6)

Nucleotide sequence (SEQ ID NO:7) encoding the MoLE protein of SEQ ID NO:8.
CATCATCACCATCACCATTTCGATCGTGATTATACCACCGTTTGGGGTCAGCGTGCACCGCTGTATTATAGTCCGGG
TTATGGTCCGGCAAGCCTGTATGATTATAAAGGTCGTGGTGGTAGCGGTAGCGAAAGCCGTCAGCTGCAACTGAT
TACCCAGTATTACAAAAGCCAGGGTAGCGGCAGCAGCCAGGGTGATGATAATTATGGTCTGAATCTGGGTAAAG
GCTTTAGCGCAATTAGCGGTAGTAGCACCCCGTATGTTAGCAAAGGTCTGAATAGTGATCGTATTCCGGGTACAG
AACGTGGTTCAGGTAGCGATCCGTTTAACATTGATCATATTGAAGTTATTAGCGGTGCAACCGGTAGCGGTTCAGA
TGAAAGCCTGCGTTTTTATCCGTTTCCGACCGTTAATGCAAATAAACAGGCAACCGCATTTAGCAGCAGTCAGCAG
GATACCGATCAGGGTAGTGGTAGCGTTGCACAGCAGAATGATGATAACGAAATTATTGTTAGCGCAAGCGGCAG
CGGTAGCTTTGATCGCGATTACACAACAGTGTGGGGACAACGTGCCCCTCTGTACTATTCACCTGGTTATGGCCCT
GCATCACTGTATGACTACAAAGGACGCGGAGGTTCAGGTTCAGAAAGTCGTCAACTGCAGCTGATCACACAATAC
TATAAAAGTCAGGGTTCTGGTAGCTCACAGGGCGACGATAACTACGGCCTGAACCTGGGCAAAGGTTTTTCTGCA
ATTAGTGGTTCAAGTACACCGTATGTGTCAAAAGGCCTGAACTCAGATCGCATTCCTGGCACCGAACGCGGTAGT
GGCAGTGATCCGTTCAATATCGACCATATCGAAGTGATTTCAGGTGCCACCGGTTCAGGCAGTGATGAGAGTCTG
CGCTTCTATCCTTTTCCTACAGTGAACGCCAACAAACAGGCCACAGCCTTTAGCTCAAGCCAGCAGGACACAGACC
AGGGTTCAGGCTCAGTGGCCCAGCAGAACGACGATAATGAGATCATTGTGAGCGCCTCAGGCAGCGGTTCTTTTG
ACCGCGACTATACGACGGTATGGGGTCAACGCGCTCCACTGTATTACAGCCCTGGCTACGGTCCTGCCAGTCTGTA
CGATTACAAAGGCCGTGGCGGAAGTGGTAGTGAATCACGCCAACTGCAACTGATCACGCAGTACTACAAATCACA
GGGCTCAGGTAGTAGTCAGGGTGACGACAACTATGGCCTGAATCTGGGGAAAGGATTCTCTGCCATTTCAGGCAG
CTCAACGCCGTATGTGAGTAAAGGACTGAACAGCGACCGCATTCCGGGAACCGAGCGTGGCAGTGGTTCAGACC
CTTTCAACATCGATCACATTGAGGTGATCTCTGGTGCGACCGGCTCTGGCTCAGATGAATCACTGCGCTTTTACCCA
TTCCCGACAGTAAATGCGAACAAACAAGCGACCGCCTTTTCAAGCTCACAGCAAGATACAGATCAAGGCTCTGGTT
CTGTAGCCCAACAAAATGATGACAATGAAATCATCGTTTCCGCCAGCTAA (SEQ ID NO:7)

FIG. 24 (CONT.)

An example of a MoLE protein (SEQ ID NO:8) having three tandem repeats of module I and a 6x His tag, where the linker is GSGS (SEQ ID NO:23).

HHHHHHFDRDYTTVWGQRAPLYYSPGYGPASLYDYKGRGGSGSESRQLQLITQYYKSQGSGSSQGDDNYGLNLGKGF
SAISGSSTPYVSKGLNSDRIPGTERGSGSDPFNIDHIEVISGATGSGSDESLRFYPFPTVNANKQATAFSSSQQDTDQGSG
SVAQQNDDNEIIVSASGSGSFDRDYTTVWGQRAPLYYSPGYGPASLYDYKGRGGSGSESRQLQLITQYYKSQGSGSSQ
GDDNYGLNLGKGFSAISGSSTPYVSKGLNSDRIPGTERGSGSDPFNIDHIEVISGATGSGSDESLRFYPFPTVNANKQATA
FSSSQQDTDQGSGSVAQQNDDNEIIVSASGSGSFDRDYTTVWGQRAPLYYSPGYGPASLYDYKGRGGSGSESRQLQLI
TQYYKSQGSGSSQGDDNYGLNLGKGFSAISGSSTPYVSKGLNSDRIPGTERGSGSDPFNIDHIEVISGATGSGSDESLRFY
PFPTVNANKQATAFSSSQQDTDQGSGSVAQQNDDNEIIVSAS (SEQ ID NO:8)

Nucleotide sequence (SEQ ID NO:9) encoding the MoLE protein of SEQ ID NO:10.
CACCACCACCACCACCACCGTGAAGTTAAAAGCGGCAAAAAGATAAATACAACCACTGGGATCTGAACTATGAA
AGCCGTAAACCGGGTAGCGGTAGTGGTATTAGCATTACCGGTGGTAATGAAAAACCGGATATTAGTATTGGTAGC
GGCAGCAAAAATAACCAGGTTCATACCCTGACACCGGGTGAAAGCCTGGATGCATGGACCATGCGTGGTAATCTG
AAACAGCCGAATAGCAAACGTGAAACCCATAATAGCCGTAGCGGTTCAGGTAGCGAAAAAGTTATTCGTGAAGTG
AAATCGGGTAAAAAAGACAAATATGGCAGCGGTAGCCAAGAACATGGTAAATTTGGTAATAGCACCACCGGTTCT
GGTAGTCGCGAAGTGAAAAGTGGAAAAAAAGACAAATATAACCATTGGGACCTGAATTACGAATCACGCAAACC
GGGTTCAGGTTCAGGCATTTCAATTACAGGTGGCAACGAGAAACCAGATATCAGCATTGGCTCTGGTAGCAAAAA
CAATCAGGTGCACACACTGACCCCTGGTGAATCACTGGACGCCTGGACAATGCGTGGCAACCTGAAACAACCTAA
TTCAAAACGCGAAACGCATAACTCACGTAGTGGTTCTGGTTCAGAAAAAGTGATCCGCGAGGTTAAATCAGGGAA
AAAAGATAAATATGGGTCCGGCTCACAAGAACACGGCAAATTCGGCAATTCAACCACCGGCAGTGGTTCACGTGA
GGTGAAATCTGGCAAAAAAGACAAATACAATCATTGGGACCTGAACTATGAGTCTCGTAAACCTGGTTCTGGCAG
CGGCATTAGTATTACAGGCGGAAACGAAAAACCTGACATTTCTATTGGTTCCGGCTCAAAAAACAACCAAGTACAT
ACGCTGACCCCAGGCGAGAGTCTGGATGCGTGGACGATGCGTGGAAACCTGAAACAGCCAAACTCTAAACGTGA
GACACATAACAGTCGCAGCGGCAGCGGCTCTGAGAAAGTAATTCGGGAAGTAAAATCCGGAAAAAAGATAAAT
ACGGTTCGGGCAGCCAAGAGCACGGAAAATTTGGCAACAGTACCACCTAA (SEQ ID NO:9)

An example of a MoLE protein (SEQ ID NO:10) having three tandem repeats of module II and a 6x His tag, where the linker is GSGS (SEQ ID NO:23).
HHHHHHREVKSGKKDKYNHWDLNYESRKPGSGSGISITGGNEKPDISIGSGSKNNQVHTLTPGESLDAWTMRGNLKQ
PNSKRETHNSRSGSGSEKVIREVKSGKKDKYGSGSQEHGKFGNSTTGSGSREVKSGKKDKYNHWDLNYESRKPGSGSGI
SITGGNEKPDISIGSGSKNNQVHTLTPGESLDAWTMRGNLKQPNSKRETHNSRSGSGSEKVIREVKSGKKDKYGSGSQE

FIG. 24 (CONT.)

HGKFGNSTTGSGSREVKSGKKDKYNHWDLNYESRKPGSGSGISITGGNEKPDISIGSGSKNNQVHTLTPGESLDAWTM
RGNLKQPNSKRETHNSRSGSGSEKVIREVKSGKKDKYGSGSQEHGKFGNSTT (SEQ ID NO:10)

Nucleotide sequence (SEQ ID NO:25) encoding the MoLE protein of SEQ ID NO:26

CATCATCACCATCACCATCGTGAAGTTAAAAGCGGCAAAAAAGATAAATACAACCACTGGGATCTGAACTATGAA
AGCCGTAAACCGGGTAGCGGTAGCGAAAGCCGTCAGCTGCAACTGATTACCCAGTATTACAAAAGCCAGGGTAGC
GGCAGCAAAAATAACCAGGTTCATACCCTGACACCGGGTGAAAGCCTGGATGCATGGACCATGCGTGGTAATCTG
AAACAGCCGAATAGCAAACGTGAAACCCATAATAGCCGTAGCGGTTCAGGTAGCGATCCGTTTAACATTGATCAT
ATTGAAGTTATTAGCGGTGCAACCGGTAGCGGTTCACAAGAACATGGTAAATTTGGTAATAGCACCACCGGTAGT
GGTAGCGTTGCACAGCAGAATGATGATAACGAAATTATTGTTAGCGCAAGCGGCAGCGGTAGCCGCGAAGTGAA
AAGTGGAAAAAAAGACAAATATAACCATTGGGACCTGAATTACGAATACGCAAACCGGGTTCAGGTTCAGAAAG
TCGTCAACTGCAGCTGATCACACAATACTATAAAGTCAGGGTTCTGGTAGCAAAAACAATCAGGTGCACACACTG
ACCCCTGGTGAATCACTGGACGCCTGGACAATGCGTGGCAACCTGAAACAACCTAATTCAAAACGCGAAACGCAT
AACTCACGTAGTGGTAGTGGCAGTGATCCGTTCAATATCGACCATATCGAAGTGATTTCAGGTGCCACCGGTTCAG
GCAGTCAAGAACACGGCAAATTCGGCAATTCAACCACCGGTTCAGGCTCAGTGGCCCAGCAGAACGACGATAATG
AGATCATTGTGAGCGCCTCAGGCAGCGGTTCTCGTGAGGTGAAATCTGGCAAAAAGACAAATACAATCATTGGG
ACCTGAACTATGAGTCTCGTAAACCTGGAAGTGGTAGTGAATCACGCCAACTGCAACTGATCACGCAGTACTACAA
ATCACAGGGCTCAGGTAGTAAAAACAACCAAGTACATACGCTGACCCCAGGCGAGAGTCTGGATGCGTGGACGA
TGCGTGGAAACCTGAAACAGCCAAACTCTAAACGTGAGACACATAACAGTCGCAGCGGCAGTGGTTCAGACCCTT
TCAACATCGATCACATTGAGGTGATCTCTGGTGCGACCGGCTCTGGCTCACAAGAGCACGGAAAATTTGGCAACA
GTACCACCGGCTCTGGTTCTGTAGCCCAACAAAATGATGACAATGAAATCATCGTTTCCGCCAGCTAA (SEQ ID
NO:25)

An example of a MoLE protein (SEQ ID NO:26) where B cell domains are selected from SEQ ID NOs:18-20
and T cell domains are selected from SEQ ID NOs:15-17

HHHHHHREVKSGKKDKYNHWDLNYESRKPGSGSESRQLQLITQYYKSQGSGSKNNQVHTLTPGESLDAWTMRGNLK
QPNSKRETHNSRSGSGSDPFNIDHIEVISGATGSGSQEHGKFGNSTTGSGSVAQQNDDNEIIVSASGSGSREVKSGKKD
KYNHWDLNYESRKPGSGSESRQLQLITQYYKSQGSGSKNNQVHTLTPGESLDAWTMRGNLKQPNSKRETHNSRSGSG
SDPFNIDHIEVISGATGSGSQEHGKFGNSTTGSGSVAQQNDDNEIIVSASGSGSREVKSGKKDKYNHWDLNYESRKPGS
GSESRQLQLITQYYKSQGSGSKNNQVHTLTPGESLDAWTMRGNLKQPNSKRETHNSRSGSGSDPFNIDHIEVISGATGS
GSQEHGKFGNSTTGSGSVAQQNDDNEIIVSAS (SEQ ID NO:26)

Nucleotide sequence (SEQ ID NO:27) encoding the MoLE protein of SEQ ID NO:28

FIG. 24 (CONT.)

CACCACCACCACCACCACCGTGAAGTTAAAAGCGGCAAAAAAGATAAATACAACCACTGGGATCTGAACTATGAA
AGCCGTAAACCGGGTAGCGGTAGTGGTATTAGCATTACCGGTGGTAATGAAAAACCGGATATTAGTATTGGTAGC
GGCAGCAAAAATAACCAGGTTCATACCCTGACACCGGGTGAAAGCCTGGATGCATGGACCATGCGTGGTAATCTG
AAACAGCCGAATAGCAAACGTGAAACCCATAATAGCCGTAGCGGTTCAGGTAGCGAAAAAGTTATTCGTGAAGTG
AAATCGGGTAAAAAAGACAAATATGGCAGCGGTAGCCAAGAACATGGTAAATTTGGTAATAGCACCACCTAA
(SEQ ID NO: 27)

An example of a MoLE protein (SEQ ID NO:28) where B cell domains are selected from SEQ ID NOs:12-14 and T cell domains are selected from SEQ ID NOs:21-22

HHHHHHFDRDYTTVWGQRAPLYYSPGYGPASLYDYKGRGGSGSGISITGGNEKPDISIGSGSSQGDDNYGLNLGKGFS
AISGSSTPYVSKGLNSDRIPGTERGSGSEKVIREVKSGKKDKYGSGSDESLRFYPFPTVNANKQATAFSSSQQDTDQGSG
SFDRDYTTVWGQRAPLYYSPGYGPASLYDYKGRGGSGSGISITGGNEKPDISIGSGSSQGDDNYGLNLGKGFSAISGSST
PYVSKGLNSDRIPGTERGSGSEKVIREVKSGKKDKYGSGSDESLRFYPFPTVNANKQATAFSSSQQDTDQGSGSFDRDYT
TVWGQRAPLYYSPGYGPASLYDYKGRGGSGSGISITGGNEKPDISIGSGSSQGDDNYGLNLGKGFSAISGSSTPYVSKGL
NSDRIPGTERGSGSEKVIREVKSGKKDKYGSGSDESLRFYPFPTVNANKQATAFSSSQQDTDQ (SEQ ID NO:28)

Nucleotide sequence (SEQ ID NO:29) encoding the MoLE protein of SEQ ID NO:30

CACCACCACCACCACCACCGTGAAGTTAAAAGCGGCAAAAAAGATAAATACAACCACTGGGATCTGAACTATGAA
AGCCGTAAACCGGGTAGCGGTAGTGGTATTAGCATTACCGGTGGTAATGAAAAACCGGATATTAGTATTGGTAGC
GGCAGCAAAAATAACCAGGTTCATACCCTGACACCGGGTGAAAGCCTGGATGCATGGACCATGCGTGGTAATCTG
AAACAGCCGAATAGCAAACGTGAAACCCATAATAGCCGTAGCGGTTCAGGTAGCGAAAAAGTTATTCGTGAAGTG
AAATCGGGTAAAAAAGACAAATATGGCAGCGGTAGCCAAGAACATGGTAAATTTGGTAATAGCACCACCTAA
(SEQ ID NO:29)

An example of a MoLE protein (SEQ ID NO:30) having one copy of module II (SEQ ID NO:4) and a 6x His tag, where the linker is GSGS (SEQ ID NO:23)

HHHHHHREVKSGKKDKYNHWDLNYESRKPGSGSGISITGGNEKPDISIGSGSKNNQVHTLTPGESLDAWTMRGNLKQ
PNSKRETHNSRSGSGSEKVIREVKSGKKDKYGSGSQEHGKFGNSTT (SEQ ID NO:30)

SEQUENCE LISTING

<160> NUMBER OF SEQ ID NOS: 30

<210> SEQ ID NO 1
<211> LENGTH: 148
<212> TYPE: PRT
<213> ORGANISM: Artificial
<220> FEATURE:
<223> OTHER INFORMATION: MoLE Protein

<400> SEQUENCE: 1

Phe Asp Arg Asp Tyr Thr Thr Val Trp Gly Gln Arg Ala Pro Leu Tyr
1               5                   10                  15

Tyr Ser Pro Gly Tyr Gly Pro Ala Ser Leu Tyr Asp Tyr Lys Gly Arg
                20                  25                  30

Gly Glu Ser Arg Gln Leu Gln Leu Ile Thr Gln Tyr Tyr Lys Ser Gln
            35                  40                  45

Ser Gln Gly Asp Asp Asn Tyr Gly Leu Asn Leu Gly Lys Gly Phe Ser
    50                  55                  60

Ala Ile Ser Gly Ser Ser Thr Pro Tyr Val Ser Lys Gly Leu Asn Ser
65                  70                  75                  80

Asp Arg Ile Pro Gly Thr Glu Arg Asp Pro Phe Asn Ile Asp His Ile
                85                  90                  95

Glu Val Ile Ser Gly Ala Thr Asp Glu Ser Leu Arg Phe Tyr Pro Phe
            100                 105                 110

Pro Thr Val Asn Ala Asn Lys Gln Ala Thr Ala Phe Ser Ser Ser Gln
        115                 120                 125

Gln Asp Thr Asp Gln Val Ala Gln Gln Asn Asp Asn Glu Ile Ile
    130                 135                 140

Val Ser Ala Ser
145

<210> SEQ ID NO 2
<211> LENGTH: 101
<212> TYPE: PRT
<213> ORGANISM: Artificial
<220> FEATURE:
<223> OTHER INFORMATION: MoLE Protein

<400> SEQUENCE: 2

Arg Glu Val Lys Ser Gly Lys Lys Asp Lys Tyr Asn His Trp Asp Leu
1               5                   10                  15

Asn Tyr Glu Ser Arg Lys Pro Gly Ile Ser Ile Thr Gly Gly Asn Glu
                20                  25                  30

Lys Pro Asp Ile Ser Ile Lys Asn Asn Gln Val His Thr Leu Thr Pro
            35                  40                  45

Gly Glu Ser Leu Asp Ala Trp Thr Met Arg Gly Asn Leu Lys Gln Pro
    50                  55                  60

Asn Ser Lys Arg Glu Thr His Asn Ser Arg Ser Glu Leu Val Ile Arg
65                  70                  75                  80

Glu Val Lys Ser Gly Lys Lys Asp Lys Tyr Gln Glu His Gly Lys Phe
                85                  90                  95

Gly Asn Ser Thr Thr
            100

<210> SEQ ID NO 3
<211> LENGTH: 168
<212> TYPE: PRT
<213> ORGANISM: Artificial
<220> FEATURE:

<223> OTHER INFORMATION: MoLE Protein

<400> SEQUENCE: 3

Phe Asp Arg Asp Tyr Thr Thr Val Trp Gly Gln Arg Ala Pro Leu Tyr
1               5                   10                  15

Tyr Ser Pro Gly Tyr Gly Pro Ala Ser Leu Tyr Asp Tyr Lys Gly Arg
            20                  25                  30

Gly Gly Ser Gly Ser Glu Ser Arg Gln Leu Gln Leu Ile Thr Gln Tyr
        35                  40                  45

Tyr Lys Ser Gln Gly Ser Gly Ser Ser Gln Gly Asp Asp Asn Tyr Gly
    50                  55                  60

Leu Asn Leu Gly Lys Gly Phe Ser Ala Ile Ser Gly Ser Ser Thr Pro
65                  70                  75                  80

Tyr Val Ser Lys Gly Leu Asn Ser Asp Arg Ile Pro Gly Thr Glu Arg
                85                  90                  95

Gly Ser Gly Ser Asp Pro Phe Asn Ile Asp His Ile Glu Val Ile Ser
            100                 105                 110

Gly Ala Thr Gly Ser Gly Ser Asp Glu Ser Leu Arg Phe Tyr Pro Phe
        115                 120                 125

Pro Thr Val Asn Ala Asn Lys Gln Ala Thr Ala Phe Ser Ser Ser Gln
    130                 135                 140

Gln Asp Thr Asp Gln Gly Ser Gly Ser Val Ala Gln Gln Asn Asp Asp
145                 150                 155                 160

Asn Glu Ile Ile Val Ser Ala Ser
                165

<210> SEQ ID NO 4
<211> LENGTH: 117
<212> TYPE: PRT
<213> ORGANISM: Artificial
<220> FEATURE:
<223> OTHER INFORMATION: MoLE Protein

<400> SEQUENCE: 4

Arg Glu Val Lys Ser Gly Lys Lys Asp Lys Tyr Asn His Trp Asp Leu
1               5                   10                  15

Asn Tyr Glu Ser Arg Lys Pro Gly Ser Gly Ser Gly Ile Ser Ile Thr
            20                  25                  30

Gly Gly Asn Glu Lys Pro Asp Ile Ser Ile Gly Ser Gly Ser Lys Asn
        35                  40                  45

Asn Gln Val His Thr Leu Thr Pro Gly Glu Ser Leu Asp Ala Trp Thr
    50                  55                  60

Met Arg Gly Asn Leu Lys Gln Pro Asn Ser Lys Arg Glu Thr His Asn
65                  70                  75                  80

Ser Arg Ser Gly Ser Gly Ser Glu Lys Val Ile Arg Glu Val Lys Ser
                85                  90                  95

Gly Lys Lys Asp Lys Tyr Gly Ser Gly Ser Gln Glu His Gly Lys Phe
            100                 105                 110

Gly Asn Ser Thr Thr
        115

<210> SEQ ID NO 5
<211> LENGTH: 512
<212> TYPE: PRT
<213> ORGANISM: Artificial
<220> FEATURE:
<223> OTHER INFORMATION: MoLE Protein

<400> SEQUENCE: 5

```
Phe Asp Arg Asp Tyr Thr Thr Val Trp Gly Gln Arg Ala Pro Leu Tyr
1               5                   10                  15

Tyr Ser Pro Gly Tyr Gly Pro Ala Ser Leu Tyr Asp Tyr Lys Gly Arg
            20                  25                  30

Gly Gly Ser Gly Ser Glu Ser Arg Gln Leu Gln Leu Ile Thr Gln Tyr
        35                  40                  45

Tyr Lys Ser Gln Gly Ser Gly Ser Ser Gln Gly Asp Asp Asn Tyr Gly
    50                  55                  60

Leu Asn Leu Gly Lys Gly Phe Ser Ala Ile Ser Gly Ser Ser Thr Pro
65                  70                  75                  80

Tyr Val Ser Lys Gly Leu Asn Ser Asp Arg Ile Pro Gly Thr Glu Arg
                85                  90                  95

Gly Ser Gly Ser Asp Pro Phe Asn Ile Asp His Ile Glu Val Ile Ser
            100                 105                 110

Gly Ala Thr Gly Ser Gly Ser Asp Glu Ser Leu Arg Phe Tyr Pro Phe
        115                 120                 125

Pro Thr Val Asn Ala Asn Lys Gln Ala Thr Ala Phe Ser Ser Ser Gln
    130                 135                 140

Gln Asp Thr Asp Gln Gly Ser Gly Ser Val Ala Gln Gln Asn Asp Asp
145                 150                 155                 160

Asn Glu Ile Ile Val Ser Ala Ser Gly Ser Gly Ser Phe Asp Arg Asp
                165                 170                 175

Tyr Thr Thr Val Trp Gly Gln Arg Ala Pro Leu Tyr Tyr Ser Pro Gly
            180                 185                 190

Tyr Gly Pro Ala Ser Leu Tyr Asp Tyr Lys Gly Arg Gly Gly Ser Gly
        195                 200                 205

Ser Glu Ser Arg Gln Leu Gln Leu Ile Thr Gln Tyr Tyr Lys Ser Gln
    210                 215                 220

Gly Ser Gly Ser Ser Gln Gly Asp Asp Asn Tyr Gly Leu Asn Leu Gly
225                 230                 235                 240

Lys Gly Phe Ser Ala Ile Ser Gly Ser Ser Thr Pro Tyr Val Ser Lys
                245                 250                 255

Gly Leu Asn Ser Asp Arg Ile Pro Gly Thr Glu Arg Gly Ser Gly Ser
            260                 265                 270

Asp Pro Phe Asn Ile Asp His Ile Glu Val Ile Ser Gly Ala Thr Gly
        275                 280                 285

Ser Gly Ser Asp Glu Ser Leu Arg Phe Tyr Pro Phe Pro Thr Val Asn
    290                 295                 300

Ala Asn Lys Gln Ala Thr Ala Phe Ser Ser Gln Gln Asp Thr Asp
305                 310                 315                 320

Gln Gly Ser Gly Ser Val Ala Gln Gln Asn Asp Asp Asn Glu Ile Ile
                325                 330                 335

Val Ser Ala Ser Gly Ser Gly Ser Phe Asp Arg Asp Tyr Thr Thr Val
            340                 345                 350

Trp Gly Gln Arg Ala Pro Leu Tyr Tyr Ser Pro Gly Tyr Gly Pro Ala
        355                 360                 365

Ser Leu Tyr Asp Tyr Lys Gly Arg Gly Gly Ser Gly Ser Glu Ser Arg
    370                 375                 380

Gln Leu Gln Leu Ile Thr Gln Tyr Tyr Lys Ser Gln Gly Ser Gly Ser
385                 390                 395                 400

Ser Gln Gly Asp Asp Asn Tyr Gly Leu Asn Leu Gly Lys Gly Phe Ser
                405                 410                 415
```

```
Ala Ile Ser Gly Ser Ser Thr Pro Tyr Val Ser Lys Gly Leu Asn Ser
            420                 425                 430

Asp Arg Ile Pro Gly Thr Glu Arg Gly Ser Gly Ser Asp Pro Phe Asn
            435                 440                 445

Ile Asp His Ile Glu Val Ile Ser Gly Ala Thr Gly Ser Gly Ser Asp
            450                 455                 460

Glu Ser Leu Arg Phe Tyr Pro Phe Pro Thr Val Asn Ala Asn Lys Gln
465                 470                 475                 480

Ala Thr Ala Phe Ser Ser Gln Gln Asp Thr Asp Gln Gly Ser Gly
            485                 490                 495

Ser Val Ala Gln Gln Asn Asp Asp Asn Glu Ile Ile Val Ser Ala Ser
            500                 505                 510
```

<210> SEQ ID NO 6
<211> LENGTH: 359
<212> TYPE: PRT
<213> ORGANISM: Artificial
<220> FEATURE:
<223> OTHER INFORMATION: MoLE Protein

<400> SEQUENCE: 6

```
Arg Glu Val Lys Ser Gly Lys Lys Asp Lys Tyr Asn His Trp Asp Leu
1               5                   10                  15

Asn Tyr Glu Ser Arg Lys Pro Gly Ser Gly Ser Gly Ile Ser Ile Thr
                20                  25                  30

Gly Gly Asn Glu Lys Pro Asp Ile Ser Ile Gly Ser Gly Ser Lys Asn
            35                  40                  45

Asn Gln Val His Thr Leu Thr Pro Gly Glu Ser Leu Asp Ala Trp Thr
50                  55                  60

Met Arg Gly Asn Leu Lys Gln Pro Asn Ser Lys Arg Glu Thr His Asn
65                  70                  75                  80

Ser Arg Ser Gly Ser Gly Ser Glu Lys Val Ile Arg Glu Val Lys Ser
                85                  90                  95

Gly Lys Lys Asp Lys Tyr Gly Ser Gly Ser Gln Glu His Gly Lys Phe
            100                 105                 110

Gly Asn Ser Thr Thr Gly Ser Gly Ser Arg Glu Val Lys Ser Gly Lys
            115                 120                 125

Lys Asp Lys Tyr Asn His Trp Asp Leu Asn Tyr Glu Ser Arg Lys Pro
            130                 135                 140

Gly Ser Gly Ser Gly Ile Ser Ile Thr Gly Gly Asn Glu Lys Pro Asp
145                 150                 155                 160

Ile Ser Ile Gly Ser Gly Ser Lys Asn Asn Gln Val His Thr Leu Thr
                165                 170                 175

Pro Gly Glu Ser Leu Asp Ala Trp Thr Met Arg Gly Asn Leu Lys Gln
            180                 185                 190

Pro Asn Ser Lys Arg Glu Thr His Asn Ser Arg Ser Gly Ser Gly Ser
            195                 200                 205

Glu Lys Val Ile Arg Glu Val Lys Ser Gly Lys Lys Asp Lys Tyr Gly
            210                 215                 220

Ser Gly Ser Gln Glu His Gly Lys Phe Gly Asn Ser Thr Thr Gly Ser
225                 230                 235                 240

Gly Ser Arg Glu Val Lys Ser Gly Lys Lys Asp Lys Tyr Asn His Trp
                245                 250                 255

Asp Leu Asn Tyr Glu Ser Arg Lys Pro Gly Ser Gly Ser Gly Ile Ser
            260                 265                 270
```

```
Ile Thr Gly Gly Asn Glu Lys Pro Asp Ile Ser Ile Gly Ser Gly Ser
        275                 280                 285

Lys Asn Asn Gln Val His Thr Leu Thr Pro Gly Glu Ser Leu Asp Ala
    290                 295                 300

Trp Thr Met Arg Gly Asn Leu Lys Gln Pro Asn Ser Lys Arg Glu Thr
305                 310                 315                 320

His Asn Ser Arg Ser Gly Ser Gly Ser Glu Lys Val Ile Arg Glu Val
                325                 330                 335

Lys Ser Gly Lys Lys Asp Lys Tyr Gly Ser Gly Ser Gln Glu His Gly
            340                 345                 350

Lys Phe Gly Asn Ser Thr Thr
        355

<210> SEQ ID NO 7
<211> LENGTH: 1557
<212> TYPE: DNA
<213> ORGANISM: Artificial
<220> FEATURE:
<223> OTHER INFORMATION: Nucleotide sequence encoding a MoLE Protein

<400> SEQUENCE: 7
```

| | | | | | |
|---|---|---|---|---|---|
| catcatcacc | atcaccattt | cgatcgtgat | tataccaccg | tttggggtca | gcgtgcaccg | 60 |
| ctgtattata | gtccgggtta | tggtccggca | agcctgtatg | attataaagg | tcgtggtggt | 120 |
| agcggtagcg | aaagccgtca | gctgcaactg | attacccagt | attacaaaag | ccagggtagc | 180 |
| ggcagcagcc | aggtgatgat | aattatggt | ctgaatctgg | gtaaaggctt | tagcgcaatt | 240 |
| agcggtagta | gcacccccgta | tgttagcaaa | ggtctgaata | gtgatcgtat | tccgggtaca | 300 |
| gaacgtggtt | caggtagcga | tccgtttaac | attgatcata | ttgaagttat | tagcggtgca | 360 |
| accggtagcg | gttcagatga | aagcctgcgt | ttttatccgt | ttccgaccgt | taatgcaaat | 420 |
| aaacaggcaa | ccgcatttag | cagcagtcag | caggataccg | atcagggtag | tggtagcgtt | 480 |
| gcacagcaga | tgatgataa | cgaaattatt | gttagcgcaa | gcggcagcgg | tagctttgat | 540 |
| cgcgattaca | caacagtgtg | gggacaacgt | gcccctctgt | actattcacc | tggttatggc | 600 |
| cctgcatcac | tgtatgacta | caaaggacgc | ggaggttcag | gttcagaaag | tcgtcaactg | 660 |
| cagctgatca | cacaatacta | taaagtcag | ggttctggta | gctcacaggg | cgacgataac | 720 |
| tacggcctga | acctgggcaa | aggtttttct | gcaattagtg | gttcaagtac | accgtatgtg | 780 |
| tcaaaaggcc | tgaactcaga | tcgcattcct | ggcaccgaac | gcggtagtgg | cagtgatccg | 840 |
| ttcaatatcg | accatatcga | agtgatttca | ggtgccaccg | ttcaggcag | tgatgagagt | 900 |
| ctgcgcttct | atccttttcc | tacagtgaac | gccaacaaac | aggccacagc | ctttagctca | 960 |
| agccagcagg | acacagacca | gggttcaggc | tcagtggccc | agcagaacga | cgataatgag | 1020 |
| atcattgtga | gcgcctcagg | cagcggttct | tttgaccgcg | actatacgac | ggtatggggt | 1080 |
| caacgcgctc | cactgtatta | cagccctggc | tacggtcctg | ccagtctgta | cgattacaaa | 1140 |
| ggccgtggcg | gaagtggtag | tgaatcacgc | caactgcaac | tgatcacgca | gtactacaaa | 1200 |
| tcacagggct | caggtagtag | tcagggtgac | gacaactatg | gcctgaatct | ggggaaagga | 1260 |
| ttctctgcca | tttcaggcag | ctcaacgccg | tatgtgagta | aaggactgaa | cagcgaccgc | 1320 |
| attccgggaa | ccgagcgtgg | cagtggttca | gaccctttca | acatcgatca | cattgaggtg | 1380 |
| atctctggtg | cgaccggctc | tggctcagat | gaatcactgc | gcttttaccc | attcccgaca | 1440 |

```
gtaaatgcga acaaacaagc gaccgccttt tcaagctcac agcaagatac agatcaaggc    1500
tctggttctg tagcccaaca aaatgatgac aatgaaatca tcgtttccgc cagctaa       1557
```

<210> SEQ ID NO 8
<211> LENGTH: 518
<212> TYPE: PRT
<213> ORGANISM: Artificial
<220> FEATURE:
<223> OTHER INFORMATION: MoLE Protein

<400> SEQUENCE: 8

```
His His His His His His Phe Asp Arg Asp Tyr Thr Thr Val Trp Gly
1               5                   10                  15

Gln Arg Ala Pro Leu Tyr Tyr Ser Pro Gly Tyr Gly Pro Ala Ser Leu
            20                  25                  30

Tyr Asp Tyr Lys Gly Arg Gly Gly Ser Gly Ser Glu Ser Arg Gln Leu
        35                  40                  45

Gln Leu Ile Thr Gln Tyr Tyr Lys Ser Gln Gly Ser Gly Ser Ser Gln
    50                  55                  60

Gly Asp Asp Asn Tyr Gly Leu Asn Leu Gly Lys Gly Phe Ser Ala Ile
65                  70                  75                  80

Ser Gly Ser Ser Thr Pro Tyr Val Ser Lys Gly Leu Asn Ser Asp Arg
                85                  90                  95

Ile Pro Gly Thr Glu Arg Gly Ser Gly Ser Asp Pro Phe Asn Ile Asp
            100                 105                 110

His Ile Glu Val Ile Ser Gly Ala Thr Gly Ser Gly Ser Asp Glu Ser
        115                 120                 125

Leu Arg Phe Tyr Pro Phe Pro Thr Val Asn Ala Asn Lys Gln Ala Thr
    130                 135                 140

Ala Phe Ser Ser Ser Gln Gln Asp Thr Asp Gln Gly Ser Gly Ser Val
145                 150                 155                 160

Ala Gln Gln Asn Asp Asp Asn Glu Ile Ile Val Ser Ala Ser Gly Ser
                165                 170                 175

Gly Ser Phe Asp Arg Asp Tyr Thr Thr Val Trp Gly Gln Arg Ala Pro
            180                 185                 190

Leu Tyr Tyr Ser Pro Gly Tyr Gly Pro Ala Ser Leu Tyr Asp Tyr Lys
        195                 200                 205

Gly Arg Gly Gly Ser Gly Ser Glu Ser Arg Gln Leu Gln Leu Ile Thr
    210                 215                 220

Gln Tyr Tyr Lys Ser Gln Gly Ser Gly Ser Ser Gln Gly Asp Asp Asn
225                 230                 235                 240

Tyr Gly Leu Asn Leu Gly Lys Gly Phe Ser Ala Ile Ser Gly Ser Ser
                245                 250                 255

Thr Pro Tyr Val Ser Lys Gly Leu Asn Ser Asp Arg Ile Pro Gly Thr
            260                 265                 270

Glu Arg Gly Ser Gly Ser Asp Pro Phe Asn Ile Asp His Ile Glu Val
        275                 280                 285

Ile Ser Gly Ala Thr Gly Ser Gly Ser Asp Glu Ser Leu Arg Phe Tyr
    290                 295                 300

Pro Phe Pro Thr Val Asn Ala Asn Lys Gln Ala Thr Ala Phe Ser Ser
305                 310                 315                 320

Ser Gln Gln Asp Thr Asp Gln Gly Ser Gly Ser Val Ala Gln Gln Asn
                325                 330                 335
```

```
Asp Asp Asn Glu Ile Ile Val Ser Ala Ser Gly Ser Gly Ser Phe Asp
                340                 345                 350

Arg Asp Tyr Thr Thr Val Trp Gly Gln Arg Ala Pro Leu Tyr Tyr Ser
            355                 360                 365

Pro Gly Tyr Gly Pro Ala Ser Leu Tyr Asp Tyr Lys Gly Arg Gly Gly
        370                 375                 380

Ser Gly Ser Glu Ser Arg Gln Leu Gln Leu Ile Thr Gln Tyr Tyr Lys
385                 390                 395                 400

Ser Gln Gly Ser Gly Ser Ser Gln Gly Asp Asp Asn Tyr Gly Leu Asn
                405                 410                 415

Leu Gly Lys Gly Phe Ser Ala Ile Ser Gly Ser Ser Thr Pro Tyr Val
            420                 425                 430

Ser Lys Gly Leu Asn Ser Asp Arg Ile Pro Gly Thr Glu Arg Gly Ser
        435                 440                 445

Gly Ser Asp Pro Phe Asn Ile Asp His Ile Glu Val Ile Ser Gly Ala
    450                 455                 460

Thr Gly Ser Gly Ser Asp Glu Ser Leu Arg Phe Tyr Pro Phe Pro Thr
465                 470                 475                 480

Val Asn Ala Asn Lys Gln Ala Thr Ala Phe Ser Ser Gln Gln Asp
                485                 490                 495

Thr Asp Gln Gly Ser Gly Ser Val Ala Gln Gln Asn Asp Asp Asn Glu
            500                 505                 510

Ile Ile Val Ser Ala Ser
            515

<210> SEQ ID NO 9
<211> LENGTH: 1098
<212> TYPE: DNA
<213> ORGANISM: Artificial
<220> FEATURE:
<223> OTHER INFORMATION: Nucleotide sequence encoding a MoLE Protein

<400> SEQUENCE: 9
caccaccacc accaccaccg tgaagttaaa agcggcaaaa aagataaata caaccactgg      60
gatctgaact atgaaagccg taaaccgggt agcggtagtg gtattagcat taccggtggt     120
aatgaaaaac cggatattag tattggtagc ggcagcaaaa ataaccaggt tcataccctg     180
acaccgggtg aaagcctgga tgcatggacc atgcgtggta atctgaaaca gccgaatagc     240
aaacgtgaaa cccataatag ccgtagcggt tcaggtagcg aaaaagttat tcgtgaagtg     300
aaatcgggta aaaaagacaa atatggcagc ggtagccaag aacatggtaa atttggtaat     360
agcaccaccg ttctggtag tcgcgaagtg aaaagtggaa aaaagacaa atataaccat     420 tgggacctga attacgaatc acgcaaaccg ggttcaggtt caggcatttc aattacaggt     480
ggcaacgaga accagatat cagcattggc tctggtagca aaaacaatca ggtgcacaca     540 ctgaccctg tgaatcact ggacgcctgg acaatgcgtg gcaacctgaa caacctaat     600 tcaaaacgcg aaacgcataa ctcacgtagt ggttctggtt cagaaaaagt gatccgcgag     660
gttaaatcag ggaaaaaaga taaatatggg tccggctcac aagaacacgg caaattcggc     720
aattcaacca ccggcagtgg ttcacgtgag gtgaaatctg gcaaaaaaga caaatacaat     780
cattgggacc tgaactatga gtctcgtaaa cctggttctg gcagcggcat tagtattaca     840
ggcggaaacg aaaaacctga catttctatt ggttccggct caaaaaacaa ccaagtacat     900
acgctgaccc caggcgagag tctggatgcg tggacgatgc gtggaaacct gaaacagcca     960
```

```
aactctaaac gtgagacaca taacagtcgc agcggcagcg gctctgagaa agtaattcgg    1020
gaagtaaaat ccggaaaaaa agataaatac ggttcgggca gccaagagca cggaaaattt    1080
ggcaacagta ccaccta                                                    1098
```

<210> SEQ ID NO 10
<211> LENGTH: 365
<212> TYPE: PRT
<213> ORGANISM: Artificial
<220> FEATURE:
<223> OTHER INFORMATION: MoLE Protein

<400> SEQUENCE: 10

```
His His His His His His Arg Glu Val Lys Ser Gly Lys Lys Asp Lys
1               5                   10                  15

Tyr Asn His Trp Asp Leu Asn Tyr Glu Ser Arg Lys Pro Gly Ser Gly
            20                  25                  30

Ser Gly Ile Ser Ile Thr Gly Gly Asn Glu Lys Pro Asp Ile Ser Ile
        35                  40                  45

Gly Ser Gly Ser Lys Asn Asn Gln Val His Thr Leu Thr Pro Gly Glu
    50                  55                  60

Ser Leu Asp Ala Trp Thr Met Arg Gly Asn Leu Lys Gln Pro Asn Ser
65                  70                  75                  80

Lys Arg Glu Thr His Asn Ser Arg Ser Gly Ser Gly Ser Glu Lys Val
                85                  90                  95

Ile Arg Glu Val Lys Ser Gly Lys Lys Asp Lys Tyr Gly Ser Gly Ser
            100                 105                 110

Gln Glu His Gly Lys Phe Gly Asn Ser Thr Thr Gly Ser Gly Ser Arg
        115                 120                 125

Glu Val Lys Ser Gly Lys Lys Asp Lys Tyr Asn His Trp Asp Leu Asn
    130                 135                 140

Tyr Glu Ser Arg Lys Pro Gly Ser Gly Ser Gly Ile Ser Ile Thr Gly
145                 150                 155                 160

Gly Asn Glu Lys Pro Asp Ile Ser Ile Gly Ser Gly Ser Lys Asn Asn
                165                 170                 175

Gln Val His Thr Leu Thr Pro Gly Glu Ser Leu Asp Ala Trp Thr Met
            180                 185                 190

Arg Gly Asn Leu Lys Gln Pro Asn Ser Lys Arg Glu Thr His Asn Ser
        195                 200                 205

Arg Ser Gly Ser Gly Ser Glu Lys Val Ile Arg Glu Val Lys Ser Gly
    210                 215                 220

Lys Lys Asp Lys Tyr Gly Ser Gly Ser Gln Glu His Gly Lys Phe Gly
225                 230                 235                 240

Asn Ser Thr Thr Gly Ser Gly Ser Arg Glu Val Lys Ser Gly Lys Lys
                245                 250                 255

Asp Lys Tyr Asn His Trp Asp Leu Asn Tyr Glu Ser Arg Lys Pro Gly
            260                 265                 270

Ser Gly Ser Gly Ile Ser Ile Thr Gly Gly Asn Glu Lys Pro Asp Ile
        275                 280                 285

Ser Ile Gly Ser Gly Ser Lys Asn Asn Gln Val His Thr Leu Thr Pro
    290                 295                 300

Gly Glu Ser Leu Asp Ala Trp Thr Met Arg Gly Asn Leu Lys Gln Pro
305                 310                 315                 320

Asn Ser Lys Arg Glu Thr His Asn Ser Arg Ser Gly Ser Gly Ser Glu
                325                 330                 335
```

```
Lys Val Ile Arg Glu Val Lys Ser Gly Lys Lys Asp Lys Tyr Gly Ser
                340                 345                 350

Gly Ser Gln Glu His Gly Lys Phe Gly Asn Ser Thr Thr
            355                 360                 365

<210> SEQ ID NO 11

<400> SEQUENCE: 11

000

<210> SEQ ID NO 12
<211> LENGTH: 33
<212> TYPE: PRT
<213> ORGANISM: Artificial
<220> FEATURE:
<223> OTHER INFORMATION: B cell domain

<400> SEQUENCE: 12

Phe Asp Arg Asp Tyr Thr Thr Val Trp Gly Gln Arg Ala Pro Leu Tyr
1               5                   10                  15

Tyr Ser Pro Gly Tyr Gly Pro Ala Ser Leu Tyr Asp Tyr Lys Gly Arg
            20                  25                  30

Gly

<210> SEQ ID NO 13
<211> LENGTH: 40
<212> TYPE: PRT
<213> ORGANISM: Artificial
<220> FEATURE:
<223> OTHER INFORMATION: B cell domain

<400> SEQUENCE: 13

Ser Gln Gly Asp Asp Asn Tyr Gly Leu Asn Leu Gly Lys Gly Phe Ser
1               5                   10                  15

Ala Ile Ser Gly Ser Ser Thr Pro Tyr Val Ser Lys Gly Leu Asn Ser
            20                  25                  30

<210> SEQ ID NO 16
<211> LENGTH: 15
<212> TYPE: PRT
<213> ORGANISM: Artificial
<220> FEATURE:
<223> OTHER INFORMATION: T cell domain

<400> SEQUENCE: 16

Asp Pro Phe Asn Ile Asp His Ile Glu Val Ile Ser Gly Ala Thr
1               5                   10                  15

<210> SEQ ID NO 17
<211> LENGTH: 15
<212> TYPE: PRT
<213> ORGANISM: Artificial
<220> FEATURE:
<223> OTHER INFORMATION: T cell domain

<400> SEQUENCE: 17

Val Ala Gln Gln Asn Asp Asp Asn Glu Ile Ile Val Ser Ala Ser
1               5                   10                  15

<210> SEQ ID NO 18
<211> LENGTH: 23
<212> TYPE: PRT
<213> ORGANISM: Artificial
<220> FEATURE:
<223> OTHER INFORMATION: B cell domain

<400> SEQUENCE: 18

Arg Glu Val Lys Ser Gly Lys Lys Asp Lys Tyr Asn His Trp Asp Leu
1               5                   10                  15

Asn Tyr Glu Ser Arg Lys Pro
            20

<210> SEQ ID NO 19
<211> LENGTH: 37
<212> TYPE: PRT
<213> ORGANISM: Artificial
<220> FEATURE:
<223> OTHER INFORMATION: B cell domain

<400> SEQUENCE: 19

Lys Asn Asn Gln Val His Thr Leu Thr Pro Gly Glu Ser Leu Asp Ala
1               5                   10                  15

Trp Thr Met Arg Gly Asn Leu Lys Gln Pro Asn Ser Lys Arg Glu Thr
            20                  25                  30

His Asn Ser Arg Ser
        35

<210> SEQ ID NO 20
<211> LENGTH: 11
<212> TYPE: PRT
<213> ORGANISM: Artificial
<220> FEATURE:
<223> OTHER INFORMATION: B cell domain

<400> SEQUENCE: 20

Gln Glu His Gly Lys Phe Gly Asn Ser Thr Thr
1               5                   10

<210> SEQ ID NO 21
<211> LENGTH: 15
<212> TYPE: PRT
<213> ORGANISM: Artificial

```
<220> FEATURE:
<223> OTHER INFORMATION: T cell domain

<400> SEQUENCE: 21

Gly Ile Ser Ile Thr Gly Gly Asn Glu Lys Pro Asp Ile Ser Ile
1               5                   10                  15

<210> SEQ ID NO 22
<211> LENGTH: 15
<212> TYPE: PRT
<213> ORGANISM: Artificial
<220> FEATURE:
<223> OTHER INFORMATION: T cell domain

<400> SEQUENCE: 22

Glu Lys Val Ile Arg Glu Val Lys Ser Gly Lys Lys Asp Lys Tyr
1               5                   10                  15

<210> SEQ ID NO 23
<211> LENGTH: 4
<212> TYPE: PRT
<213> ORGANISM: Artificial
<220> FEATURE:
<223> OTHER INFORMATION: Linker

<400> SEQUENCE: 23

Gly Ser Gly Ser
1

<210> SEQ ID NO 24
<211> LENGTH: 5
<212> TYPE: PRT
<213> ORGANISM: Artificial
<220> FEATURE:
<223> OTHER INFORMATION: Linker

<400> SEQUENCE: 24

Gly Pro Gly Pro Gly
1               5

<210> SEQ ID NO 25
<211> LENGTH: 1269
<212> TYPE: DNA
<213> ORGANISM: Artificial
<220> FEATURE:
<223> OTHER INFORMATION: Nucleotide sequence encoding a MoLE Protein

<400> SEQUENCE: 25
catcatcacc atcaccatcg tgaagttaaa agcggcaaaa agataaaata caaccactgg      60
gatctgaact atgaaagccg taaaccgggt agcggtagcg aaagccgtca gctgcaactg     120
attacccagt attacaaaag ccagggtagc ggcagcaaaa ataaccaggt tcatacccctg    180 acaccgggtg aaagcctgga tgcatggacc atgcgtggta atctgaaaca gccgaatagc    240
aaacgtgaaa cccataatag ccgtagcggt tcaggtagcg atccgtttaa cattgatcat    300
attgaagtta ttagcggtgc aaccggtagc ggttcacaag aacatggtaa atttggtaat    360
agcaccaccg gtagtggtag cgttgcacag cagaatgatg ataacgaaat tattgttagc    420
gcaagcggca gcggtagccg cgaagtgaaa agtggaaaaa agacaaaata taaccattgg    480
gacctgaatt acgaatcacg caaaccgggt tcaggttcag aaagtcgtca actgcagctg    540
atcacacaat actataaaag tcagggttct ggtagcaaaa acaatcaggt gcacacactg    600
acccctggtg aatcactgga cgcctggaca atgcgtggca acctgaaaca acctaattca    660
```

```
aaacgcgaaa cgcataactc acgtagtggt agtggcagtg atccgttcaa tatcgaccat    720
atcgaagtga tttcaggtgc caccggttca ggcagtcaag aacacggcaa attcggcaat    780
tcaaccaccg gttcaggctc agtggcccag cagaacgacg ataatgagat cattgtgagc    840
gcctcaggca gcggttctcg tgaggtgaaa tctggcaaaa aagacaaata caatcattgg    900
gacctgaact atgagtctcg taaacctgga agtggtagtg aatcacgcca actgcaactg    960
atcacgcagt actacaaatc acagggctca ggtagtaaaa acaaccaagt acatacgctg   1020
accccaggcg agagtctgga tgcgtggacg atgcgtggaa acctgaaaca gccaaactct   1080
aaacgtgaga cacataacag tcgcagcggc agtggttcag acccttcaa catcgatcac   1140 attgaggtga tctctggtgc gaccggctct ggctcacaag agcacggaaa atttggcaac   1200
agtaccaccg gctctggttc tgtagcccaa caaaatgatg acaatgaaat catcgtttcc   1260
gccagctaa                                                            1269
```

<210> SEQ ID NO 26
<211> LENGTH: 422
<212> TYPE: PRT
<213> ORGANISM: Artificial
<220> FEATURE:
<223> OTHER INFORMATION: MoLE Protein

<400> SEQUENCE: 26

```
His His His His His His Arg Glu Val Lys Ser Gly Lys Lys Asp Lys
1               5                   10                  15

Tyr Asn His Trp Asp Leu Asn Tyr Glu Ser Arg Lys Pro Gly Ser Gly
            20                  25                  30

Ser Glu Ser Arg Gln Leu Gln Leu Ile Thr Gln Tyr Tyr Lys Ser Gln
        35                  40                  45

Gly Ser Gly Ser Lys Asn Asn Gln Val His Thr Leu Thr Pro Gly Glu
    50                  55                  60

Ser Leu Asp Ala Trp Thr Met Arg Gly Asn Leu Lys Gln Pro Asn Ser
65                  70                  75                  80

Lys Arg Glu Thr His Asn Ser Arg Ser Gly Ser Gly Ser Asp Pro Phe
                85                  90                  95

Asn Ile Asp His Ile Glu Val Ile Ser Gly Ala Thr Gly Ser Gly Ser
            100                 105                 110

Gln Glu His Gly Lys Phe Gly Asn Ser Thr Thr Gly Ser Gly Ser Val
        115                 120                 125

Ala Gln Gln Asn Asp Asp Asn Glu Ile Ile Val Ser Ala Ser Gly Ser
    130                 135                 140

Gly Ser Arg Glu Val Lys Ser Gly Lys Lys Asp Lys Tyr Asn His Trp
145                 150                 155                 160

Asp Leu Asn Tyr Glu Ser Arg Lys Pro Gly Ser Gly Ser Glu Ser Arg
                165                 170                 175

Gln Leu Gln Leu Ile Thr Gln Tyr Tyr Lys Ser Gln Gly Ser Gly Ser
            180                 185                 190

Lys Asn Asn Gln Val His Thr Leu Thr Pro Gly Glu Ser Leu Asp Ala
        195                 200                 205

Trp Thr Met Arg Gly Asn Leu Lys Gln Pro Asn Ser Lys Arg Glu Thr
    210                 215                 220

His Asn Ser Arg Ser Gly Ser Gly Ser Asp Pro Phe Asn Ile Asp His
225                 230                 235                 240

Ile Glu Val Ile Ser Gly Ala Thr Gly Ser Gly Ser Gln Glu His Gly
                245                 250                 255
```

-continued

```
Lys Phe Gly Asn Ser Thr Thr Gly Ser Gly Ser Val Ala Gln Gln Asn
            260                 265                 270

Asp Asp Asn Glu Ile Ile Val Ser Ala Ser Gly Ser Gly Ser Arg Glu
        275                 280                 285

Val Lys Ser Gly Lys Lys Asp Lys Tyr Asn His Trp Asp Leu Asn Tyr
290                 295                 300

Glu Ser Arg Lys Pro Gly Ser Gly Ser Glu Ser Arg Gln Leu Gln Leu
305                 310                 315                 320

Ile Thr Gln Tyr Tyr Lys Ser Gln Gly Ser Gly Ser Lys Asn Asn Gln
            325                 330                 335

Val His Thr Leu Thr Pro Gly Glu Ser Leu Asp Ala Trp Thr Met Arg
        340                 345                 350

Gly Asn Leu Lys Gln Pro Asn Ser Lys Arg Glu Thr His Asn Ser Arg
            355                 360                 365

Ser Gly Ser Gly Ser Asp Pro Phe Asn Ile Asp His Ile Glu Val Ile
370                 375                 380

Ser Gly Ala Thr Gly Ser Gly Ser Gln Glu His Gly Lys Phe Gly Asn
385                 390                 395                 400

Ser Thr Thr Gly Ser Gly Ser Val Ala Gln Gln Asn Asp Asp Asn Glu
            405                 410                 415

Ile Ile Val Ser Ala Ser
            420

<210> SEQ ID NO 27
<211> LENGTH: 372
<212> TYPE: DNA
<213> ORGANISM: Artificial
<220> FEATURE:
<223> OTHER INFORMATION: Nucleotide sequence encoding a MoLE Protein

<400> SEQUENCE: 27
caccaccacc accaccaccg tgaagttaaa agcggcaaaa aagataaata caaccactgg      60
gatctgaact atgaaagccg taaccgggt agcggtagtg gtattagcat taccggtggt      120
aatgaaaaac cggatattag tattggtagc ggcagcaaaa ataaccaggt tcatacccctg     180 acaccgggtg aaagcctgga tgcatggacc atgcgtggta atctgaaaca gccgaatagc      240
aaacgtgaaa cccataatag ccgtagcggt tcaggtagcg aaaaagttat tcgtgaagtg      300
aaatcgggta aaaaagacaa atatggcagc ggtagccaag aacatggtaa atttggtaat      360
agcaccacct aa                                                         372

<210> SEQ ID NO 28
<211> LENGTH: 461
<212> TYPE: PRT
<213> ORGANISM: Artificial
<220> FEATURE:
<223> OTHER INFORMATION: MoLE Protein

<400> SEQUENCE: 28

His His His His His His Phe Asp Arg Asp Tyr Thr Thr Val Trp Gly
1               5                   10                  15

Gln Arg Ala Pro Leu Tyr Tyr Ser Pro Gly Tyr Gly Pro Ala Ser Leu
            20                  25                  30

Tyr Asp Tyr Lys Gly Arg Gly Gly Ser Gly Ser Gly Ile Ser Ile Thr
        35                  40                  45

Gly Gly Asn Glu Lys Pro Asp Ile Ser Ile Gly Ser Gly Ser Ser Gln
    50                  55                  60
```

Gly Asp Asp Asn Tyr Gly Leu Asn Leu Gly Lys Gly Phe Ser Ala Ile
 65                  70                  75                  80

Ser Gly Ser Ser Thr Pro Tyr Val Ser Lys Gly Leu Asn Ser Asp Arg
             85                  90                  95

Ile Pro Gly Thr Glu Arg Gly Ser Gly Ser Glu Lys Val Ile Arg Glu
            100                 105                 110

Val Lys Ser Gly Lys Lys Asp Lys Tyr Gly Ser Gly Ser Asp Glu Ser
            115                 120                 125

Leu Arg Phe Tyr Pro Phe Pro Thr Val Asn Ala Asn Lys Gln Ala Thr
130                 135                 140

Ala Phe Ser Ser Ser Gln Asp Thr Asp Gln Gly Ser Gly Ser Phe
145                 150                 155                 160

Asp Arg Asp Tyr Thr Thr Val Trp Gly Gln Arg Ala Pro Leu Tyr Tyr
                165                 170                 175

Ser Pro Gly Tyr Gly Pro Ala Ser Leu Tyr Asp Tyr Lys Gly Arg Gly
            180                 185                 190

Gly Ser Gly Ser Gly Ile Ser Ile Thr Gly Gly Asn Glu Lys Pro Asp
            195                 200                 205

Ile Ser Ile Gly Ser Gly Ser Gln Gly Asp Asp Asn Tyr Gly Leu
210                 215                 220

Asn Leu Gly Lys Gly Phe Ser Ala Ile Ser Gly Ser Ser Thr Pro Tyr
225                 230                 235                 240

Val Ser Lys Gly Leu Asn Ser Asp Arg Ile Pro Gly Thr Glu Arg Gly
                245                 250                 255

Ser Gly Ser Glu Lys Val Ile Arg Glu Val Lys Ser Gly Lys Lys Asp
            260                 265                 270

Lys Tyr Gly Ser Gly Ser Asp Glu Ser Leu Arg Phe Tyr Pro Phe Pro
    275                 280                 285

Thr Val Asn Ala Asn Lys Gln Ala Thr Ala Phe Ser Ser Ser Gln Gln
    290                 295                 300

Asp Thr Asp Gln Gly Ser Gly Ser Phe Asp Arg Asp Tyr Thr Thr Val
305                 310                 315                 320

Trp Gly Gln Arg Ala Pro Leu Tyr Tyr Ser Pro Gly Tyr Gly Pro Ala
                325                 330                 335

Ser Leu Tyr Asp Tyr Lys Gly Arg Gly Gly Ser Gly Ser Gly Ile Ser
            340                 345                 350

Ile Thr Gly Gly Asn Glu Lys Pro Asp Ile Ser Ile Gly Ser Gly Ser
            355                 360                 365

Ser Gln Gly Asp Asp Asn Tyr Gly Leu Asn Leu Gly Lys Gly Phe Ser
    370                 375                 380

Ala Ile Ser Gly Ser Ser Thr Pro Tyr Val Ser Lys Gly Leu Asn Ser
385                 390                 395                 400

Asp Arg Ile Pro Gly Thr Glu Arg Gly Ser Gly Ser Glu Lys Val Ile
                405                 410                 415

Arg Glu Val Lys Ser Gly Lys Lys Asp Lys Tyr Gly Ser Gly Ser Asp
            420                 425                 430

Glu Ser Leu Arg Phe Tyr Pro Phe Pro Thr Val Asn Ala Asn Lys Gln
            435                 440                 445

Ala Thr Ala Phe Ser Ser Ser Gln Gln Asp Thr Asp Gln
450                 455                 460

<210> SEQ ID NO 29
<211> LENGTH: 372

```
<212> TYPE: DNA
<213> ORGANISM: Artificial
<220> FEATURE:
<223> OTHER INFORMATION: Nucleotide sequence encoding a MoLE Protein

<400> SEQUENCE: 29
caccaccacc accaccaccg tgaagttaaa agcggcaaaa aagataaata caaccactgg      60
gatctgaact atgaaagccg taaaccgggt agcggtagtg gtattagcat taccggtggt     120
aatgaaaaac cggatattag tattggtagc ggcagcaaaa ataaccaggt tcataccctg     180
acaccgggtg aaagcctgga tgcatggacc atgcgtggta atctgaaaca gccgaatagc     240
aaacgtgaaa cccataatag ccgtagcggt tcaggtagcg aaaaagttat tcgtgaagtg     300
aaatcgggta aaaaagacaa atatggcagc ggtagccaag aacatggtaa atttggtaat     360
agcaccacct aa                                                         372

<210> SEQ ID NO 30
<211> LENGTH: 123
<212> TYPE: PRT
<213> ORGANISM: Artificial
<220> FEATURE:
<223> OTHER INFORMATION: MoLE Protein

<400> SEQUENCE: 30

His His His His His His Arg Glu Val Lys Ser Gly Lys Lys Asp Lys
1               5                   10                  15

Tyr Asn His Trp Asp Leu Asn Tyr Glu Ser Arg Lys Pro Gly Ser Gly
            20                  25                  30

Ser Gly Ile Ser Ile Thr Gly Gly Asn Glu Lys Pro Asp Ile Ser Ile
        35                  40                  45

Gly Ser Gly Ser Lys Asn Asn Gln Val His Thr Leu Thr Pro Gly Glu
    50                  55                  60

Ser Leu Asp Ala Trp Thr Met Arg Gly Asn Leu Lys Gln Pro Asn Ser
65                  70                  75                  80

Lys Arg Glu Thr His Asn Ser Arg Ser Gly Ser Gly Ser Glu Lys Val
                85                  90                  95

Ile Arg Glu Val Lys Ser Gly Lys Lys Asp Lys Tyr Gly Ser Gly Ser
            100                 105                 110

Gln Glu His Gly Lys Phe Gly Asn Ser Thr Thr
            115                 120
```

ENGINEERED PROTEINS AND METHODS OF USE

CROSS-REFERENCE TO RELATED APPLICATIONS

This application is the § 371 U.S. National Stage of International Application No. PCT/US2019/015164, filed Jan. 25, 2019, which claims the benefit of U.S. Provisional Application Ser. No. 62/621,796, filed Jan. 25, 2018, the disclosures of which are incorporated by reference herein in their entireties.

SEQUENCE LISTING

This application contains a Sequence Listing electronically submitted via EFS-Web to the United States Patent and Trademark Office as an ASCII text file entitled "2930055WO01_SequenceListing_ST25 2021-03-25.txt" having a size of 38.9 kilobytes and created on Mar. 29, 2021. The information contained in the Sequence Listing is incorporated by reference herein.

BACKGROUND

Bacterial infections now account for some 1.7 million cases of hospital-acquired infections yearly in the United States (4.5 per 100 admissions), with an overall mortality rate in the range of 20% to 60% or 99,000 deaths directly associated with a hospital acquired infection. The economic impact due to such infections is estimated to cost between 5 billion to 10 billion dollars annually in the United States.

Gram-negative bacterial infections and their sequelae are frequently lethal. It is estimated that over 700,000 patients develop bacterial infections each year in the United States alone. Of these, 160,000 actually develop septicemia, resulting in 50,000 deaths annually. The majority of these are hospital-acquired infections due to such gram-negative bacilli as *E. coli* (most common pathogen isolated from patients with gram-negative sepsis), followed in frequency by *Klebsiella pneumoniae* and *Pseudomonas aeruginosa*.

Infections caused by gram-negative bacteria, in the family of Enterobacteriaceae, continue to be a significant concern in both human healthcare and animal agricultural settings. Bacteria in the Enterobacteriaceae family are a large heterogeneous group whose natural habitat is the intestinal tract of both humans and animals. The family includes many genera and is subdivided into eight tribes including: Escherichieae, Edwardsielleae, Salmonelleae, Citrobactereae, Klebsielleae, Proteeae, Yersineae, and Erwineae. Many species of the Enterobacteriaceae family are often opportunistic pathogens with clinically relevant significance including *Escherichia* spp., *Klebsiella* spp., *Enterobacter* spp., *Proteus* spp., *Providencia* spp., *Serratia* spp., *Citrobacter* spp., *Morganella* spp., *Shigella* spp., and *Salmonella* spp., are among the top twenty organisms responsible for causing infection. When clinically important diseases do occur they are often caused by *E. coli*, but others can infect and cause debilitating disease. In most cases the bacteria become pathogenic when they reach tissues outside of their normal intestinal environment when normal host defenses are inadequate. This is particularly seen today in the young or elderly; often in terminal stages of a primary infection due to immunological incompetence or immunosuppression; allowing the organism to reach the blood stream to cause sepsis resulting in death or secondary sequelae.

The most important single species is *Escherichia coli*. These bacteria can harmlessly colonize the gastrointestinal tract of both humans and animals as normal flora. However, there are some strains that have evolved into pathogenic *E. coli* by acquiring virulence factors through plasmids, pathogenicity islands, transposons, and/or bacteriophages. These pathogenic *E. coli* can be categorized based on serogroups, pathogenicity mechanisms, clinical symptoms, or virulence factors. There are five categories of diarrheagenic *Escherichia coli* that cause foodborne and waterborne diseases in humans: the enteropathogenic (EPEC), enterohemorrhagic (EHEC), enterotoxigenic (ETEC), enteroinvasive (EIEC) and enteroaggregative (EAEC) strains. The virulence and pathogenesis of enteric pathogens involves both host and pathogen specific factors. Many pathogen-specific virulence determinants contribute to the pathogenesis of these bacteria. The bacterial virulence of these bacteria is the result of many different attributes, which often contribute to different steps in the complicated series of events we recognize as an infection. Infection occurs primarily by the consumption of contaminated water, food or by direct person-to-person contact. Once ingested the stages of infection common to enteric pathogens can include attachment, colonization, proliferation, tissue damage, invasion and dissemination.

Pathogenic *E. coli* is growing increasingly resistant to multiple antibiotic classes and is among the most frequently encountered species in the clinical setting. Although it naturally inhabits the human gut, *E. coli* can cause serious illness and death and has become familiar as a source of serious food-borne intestinal disease. Despite this notoriety, the bacterium's primary role as an extraintestinal pathogen is often neglected: today it is the leading cause of uncomplicated urinary tract infections (UTIs), an indication resulting in 7-8 million physician visits annually just in the United States. Using the urinary tract as a gateway, *E. coli* can cause serious septicemias; endotoxic shock often resulting in death. This bacterium is also known to cause neonatal meningitis or pneumonia when it invades other sterile parts of the body.

The most commonly recognized enteric pathogens contributing to gastrointestinal infections have been shown to be bacteria (e.g., *Salmonella* spp., *Escherichia coli*, *Shigella* spp., and *Vibrio* spp.). In the United States enteric pathogens transmitted via food and/or waterborne sources cause approximately 76 million illnesses, 325,000 hospitalizations, and 5000 deaths each year. More than 90% of the foodborne illnesses of known causes are of microbial origin. Costs associated with medical expenses and losses in productivity associated with microbial agents are estimated to be between $5.6 and $9.4 billion dollars annually. In fact, the transmission of enteric pathogens to human populations by the consumption of contaminated food and water has become a worldwide concern. Surveillance data compiled by the World Health Organization estimate that gastrointestinal infections and their sequelae result in approximately 4 million to 6 million deaths annually. More than 80% of these cases are among children under the age of five with mortality reaching 4 million. The majority of these deaths are in children less than 2 years of age. In the United States, diarrhea is the second most common infectious illness, accounting for one out of every six infectious diseases. In some developing countries, children have more than 12 episodes of diarrhea per year and diarrheal diseases account for 15 to 34 percent of all deaths.

Other important genera include *Salmonella* spp., *Yersinia* spp., *Klebsiella* spp., *Shigella* spp., *Proteus* spp., *Enterobacter* spp., *Serratia* spp., and *Citrobacter* spp. These bacteria can induce a multitude of clinical manifestations; such as sepsis; endotoxic shock; osteomyelitis; pneumonia; peritonitis; endocarditis; wound infection; reactive arthritis, meningitis, urinary tract infections (UTI), kidney failure, Guillian-Barre, Reiter syndrome, enteric diarrheal disease and other extra-intestinal symptoms.

In mammals, it has been shown that the response to tissue injury or bacterial infection results in an acute inflammatory response. This response increases capillary permeability and phagocytic infiltration resulting in the clinical signs recognized as inflammation: swelling, fever, pain and redness. If left uncontrolled, this may lead to death. The activation of humoral factors and the release of cytokines mediate systemic events collectively known as the acute phase protein response, which results in a cascade of physiological and biochemical events. The duration of this response is directly related to the severity of the injury and magnitude of the systemic infection.

The diversity of pathogens and virulence factors has complicated the development of new and improved vaccines with long lasting protection. The search for a better vaccine is prompted by the results of epidemiological and challenge studies showing that the recovery from natural infection is often followed by long lasting immunity while providing cross-protection against multiple strains and/or serotypes. To date, no effective vaccine is available yet for the prevention of these infections.

SUMMARY OF THE APPLICATION

Provided herein are non-natural proteins. In one embodiment, a protein includes an amino acid sequence having at least 80% sequence identity to the amino acid sequence of SEQ ID NO:5 or SEQ ID NO:6, wherein the protein protects an animal against infection with *E. coli.*

In one embodiment, a protein includes an amino acid sequence having at least 80% sequence identity to the amino acid sequence of SEQ ID NO:3, wherein the protein reacts with convalescent serum from an animal infected with *E. coli.* The protein can further include two or more copies of the amino acid sequence, wherein the two or more copies are present as a tandem repeat.

In one embodiment, a protein includes an amino acid sequence having at least 80% sequence identity to the amino acid sequence of SEQ ID NO:4, wherein the protein reacts with convalescent serum from an animal infected with *E. coli.* The protein can further include two or more copies of the amino acid sequence, wherein the two or more copies are present as a tandem repeat.

In one embodiment, a protein includes a B cell domain selected from the group consisting of SEQ ID NO:12, SEQ ID NO:13, and SEQ ID NO:14, and a T cell domain selected from the group consisting of SEQ ID NO:15, SEQ ID NO:16, and SEQ ID NO:17. In one embodiment, a protein includes a B cell domain selected from the group consisting of SEQ ID NO:18, SEQ ID NO:19, and SEQ ID NO:20, and a T cell domain selected from the group consisting of SEQ ID NO:21 and SEQ ID NO:22. The B cell domain and T cell domain can be present in the order B cell domain-T cell domain.

In one embodiment, a protein includes amino acids 7-518 of the amino acid sequence of SEQ ID NO:8. In one embodiment, a protein includes amino acids 7-365 of the amino acid sequence of SEQ ID NO:10. In one embodiment, a protein includes amino acids 7-422 of the amino acid sequence of SEQ ID NO:26. In one embodiment, a protein includes amino acids 7-461 of the amino acid sequence of SEQ ID NO:28.

In one embodiment, a protein includes one selected from protein 16-51 of Table 3 or protein 52-63 of Table 4, or having at least 80% sequence identity to the amino acid sequence of protein 16-51 of Table 3 or protein 52-63 of Table 3. The protein can further include a linker located between a B cell domain and a T cell domain, or between each B cell domain and T cell domain.

In one embodiment, a protein includes a first domain including an amino acid sequence having at least 80% identity to amino acids 1-33 of SEQ ID NO:1, a second domain including an amino acid sequence having at least 80% identity to amino acids 34-48 of SEQ ID NO:1, a third domain including an amino acid sequence having at least 80% identity to amino acids 49-88 of SEQ ID NO:1, a fourth domain including an amino acid sequence having at least 80% identity to amino acids 89-103 of SEQ ID NO:1, a fifth domain including an amino acid sequence having at least 80% identity to amino acids 104-133 of SEQ ID NO:1, and a sixth domain including an amino acid sequence having at least 80% identity to amino acids 34-148 of SEQ ID NO:1, wherein the first, third, and fifth domains have B cell activity and the second, fourth, and sixth domains have T cell activity, and wherein the protein protects an animal against infection with *E. coli.*

In one embodiment, a protein includes a first domain including an amino acid sequence having at least 80% identity to amino acids 1-23 of SEQ ID NO:2, a second domain including an amino acid sequence having at least 80% identity to amino acids 24-38 of SEQ ID NO:2, a third domain including an amino acid sequence having at least 80% identity to amino acids 39-75 of SEQ ID NO:2, a fourth domain including an amino acid sequence having at least 80% identity to amino acids 76-90 of SEQ ID NO:2, and a fifth domain including an amino acid sequence having at least 80% identity to amino acids 91-101 of SEQ ID NO:2, wherein the first, third, and fifth domains have B cell activity and the second and fourth domains have T cell activity, and wherein the protein protects an animal against infection with *E. coli.*

Also provided is a composition that includes one or more of the proteins described herein In one embodiment, the composition includes a pharmaceutically acceptable carrier. In one embodiment, the composition includes an adjuvant.

Also provided are methods. In one embodiment, a method includes administering to a subject an amount of the composition described herein effective to induce the subject to produce antibody that specifically binds to the protein, produce helper T cells, suppressor T cells, and/or cytotoxic T cells directed to an epitope of a protein present in the composition, or a combination thereof.

In one embodiment, a method is for treating an infection in a subject, and includes administering an effective amount of a composition described herein to a subject having or at risk of having an infection caused by a gram-negative microbe.

In one embodiment, a method is for treating a symptom in a subject, and includes administering an effective amount of a composition described herein to a subject having or at risk of having an infection caused by a gram-negative microbe.

In one embodiment, a method is for decreasing colonization in a subject, and includes administering an effective amount of a composition described herein to a subject colonized by a gram-negative microbe.

In one embodiment, a method is for treating a condition in a subject, and includes administering an effective amount of a composition described herein to a subject in need thereof, wherein the subject has or is at risk of having a condition caused by a gram-negative microbe.

In one embodiment, a method is for treating an infection in a subject, and includes administering an effective amount of a composition to a subject having or at risk of having an infection caused by a gram-negative microbe, wherein the composition includes antibody that specifically binds to a protein of a composition described herein.

In one embodiment, a method is for treating a symptom in a subject including administering an effective amount of a composition to a subject having or at risk of having an infection caused by a gram-negative microbe, wherein the composition includes antibody that specifically binds to a protein of a composition described herein.

In one embodiment, a method is for decreasing colonization in a subject, and includes administering an effective amount of a composition to a subject colonized by a gram-negative microbe, wherein the composition includes antibody that specifically binds to a protein of a composition described herein.

In one embodiment, a method is for treating a condition in a subject, and includes administering an effective amount of a composition to a subject in need thereof, wherein the composition includes antibody that specifically binds to a protein of a composition described herein, wherein the subject has or is at risk of having a condition caused by a gram-negative microbe.

In one embodiment, the gram-negative microbe is a pathogenic microbe that is a member of the family Vibrionaceae, a member of the family Enterobacteriaceae such as *E. coli* or *Klebsiella* spp., a member of the family Pasteurellaceae, a member of the family Pseudomonadaceae, or a *Campylobacter* spp. In one embodiment, the subject is a mammal, such as a human or a bovine, or an avian, such as a domesticated fowl.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Definitions

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

In the description herein particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

BRIEF DESCRIPTION OF THE FIGURES

FIG. 8A. IgG titers against Trimer-2 at 3 weeks after the second vaccination. FIG. 8B. Serum IgG titers against Trimer-1 at 3 (solid fill) and 8 (diagonal fill) weeks after the second vaccination.

Titers were determined by ELISA with the vaccine antigen, Trimer-1 or Trimer-2, coated on the plate. (LOD, limit of detection)

Figure 9A:
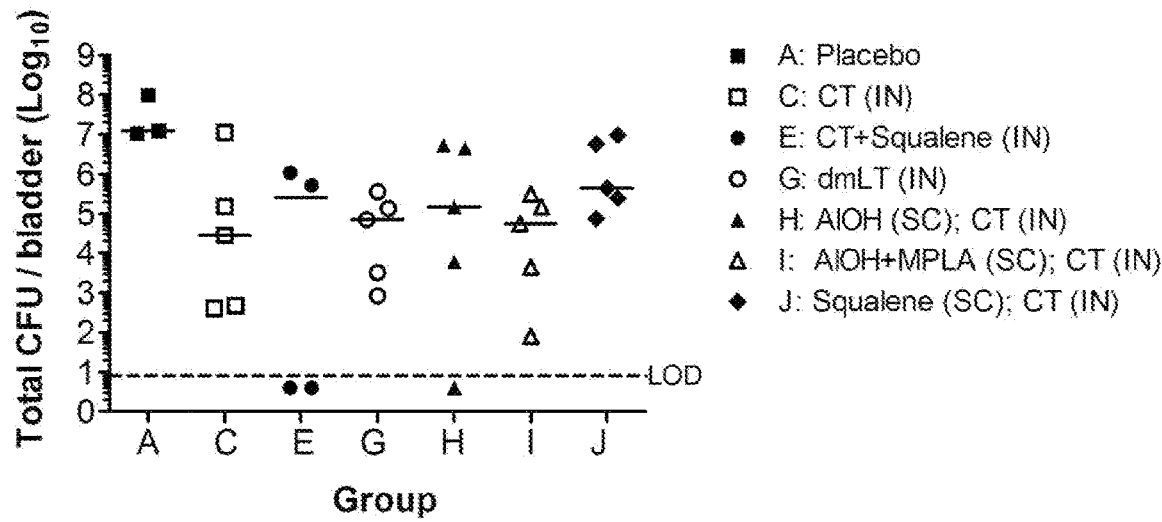
Figure 9B:
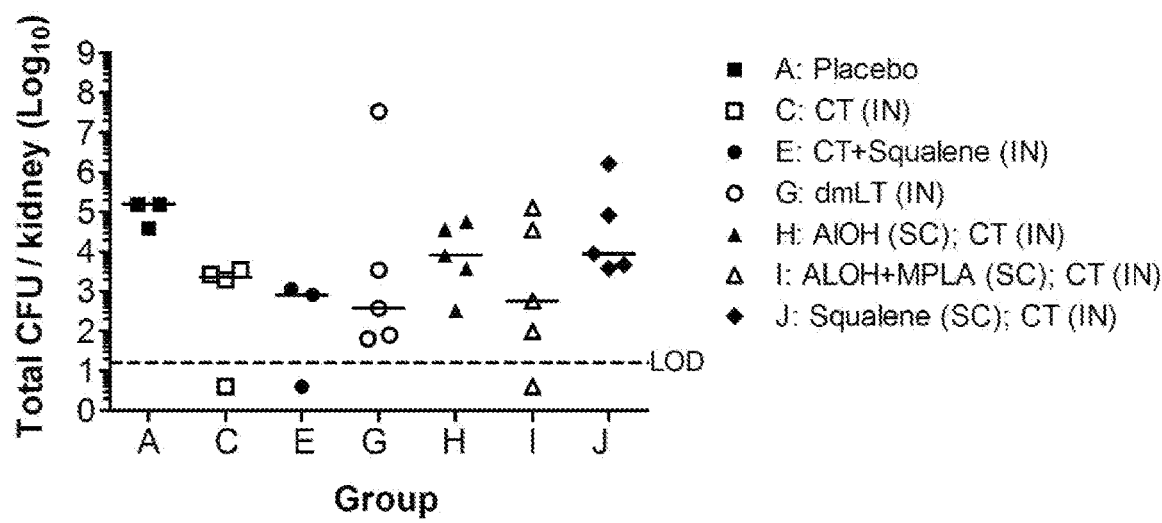

FIGS. 9A-B show colonization of bladder and kidney at 7 days after transurethral challenge with UPEC-25, a clinical UTI isolate. Vaccinated mice received different formulations of Trimer-1 as shown followed by the route of administration in parentheses. In cases where mice received a heterologous prime-boost, the priming formulation and route are shown first, followed by the boost formulation and route used for the second, third, and fourth immunizations. The median level of colonization is indicated for bladder (FIG. 9A) and for kidney (FIG. 9B). (LOD, limit of detection)

Figure 10A:
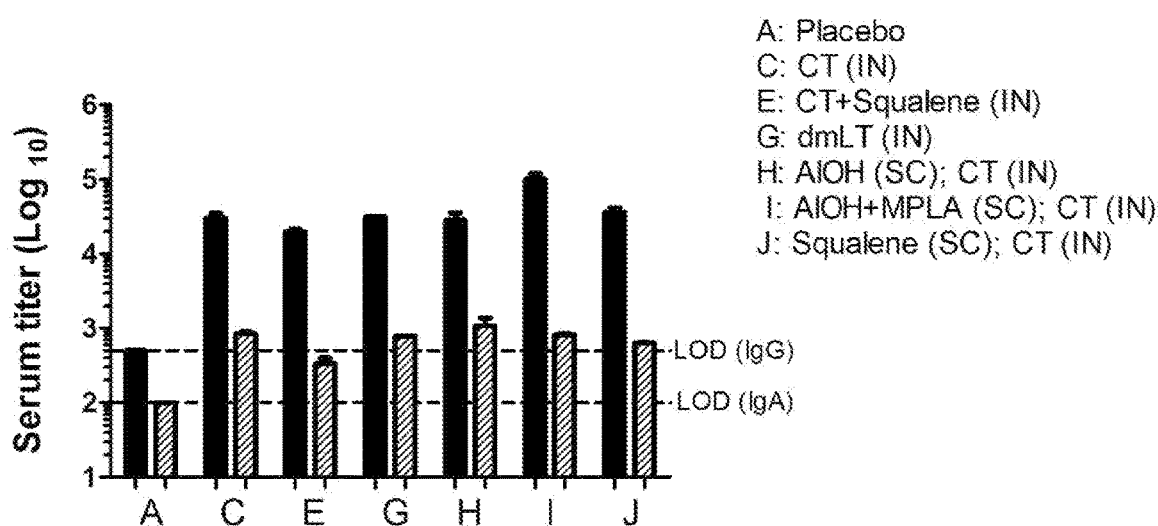
Figure 10B:
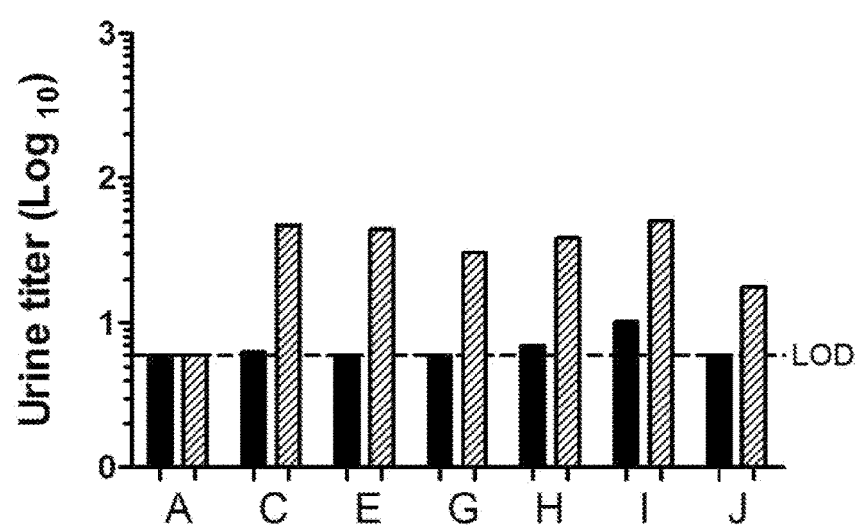
Figure 10C:
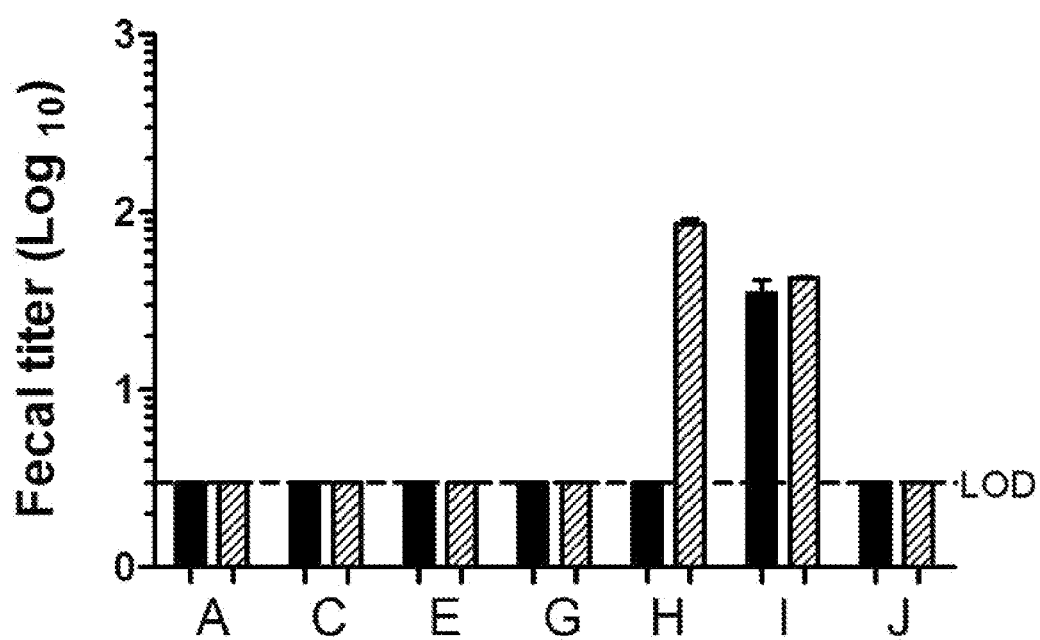

FIGS. 10A-C show IgG and IgA titers in mice immunized with different formulations of Trimer-1. Formulations are as indicated followed by the route of administration in parentheses. In cases where mice received a heterologous prime-boost, the priming formulation and route are shown first, followed by the boost formulation and route used for the second, third, and fourth immunizations. The titer of IgG (solid fill) and IgA (diagonal fill) in serum (FIG. 10A), urine (FIG. 10B), and feces (FIG. 10C) was determined using pooled samples from each group. (LOD, limit of detection)

Figure 11A:
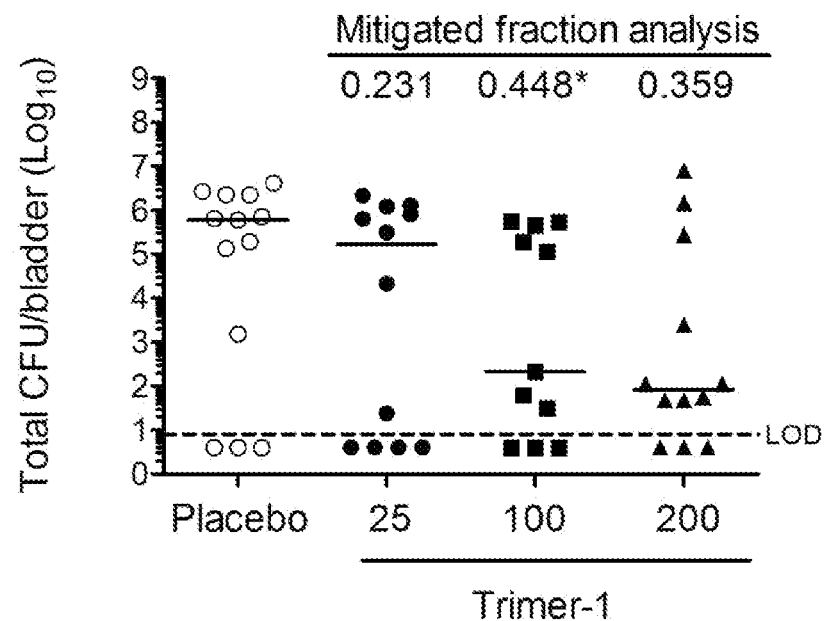
Figure 11B:
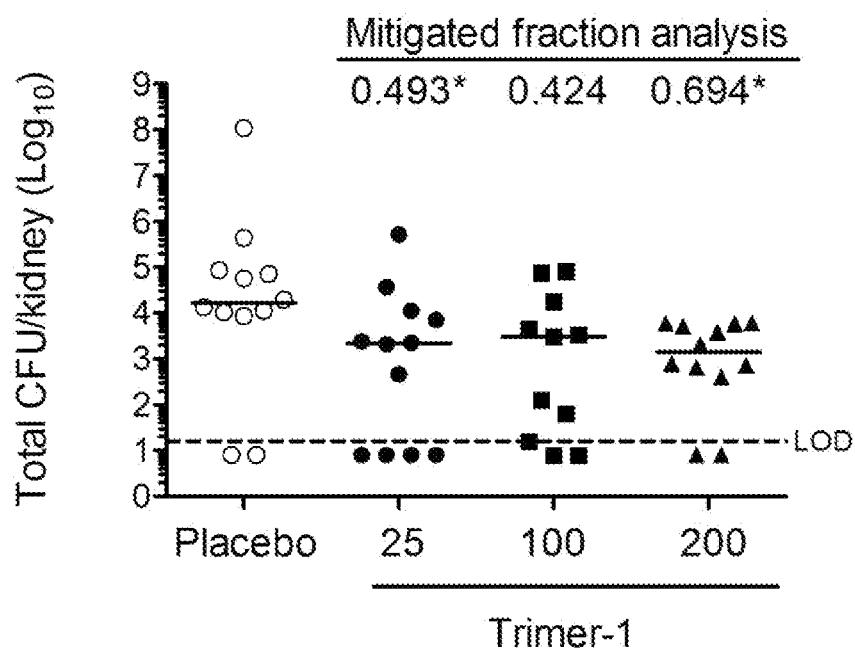

FIGS. 11A-B show colonization of bladder and kidney at 7 days after transurethral challenge with UPEC-25. Vaccinated mice received escalating doses of Trimer-1 as indicated (25, 100, or 200 µg), and the median level of colonization is shown for bladder (FIG. 11A) and for kidney (FIG. 11B). The results of mitigated fraction analysis are shown and marked with an asterisk (*) if significant. (LOD, limit of detection)

FIGS. 12A-C shows IgG and IgA titers in mice immunized with escalating doses of Trimer-1. The titer of IgG and IgA in serum (FIG. 12A), urine (FIG. 12B), and feces (FIG. 12C) was determined in individual mice from each group, and the mean titer for each group is indicated. (LOD, limit of detection)

Figure 13:
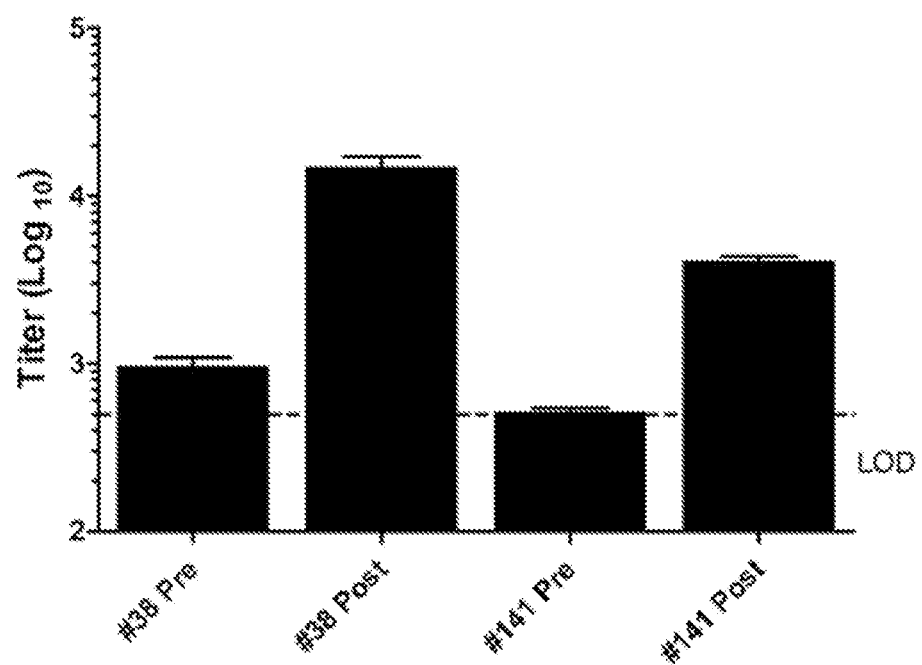

FIG. 13 shows serum IgG titers to Trimer-1 in calves. Two calves were vaccinated subcutaneously with Trimer-1 formulated in aluminum hydroxide (calf #38 and #141). Titers for individual animals were determined pre- and post-vaccination. (LOD, limit of detection)

FIG. 14A shows the electrophoretic outer membrane protein profiles for *Klebsiella pneumoniae*, *E. coli* APEC-280 and *E. coli* CFT073 examined (lane 1,—molecular weight marker; lane 2,—blank; lane 3,—*Klebsiella pneumoniae*; lane 4,—*E. coli* APEC-280; lane 5,—*E. coli* CFT073; and lane 6,—blank). Western blot analysis (FIG. 14B) revealed that the Trimer-1 positive antisera reacted against multiple membrane-associated proteins of *Klebsiella pneumoniae*, *E. coli* CFT073 and APEC-280

Figure 15A:
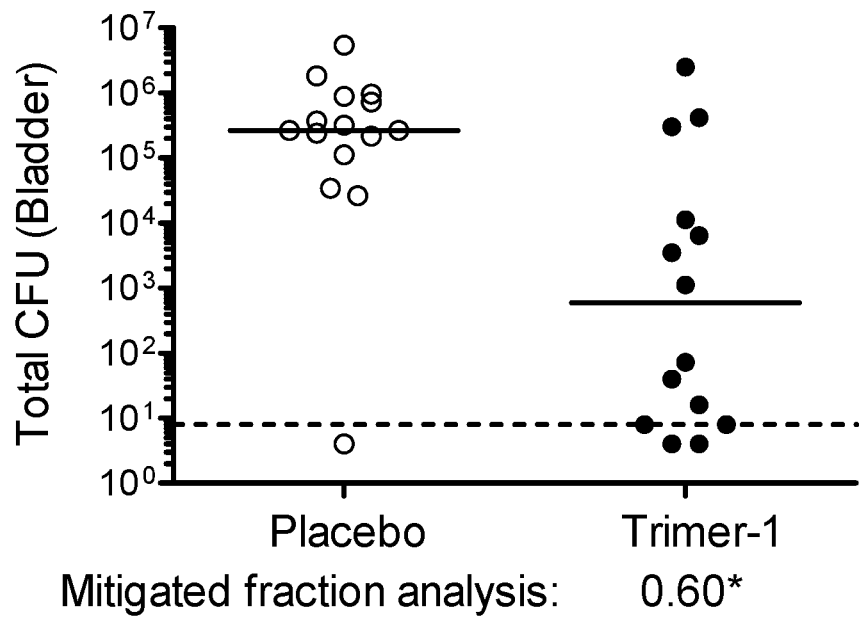
Figure 15B:
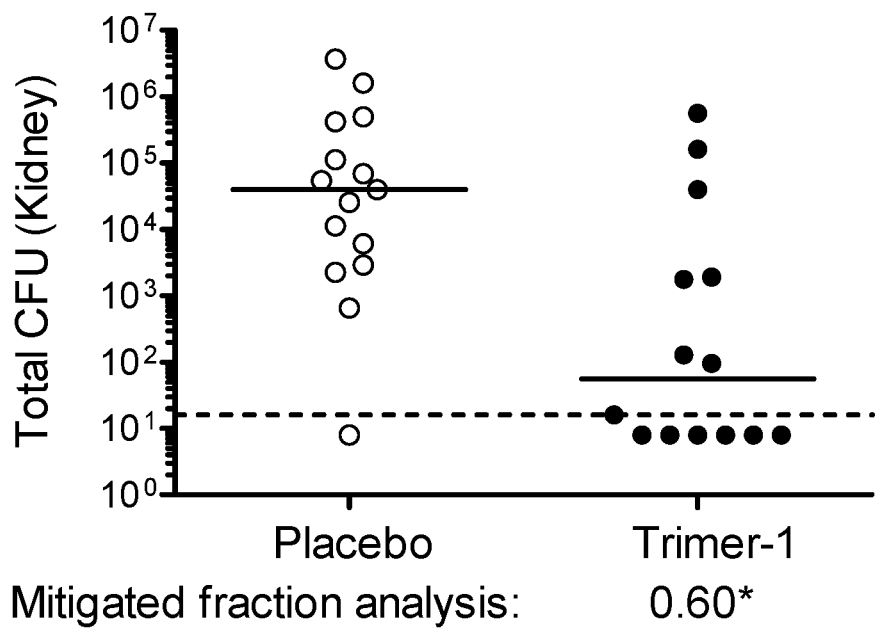

FIGS. 15A-B show therapeutic vaccine efficacy in mice challenged transurethrally with *E. coli* strain UPEC-25 prior to immunization with Trimer-1. One day following challenge, mice in group B (Trimer-1) were immunized with 100 µg of Trimer-1 antigen delivered SC and 100 µg of Trimer-1 antigen delivered IN. Placebo animals received equivalent vaccine with the antigen replaced by an equal volume of PBS. Mice were immunized IN on days 4, 5 and 6 with either Trimer-1 or placebo vaccine. Colonization of bladders and kidneys was assessed at Day 14. Mice immunized with Trimer-1 after challenge have significantly fewer bacteria present in both the bladder and kidney compared with mice in the placebo group (mitigated fraction analysis).

Figure 16A:
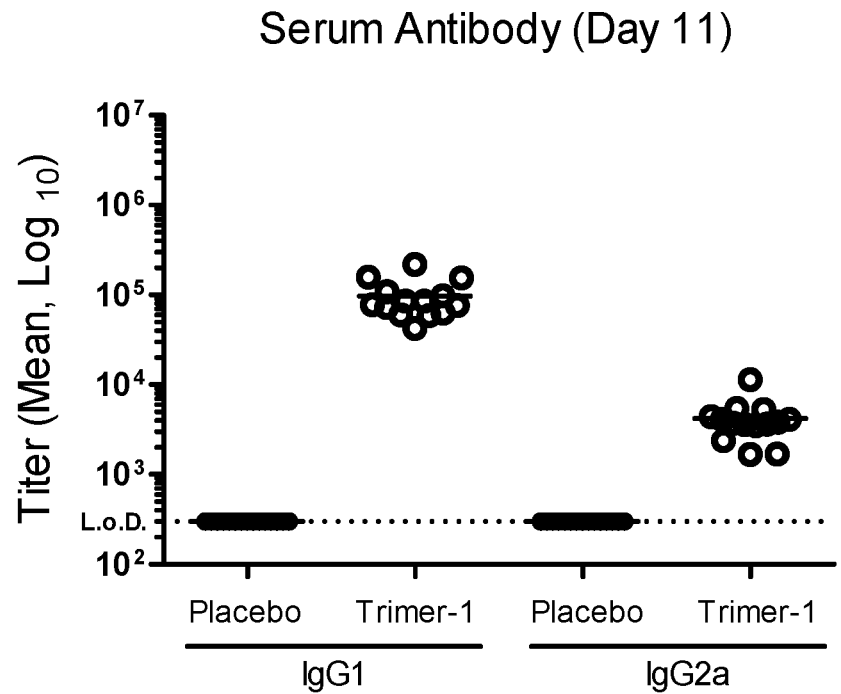
Figure 16B:
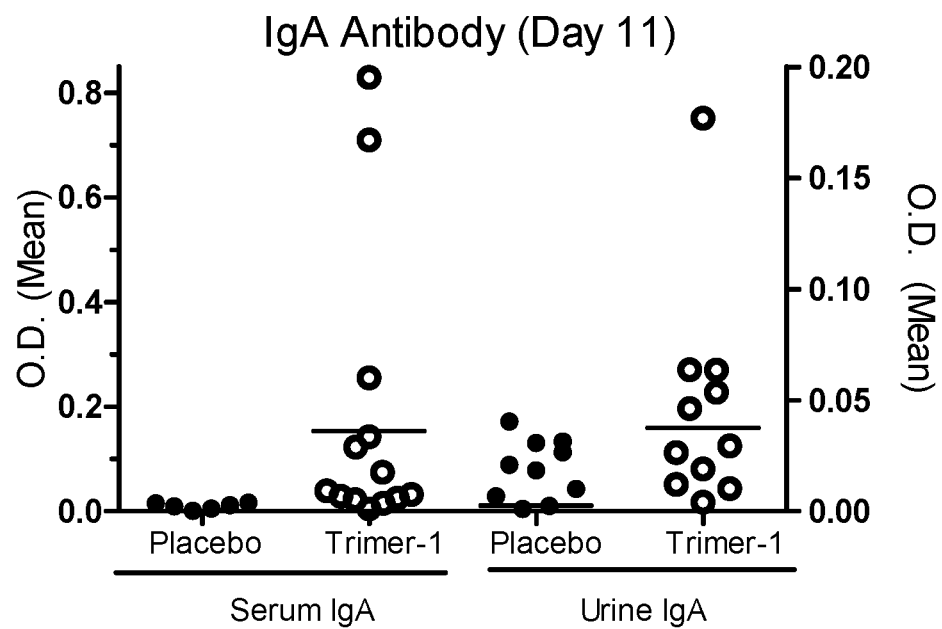

FIGS. 16A-B show antibody measured in the urine and serum. Mice were vaccinated with Trimer-1 as described in FIG. 15. Panel A shows serum IgG1 and IgG2a titers. Panel B shows IgA antibody levels measured in both serum (left Y-axis) and urine (right Y-axis) for mice immunized with Trimer-1. For each group, the level of antibody reactivity was determined against the immunizing antigen. In all cases, mean antibody levels were higher in Trimer-1 vaccinates than placebos, indicating that immunization induced a rapid and robust immune response, while UTI challenge alone did not. (LOD, limit of detection).

Figure 17:
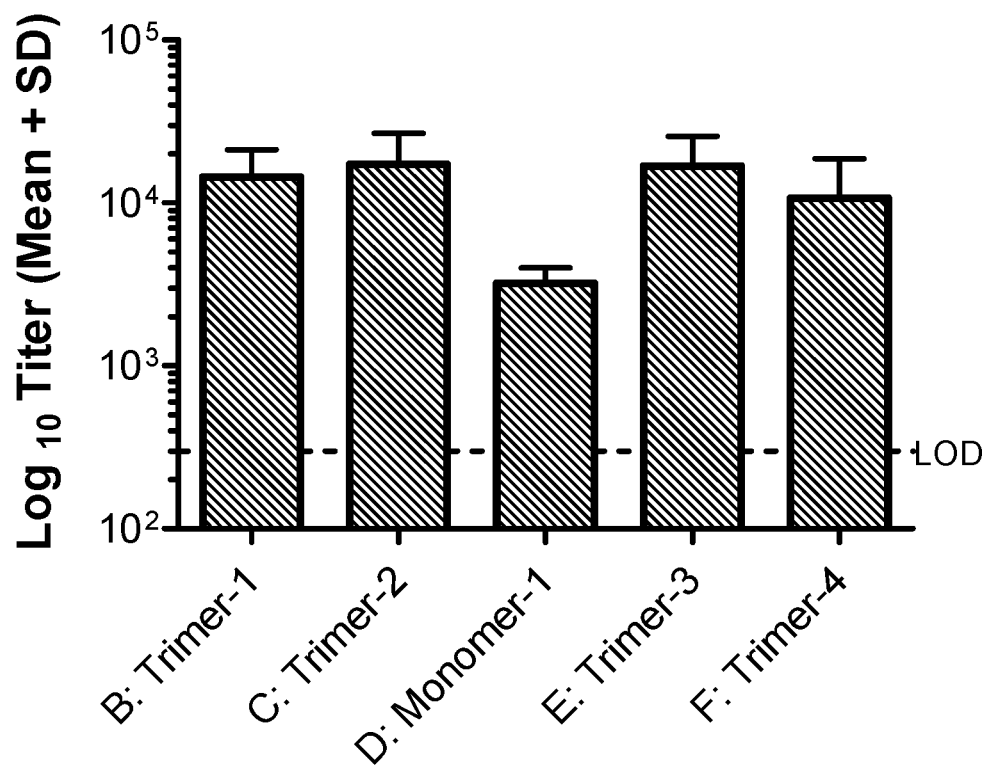

FIG. 17 shows serum IgG titers in mice immunized with Trimer-1, Trimer-2, Monomer-1, Trimer-3 and Trimer-4. Vaccinated mice were immunized SC with 100 µg of antigen followed three weeks later by an IN boost with 50 µg of antigen. For each group, titers were determined against the immunizing antigen. IgG titers did not differ significantly between groups (ANOVA, P>0.05). (LOD, limit of detection).

FIGS. 18A-B show the effect of adjuvant, route, and schedule on Trimer-1 vaccine efficacy against UTI caused by UPEC-25. All IN immunizations were adjuvanted with squalene+dmLT. All ID immunizations were adjuvanted with AlOH+dmLT. Total CFU are shown for the bladder (panel A) and kidney (panel B). The mitigated fraction for the vaccine (B, C, E) compared with the naïve control (A) is indicated where significant (*). Boxed mitigated fraction values indicate the vaccine also achieved a significant prevented fraction when compared with the naïve control (A).

FIGS. 19A-F show the serology for mice immunized with Trimer-1. This includes serum IgG1 and IgG2a titers (panels A, B), the IgG1/IgG2a ratio (panel C), serum IgA (panel D), urine IgG (panel E), and urine IgA (panel F). Mice were immunized as indicated in Table 20. All IN immunizations were adjuvanted with squalene+dmLT. All ID immunizations were adjuvanted with AlOH+dmLT. Antibody levels were determined by ELISA against the immunizing antigen, Trimer-1. Significance between groups is indicated (ANOVA with Tukey's test for multiple comparisons).

FIGS. 20A-D show the effect of adjuvant, route, and schedule on the induction of antigen-responsive T cells, as measured by the release of cytokines after in vitro restimulation of splenocytes with Trimer-1 or a mixture of Trimer-1 T domain peptides for 48 hours. Levels of TNFα (panel A), IL-2 (panel B), IFNγ (panel C), and IL-17A (panel D) were determined in cell supernatants using CBA. The level of significance was determined by ANOVA, with multiple comparisons determined by Tukey's test (*P<0.05; P<0.01; *P<0.001; ****P<0.0001). The level of significance for vaccine groups that differed from the naïve control are indicated directly above the bar. Vaccine groups that differed significantly from each other are indicated with a horizontal bar, and the level of significance is shown above the bar.

FIGS. 21A-D shows the effect of adjuvants, routes, and schedule on Trimer-1 induction of antigen-specific T memory cells, as measured by ICS and flow cytometry after restimulation of splenocytes with Trimer-1 for 8 hours. The cell subset and cytokine are indicated at the top of each plot. The level of significance was determined by ANOVA, with multiple comparisons determined by Tukey's test (*P<0.05; P<0.01; *P<0.001; ****P<0.0001). The level of significance for vaccine groups that differed from the naïve control are indicated directly above the bar. Vaccine groups that differed significantly from each other are indicated with a horizontal bar, and the level of significance is shown above the bar.

Figure 22:
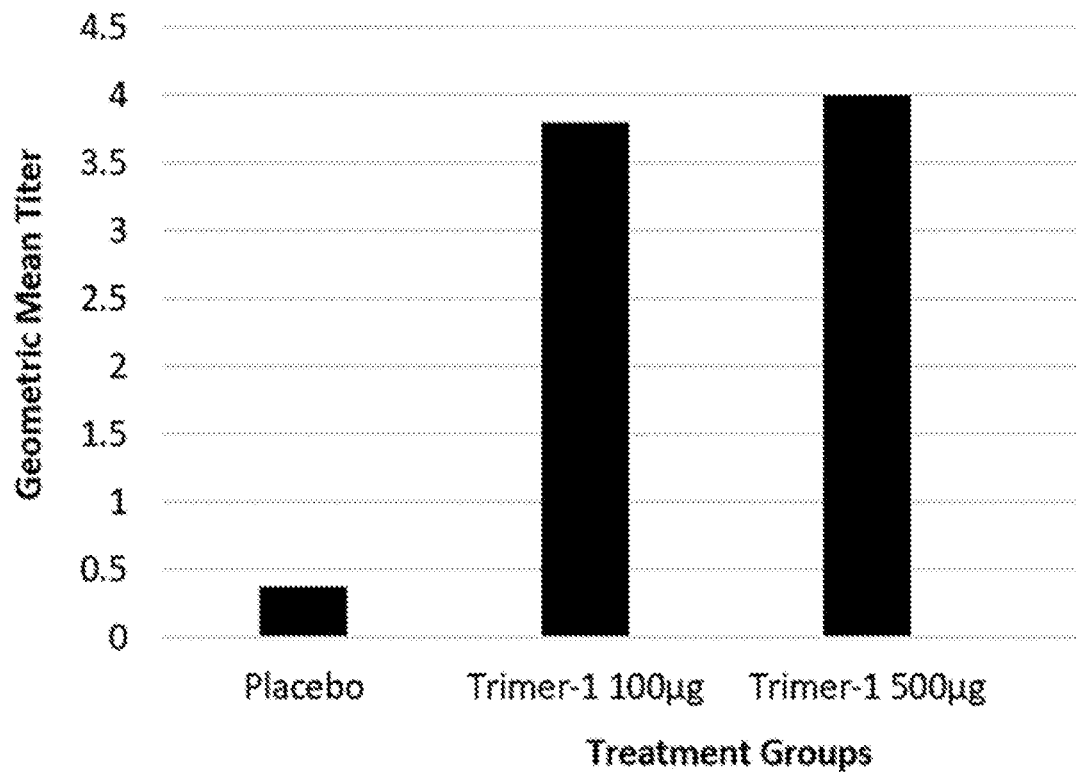

FIG. 22 shows the IgG serological response to vaccination using Trimer-1 in turkeys.

Figure 23:
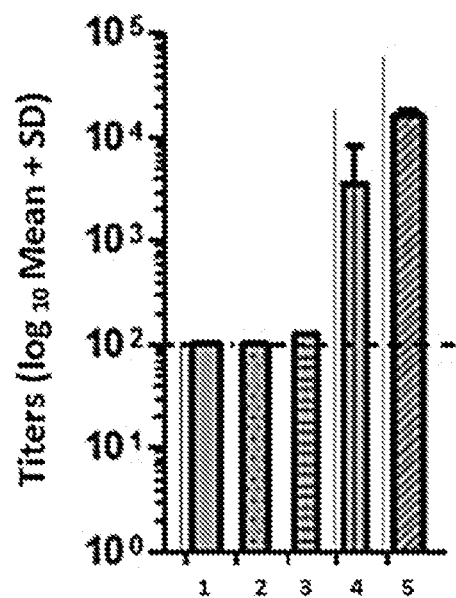

FIG. 23 shows the IgG serological response to vaccination using Trimer-1 in chickens.

FIG. 24 shows the amino acid sequences of different embodiments of proteins described herein, and examples of nucleotide sequences encoding MoLE proteins.

DETAILED DESCRIPTION OF ILLUSTRATIVE EMBODIMENTS

Proteins

Provided herein are proteins having at least two types of domains, a B cell epitope domain and a T cell epitope domain. As used herein, "protein" refers broadly to a polymer of two or more amino acids linked by peptide bonds. Thus, for example, the terms peptide and polypeptide are included within the definition of protein. The term protein does not connote a specific length of a polymer of amino acids. The proteins described herein are made up of modular linked epitopes, and may be referred to herein as MoLE proteins. Optionally, two or more of the domains of a protein described herein are joined by a linker.

In one embodiment, a MoLE protein includes at least one B cell domain selected from FDRDYTTVWGQRAPLYYSPGYGPASLYDYKGRG (SEQ ID NO:12), SQGDDNYGLNLGKGFSAIS-GSSTPYVSKGLNSDRIPGTER (SEQ ID NO:13), and DESLRFYPFPTVNANKQATAFSSSQQDTDQ (SEQ ID NO:14), and at least one T cell domain selected from ESRQLQLITQYYKSQ (SEQ ID NO:15), DPFNI-DHIEVISGAT (SEQ ID NO:16), and VAQQNDDNEIIV-SAS (SEQ ID NO:17). In another embodiment, a MoLE protein includes at least one B cell domain selected from REVKSGKKDKYNHWDLNYESRKP (SEQ ID NO:18), KNNQVHTLTPGESLDAWTMRGNLKQPNSKRETHN-SRS (SEQ ID NO:19), and QEHGKFGNSTT (SEQ ID NO:20), and at least one T cell domain selected from GISITGGNEKPDISI (SEQ ID NO:21) and EKVIREVKSGKKDKY (SEQ ID NO:22).

A MoLE protein includes at least one B cell domain and at least one T cell domain. Exemplary MoLE proteins that include one B cell domain and one T cell domain selected from SEQ ID NOs:12-17 in different orders are identified in Table 1. Exemplary MoLE proteins that include one B cell domain and one T cell domain selected from SEQ ID NOs:18-22 in different orders are identified in Table 2. Tables 1 and 2 shows the order of domains as B cell domain followed by T cell domain; however, the domains can be present in a MoLE protein with a T cell domain followed by a B cell domain. Other embodiments of a MoLE protein described herein include two B cell domains and two T cell domains, three B cell domains and three T cell domains, etc. In one embodiment, the domains are present in a MoLE protein with a B cell domain followed by a T cell domain, for instance, in the order of B cell domain-T cell domain when the MoLE protein includes one copy of each domain, B cell domain-T cell domain-B cell domain-T cell domain when the MoLE protein includes two copies of each domain, or B cell domain-T cell domain-B cell domain-T cell domain-B cell domain-T cell domain when the MoLE protein includes three copies of each domain.

TABLE 1

Examples of MoLE proteins that include one B cell domain and one T cell domain selected from SEQ ID NOs: 12-17.

| MoLE protein: | B cell domain, SEQ ID NO | T cell domain, SEQ ID NO |
|---|---|---|
| 1 | 12 | 15 |
| 2 | 12 | 16 |
| 3 | 12 | 17 |
| 4 | 13 | 15 |
| 5 | 13 | 16 |
| 6 | 13 | 17 |
| 7 | 14 | 15 |
| 8 | 14 | 16 |
| 9 | 14 | 17 |

Each row refers to the order of the domains in a MoLE protein from N-terminal end to C-terminal end. For instance, MoLE protein 1 is the order SEQ ID NO: 12 and 15.

TABLE 2

Examples of MoLE proteins that include one B cell domain and one T cell domain selected from SEQ ID NOs: 18-22.

| MoLE protein: | B cell domain, SEQ ID NO | T cell domain, SEQ ID NO |
|---|---|---|
| 10 | 18 | 20 |
| 11 | 18 | 21 |
| 12 | 19 | 20 |
| 13 | 19 | 21 |
| 14 | 20 | 20 |
| 15 | 20 | 21 |

Each row refers to the order of the domains in a MoLE protein from N-terminal end to C-terminal end. For instance, MoLE protein 10 is the order SEQ ID NO: 18 and 20.

Exemplary MoLE proteins that include three B cell domains and three T cell domains selected from SEQ ID NOs:12-17 in different orders are identified in Table 3. Table 3 shows the order of domains as B cell domain followed by T cell domain; however, the domains can be present in a MoLE protein with a T cell domain followed by a B cell domain. A set of B cell and T cell domains is referred to herein as a module, e.g., each MoLE protein in Tables 1-8 is a module. The set of B cell and T cell domains that includes one copy of each of SEQ ID NOs:12-17 is referred to herein as module I.

TABLE 3

Examples of MoLE proteins that include SEQ ID NOs: 12-17.

| MoLE protein: | B cell domain, SEQ ID NO: 12 | T cell domain, SEQ ID NO: 15 | B cell domain, SEQ ID NO: 13 | T cell domain, SEQ ID NO: 16 | B cell domain, SEQ ID NO: 14 | T cell domain, SEQ ID NO: 17 |
|---|---|---|---|---|---|---|
| 16 | 1 | 2 | 3 | 4 | 5 | 6 |
| 17 | 1 | 2 | 3 | 6 | 5 | 4 |
| 18 | 1 | 4 | 3 | 2 | 5 | 6 |
| 19 | 1 | 6 | 3 | 2 | 5 | 4 |
| 20 | 1 | 4 | 3 | 6 | 5 | 2 |
| 21 | 1 | 6 | 3 | 4 | 5 | 2 |
| 22 | 1 | 2 | 5 | 4 | 3 | 6 |
| 23 | 1 | 2 | 5 | 6 | 3 | 4 |
| 24 | 1 | 4 | 5 | 2 | 3 | 6 |
| 25 | 1 | 6 | 5 | 2 | 3 | 4 |
| 26 | 1 | 4 | 5 | 6 | 3 | 2 |
| 27 | 1 | 6 | 5 | 4 | 3 | 2 |
| 28 | 3 | 2 | 1 | 4 | 5 | 6 |
| 29 | 3 | 2 | 1 | 6 | 5 | 4 |
| 30 | 3 | 4 | 1 | 2 | 5 | 6 |
| 31 | 3 | 6 | 1 | 2 | 5 | 4 |
| 32 | 3 | 4 | 1 | 6 | 5 | 2 |

TABLE 3-continued Examples of MoLE proteins that include SEQ ID NOs: 12-17.

| MoLE protein: | B cell domain, SEQ ID NO: 12 | T cell domain, SEQ ID NO: 15 | B cell domain, SEQ ID NO: 13 | T cell domain, SEQ ID NO: 16 | B cell domain, SEQ ID NO: 14 | T cell domain, SEQ ID NO: 17 |
|---|---|---|---|---|---|---|
| 33 | 3 | 6 | 1 | 4 | 5 | 2 |
| 34 | 3 | 2 | 5 | 4 | 1 | 6 |
| 35 | 3 | 2 | 5 | 6 | 1 | 4 |
| 36 | 3 | 4 | 5 | 2 | 1 | 6 |
| 37 | 3 | 6 | 5 | 2 | 1 | 4 |
| 38 | 3 | 4 | 5 | 6 | 1 | 2 |
| 39 | 3 | 6 | 5 | 4 | 1 | 2 |
| 40 | 5 | 2 | 1 | 4 | 3 | 6 |
| 41 | 5 | 2 | 1 | 6 | 3 | 4 |
| 42 | 5 | 4 | 1 | 2 | 3 | 6 |
| 43 | 5 | 6 | 1 | 2 | 3 | 4 |
| 44 | 5 | 4 | 1 | 6 | 3 | 2 |
| 45 | 5 | 6 | 1 | 4 | 3 | 2 |
| 46 | 5 | 2 | 3 | 4 | 1 | 6 |
| 47 | 5 | 2 | 3 | 6 | 1 | 4 |
| 48 | 5 | 4 | 3 | 2 | 1 | 6 |
| 49 | 5 | 6 | 3 | 2 | 1 | 4 |
| 50 | 5 | 4 | 3 | 6 | 1 | 2 |
| 51 | 5 | 6 | 3 | 4 | 1 | 2 |

Each row refers to the position of the domain in a MoLE protein from N-terminal end to C-terminal end. For instance, MoLE protein 16 is the order SEQ ID NO: 12, 15, 13, 16, 14, and 17.

In another embodiment, exemplary MoLE proteins that include three B cell domains and two T cell domains selected from SEQ ID NOs:18-22 in different orders are identified in Table 4. Table 4 shows the order of domains as B cell domain followed by T cell domain; however, the domains can be present in a MoLE protein with a T cell domain followed by a B cell domain. The set of B cell and T cell domains that includes one copy of each of selected from SEQ ID NOs:18-22 is referred to herein as module II.

TABLE 4

Examples of MoLE proteins that include SEQ ID NOs: 18-22.

| MoLE protein: | B cell domain, SEQ ID NO: 18 | T cell domain, SEQ ID NO: 21 | B cell domain, SEQ ID NO: 19 | T cell domain, SEQ ID NO: 22 | B cell domain, SEQ ID NO: 20 |
|---|---|---|---|---|---|
| 52 | 1 | 2 | 3 | 4 | 5 |
| 53 | 1 | 4 | 3 | 2 | 5 |
| 54 | 1 | 2 | 5 | 4 | 3 |
| 55 | 1 | 4 | 5 | 2 | 3 |
| 56 | 2 | 2 | 1 | 4 | 3 |
| 57 | 2 | 4 | 1 | 2 | 3 |
| 58 | 2 | 2 | 3 | 4 | 1 |
| 59 | 2 | 4 | 3 | 2 | 1 |
| 60 | 3 | 2 | 2 | 4 | 1 |
| 61 | 3 | 4 | 2 | 2 | 1 |
| 62 | 3 | 2 | 1 | 4 | 2 |
| 63 | 3 | 4 | 1 | 2 | 2 |

Each row refers to the position of the domain in a MoLE protein from N-terminal end to C-terminal end. For instance, MoLE protein 1 is the order SEQ ID NO: 18, 21, 19, 22.

In one embodiment, a MoLE protein includes at least one B cell domain selected from SEQ ID NO:12-14, and at least one T cell domain selected from SEQ ID NO:21 and 22. In another embodiment, a MoLE protein includes at least one B cell domain selected from SEQ ID NO:18-20 and at least one T cell domain selected from SEQ ID NO:15-17.

Exemplary MoLE proteins that include one B cell domain selected from SEQ ID NOs:12-14 and one T cell domain selected from SEQ ID NOs:21-22 in different orders are identified in Table 5. Exemplary MoLE proteins that include one B cell domain selected from SEQ ID NOs:18-20 and one T cell domain selected from SEQ ID NOs:15-17 in different orders are identified in Table 6. Tables 5 and 6 shows the order of domains as B cell domain followed by T cell domain; however, the domains can be present in a MoLE protein with a T cell domain followed by a B cell domain.

TABLE 5

Examples of MoLE proteins that include one B cell domain selected from SEQ ID NOs: 12-14 and one T cell domain selected from SEQ ID NOs: 21-22.

| MoLE protein: | B cell domain, SEQ ID NO | T cell domain, SEQ ID NO |
|---|---|---|
| 64 | 12 | 21 |
| 65 | 12 | 22 |
| 66 | 13 | 21 |
| 67 | 13 | 22 |
| 68 | 14 | 21 |
| 69 | 14 | 22 |

Each row refers to the order of the domains in a MoLE protein from N-terminal end to C-terminal end. For instance, MoLE protein 64 is the order SEQ ID NO: 12 and 20.

TABLE 6

Examples of MoLE proteins that include one B cell domain selected from SEQ ID NOs: 18-20 and one T cell domain selected from SEQ ID NOs: 15-17.

| MoLE protein: | B cell domain, SEQ ID NO | T cell domain, SEQ ID NO |
|---|---|---|
| 70 | 18 | 15 |
| 71 | 18 | 16 |
| 72 | 18 | 17 |
| 73 | 19 | 15 |
| 74 | 19 | 16 |
| 75 | 19 | 17 |
| 76 | 20 | 15 |
| 77 | 20 | 16 |
| 78 | 20 | 17 |

Each row refers to the position of the domain in a MoLE protein from N-terminal end to C-terminal end. For instance, MoLE protein 70 is the order SEQ ID NO: 18 and 15.

Exemplary MoLE proteins that include three B cell domains selected from SEQ ID NOs:12-14 and two T cell domains selected from SEQ ID NOs:21-22 in different orders are identified in Table 7. Table 7 shows the order of domains as B cell domain followed by T cell domain; however, the domains can be present in a MoLE protein with a T cell domain followed by a B cell domain.

TABLE 7

Examples of MoLE proteins that include SEQ ID NOs: 12-14 and 21-22.

| MoLE protein: | B cell domain, SEQ ID NO: 12 | T cell domain, SEQ ID NO: 21 | B cell domain, SEQ ID NO: 13 | T cell domain, SEQ ID NO: 22 | B cell domain, SEQ ID NO: 14 |
|---|---|---|---|---|---|
| 79 | 1 | 2 | 3 | 4 | 5 |
| 80 | 1 | 4 | 3 | 2 | 5 |
| 81 | 1 | 2 | 5 | 4 | 3 |
| 82 | 1 | 4 | 5 | 2 | 3 |
| 83 | 2 | 2 | 1 | 4 | 3 |
| 84 | 2 | 4 | 1 | 2 | 3 |
| 85 | 2 | 2 | 3 | 4 | 1 |
| 86 | 2 | 4 | 3 | 2 | 1 |
| 87 | 3 | 2 | 2 | 4 | 1 |
| 88 | 3 | 4 | 2 | 2 | 1 |

TABLE 7-continued

Examples of MoLE proteins that include
SEQ ID NOs: 12-14 and 21-22.

| MoLE protein: | B cell domain, SEQ ID NO: 12 | T cell domain, SEQ ID NO: 21 | B cell domain, SEQ ID NO: 13 | T cell domain, SEQ ID NO: 22 | B cell domain, SEQ ID NO: 14 |
|---|---|---|---|---|---|
| 89 | 3 | 2 | 1 | 4 | 2 |
| 90 | 3 | 4 | 1 | 2 | 2 |

Each row refers to the position of the domain in a MoLE protein from N-terminal end to C-terminal end. For instance, MoLE protein 79 is the order SEQ ID NO: 12, 21, 13, 22, and 14.

Exemplary MoLE proteins that include three B cell domains selected from SEQ ID NOs:18-20 and three T cell domains selected from SEQ ID NOs:15-17 in different orders are identified in Table 8. Table 8 shows the order of domains as B cell domain followed by T cell domain; however, the domains can be present in a MoLE protein with a T cell domain followed by a B cell domain.

TABLE 8

Examples of MoLE proteins that include SEQ
ID NOs: 18-20 and SEQ ID NOs: 15-17.

| MoLE protein: | B cell domain, SEQ ID NO: 18 | T cell domain, SEQ ID NO: 15 | B cell domain, SEQ ID NO: 19 | T cell domain, SEQ ID NO: 16 | B cell domain, SEQ ID NO: 20 | T cell domain, SEQ ID NO: 17 |
|---|---|---|---|---|---|---|
| 91 | 1 | 2 | 3 | 4 | 5 | 6 |
| 92 | 1 | 2 | 3 | 6 | 5 | 4 |
| 93 | 1 | 4 | 3 | 2 | 5 | 6 |
| 94 | 1 | 6 | 3 | 2 | 5 | 4 |
| 95 | 1 | 4 | 3 | 6 | 5 | 2 |
| 96 | 1 | 6 | 3 | 4 | 5 | 2 |
| 97 | 1 | 2 | 5 | 4 | 3 | 6 |
| 98 | 1 | 2 | 5 | 6 | 3 | 4 |
| 99 | 1 | 4 | 5 | 2 | 3 | 6 |
| 100 | 1 | 6 | 5 | 2 | 3 | 4 |
| 101 | 1 | 4 | 5 | 6 | 3 | 2 |
| 102 | 1 | 6 | 5 | 4 | 3 | 2 |
| 103 | 3 | 2 | 1 | 4 | 5 | 6 |
| 104 | 3 | 2 | 1 | 6 | 5 | 4 |
| 105 | 3 | 4 | 1 | 2 | 5 | 6 |
| 106 | 3 | 6 | 1 | 2 | 5 | 4 |
| 107 | 3 | 4 | 1 | 6 | 5 | 2 |
| 108 | 3 | 6 | 1 | 4 | 5 | 2 |
| 109 | 3 | 2 | 5 | 4 | 1 | 6 |
| 110 | 3 | 2 | 5 | 6 | 1 | 4 |
| 111 | 3 | 4 | 5 | 2 | 1 | 6 |
| 112 | 3 | 6 | 5 | 2 | 1 | 4 |
| 113 | 3 | 4 | 5 | 6 | 1 | 2 |
| 114 | 3 | 6 | 5 | 4 | 1 | 2 |
| 115 | 5 | 2 | 1 | 4 | 3 | 6 |
| 116 | 5 | 2 | 1 | 6 | 3 | 4 |
| 117 | 5 | 4 | 1 | 2 | 3 | 6 |
| 118 | 5 | 6 | 1 | 2 | 3 | 4 |
| 119 | 5 | 4 | 1 | 6 | 3 | 2 |
| 120 | 5 | 6 | 1 | 4 | 3 | 2 |
| 121 | 5 | 2 | 3 | 4 | 1 | 6 |
| 122 | 5 | 2 | 3 | 6 | 1 | 4 |
| 123 | 5 | 4 | 3 | 2 | 1 | 6 |
| 124 | 5 | 6 | 3 | 2 | 1 | 4 |
| 125 | 5 | 4 | 3 | 6 | 1 | 2 |
| 126 | 5 | 6 | 3 | 4 | 1 | 2 |

Each row refers to the position of the domain in a MoLE protein from N-terminal end to C-terminal end. For instance, MoLE protein 91 is the order SEQ ID NO: 18, 15, 19, 16, 20, and 17.

A MoLE protein can further include tandem repeats of a module, for instance, at least 1, at least 2, at least 3, at least 4, at least 5, at least 6, at least 7, at least 8, at least 9, or at least 10 tandem repeats. In one embodiment, a MoLE protein has no greater than 11 tandem repeats of a module. For instance, when the MoLE protein includes one copy of each type of domain (B cell domain-T cell domain, such as SEQ ID NO:12 and 15), a MoLE protein with tandem repeats can include, but is not limited to, an amino acid sequence SEQ ID NO:12-15-12-15 (two tandem repeats), or SEQ ID NO:12-15-12-15-12-15 (three tandem repeats). In another example, when the MoLE protein includes two copies of each type of domain (B cell domain-T cell domain-B cell domain-T cell domain, such as SEQ ID NO:12-15-13-16), a MoLE protein with tandem repeats can include, but is not limited to, an amino acid sequence SEQ ID NO:12-15-13-16-12-15-13-16 (two tandem repeats). In yet another example, when the MoLE protein includes module I or module II present as tandem repeats, a MoLE protein with tandem repeats can be, but is not limited to, at least two copies of module I, or at least two copies of module II.

Examples of MoLE proteins disclosed in Table 3 as MoLE protein 16 include, but are not limited to, SEQ ID NOs:1, 3, 5, and amino acids 7-518 of SEQ ID NO:8 (see FIG. 15). In one embodiment, a MoLE protein disclosed in Table 3 as MoLE protein 16 includes a 6-His tag at the N-terminal end (SEQ ID NO:8, also referred to herein as Trimer-1). The MoLE protein at SEQ ID NO:3 includes one copy of module I, where each B cell and T cell domain is optionally joined by a linker. The MoLE protein at SEQ ID NO:5 includes three copies of module I (a trimer), where each B cell and T cell domain is optionally joined by a linker, and each copy of module I is also optionally joined by a linker.

Figure 18:
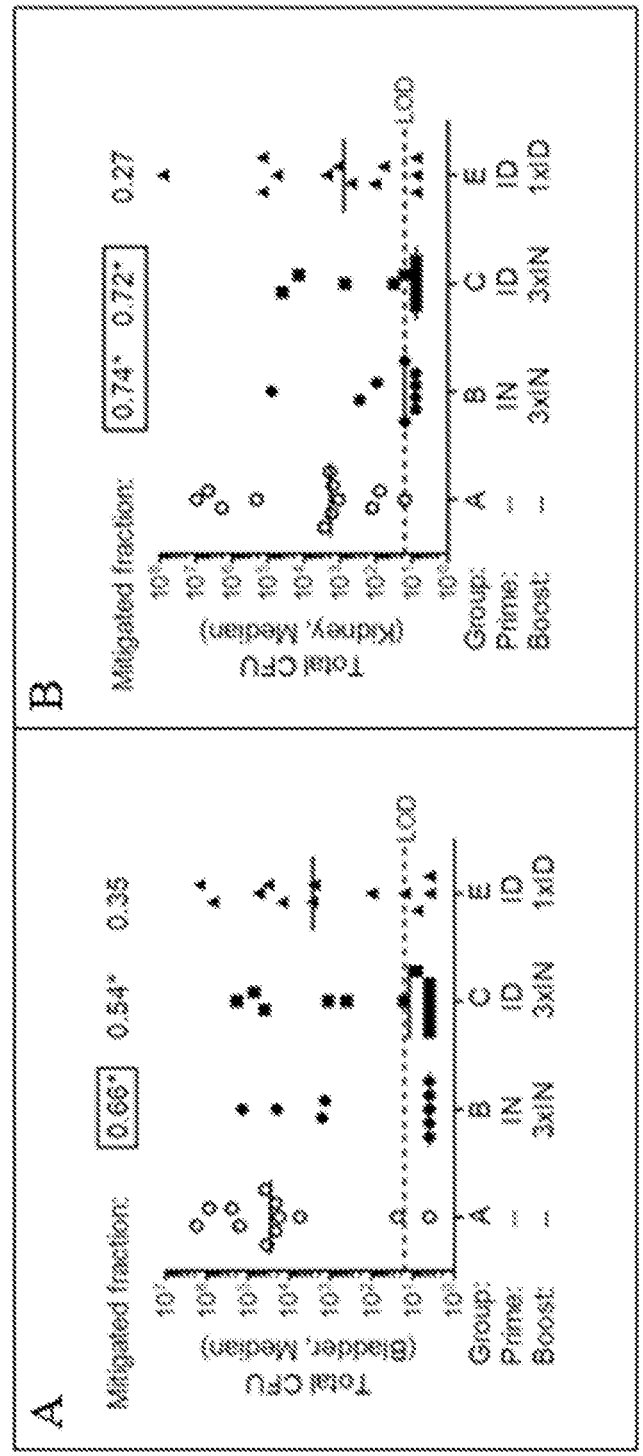

Examples of MoLE proteins disclosed in Table 4 as MoLE protein 52 include, but are not limited to, SEQ ID NOs:2, 4, 6, and amino acids 7-365 of SEQ ID NO:10 (see FIG. 18). In one embodiment, a MoLE protein disclosed in Table 4 as MoLE protein 52 includes a 6-His tag at the N-terminal end (SEQ ID NO:10, also referred to herein as Trimer-2). The MoLE protein at SEQ ID NO:4 includes one copy of module II, where each B cell and T cell domain is optionally joined by a linker X. The MoLE protein at SEQ ID NO:6 includes three copies of module II, where each B cell and T cell domain is optionally joined by a linker, and each copy of module II is also optionally joined by a linker.

In one embodiment, a MoLE protein described herein includes a linker between the B cell and T cell domains. A linker is an amino acid sequence that joins protein domains in a fusion protein. A linker can be flexible or rigid, and in one embodiment is flexible. In one embodiment, a linker can be at least 3, at least 4, at least 5, or at least 6 amino acids in length. It is expected that there is no upper limit on the length of a linker used in a fusion protein described herein; however, in one embodiment, a linker is no greater than 10, no greater than 9, no greater than 8, or no greater than 7 amino acids in length. Many linkers are known to a skilled person (see Chen et al. 2013, Adv, Drug Deliv. Rev., 65(10):1357-1369). Specific examples of linkers include, but are not limited to, GSGS (SEQ ID NO:23) and GPGPG (SEQ ID NO:24). A MoLE protein can include more than one type of linker. For instance, in a MoLE protein some linkers can be GSGS (SEQ ID NO:23) and others can be GPGPG (SEQ ID NO:24).

Proteins described herein have immunological activity. "Immunological activity" refers to the ability of a protein to elicit an immunological response in an animal. An immunological response to a protein is the development in an animal of a cellular and/or antibody-mediated immune response to the protein. Usually, an immunological response includes but is not limited to one or more of the following effects: the production of antibodies, B cells, helper T cells, suppressor T cells, and/or cytotoxic T cells, directed to an epitope or epitopes of the protein. "Epitope" refers to the site on an antigen to which specific B cells and/or T cells respond so that antibody is produced. The immunological activity may be protective. "Protective immunological activity" refers to the ability of a protein to elicit an immunological response in an animal that prevents or inhibits infection by a gram-negative microbe, such as *E. coli*. In one embodiment, the *E. coli* strain CFT073 (ATCC® 700928™) is used to evaluate protective immunological activity. Whether a protein has protective immunological activity can be determined by methods known in the art such as, for example, methods described in Examples 12-32. For example, a protein described herein, or combination of proteins described herein, protects an animal against challenge with a gram-negative microbe, such as *E. coli*. A protein described herein may have seroactive activity. "Seroactive activity" refers to the ability of a protein to react with antibody present in convalescent serum from an animal infected with a gram-negative microbe, such as *E. coli*. A protein described herein may have immunoregulatory activity. "Immunoregulatory activity" refers to the ability of a protein to act in a nonspecific manner to enhance an immune response to a particular antigen. Methods for determining whether a protein has immunoregulatory activity are known in the art.

A MoLE protein may be "structurally similar" to a reference protein if the amino acid sequence of the MoLE protein possesses a specified amount of sequence similarity and/or sequence identity compared to the reference protein. Thus, a protein may be "structurally similar" to a reference protein if, compared to the reference protein, it possesses a sufficient level of amino acid sequence identity, amino acid sequence similarity, or a combination thereof.

A reference protein can be any protein disclosed herein, including the proteins listed in Tables 1-8. In one embodiment, a reference protein is module I (e.g., SEQ ID NO:1) or module II (e.g., SEQ ID NO:2). A reference protein can include tandem repeats of any protein disclosed herein, including the proteins listed in Tables 1-8. In another embodiment, a reference protein includes tandem repeats of module I or tandem repeats of module II. In another embodiment, a reference protein is module I or module II that includes one or more linker (e.g., any MoLE protein disclosed in Table 3 or 4 where there is a linker between domains), or tandem repeats of module I or module II that includes one or more linker. In some embodiments when a reference protein includes one or more linker, the one or more linker is not considered when determining whether a protein is structurally similar to a reference protein. In another embodiment, a reference protein is SEQ ID NO:5, 6, 8, or 10.

A B cell domain and a T cell domain may be "structurally similar" to a reference domain if the amino acid sequence of the domain possesses a specified amount of sequence similarity and/or sequence identity compared to the reference domain. Thus, a domain may be "structurally similar" to a reference domain if, compared to the reference domain, it possesses a sufficient level of amino acid sequence identity, amino acid sequence similarity, or a combination thereof. A B cell domain that is structurally similar to a reference B cell domain has B cell activity. A T cell domain that is structurally similar to a reference T cell domain has T cell activity. Examples of reference B cell domains are SEQ ID NOs:12, 13, 14, 18, 19, and 20. Examples of reference T cell domains are SEQ ID NOs:15, 16, 17, 21, and 22.

Protein Sequence Similarity and Protein Sequence Identity

Structural similarity of two proteins can be determined by aligning the residues of the two proteins (for example, a candidate protein and any appropriate reference protein described herein) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate protein is the protein being compared to the reference protein. A candidate protein can be isolated, for example, from a microbe engineered to produce the candidate protein using recombinant techniques, or chemically or enzymatically synthesized.

Structural similarity of two domains can be determined by aligning the residues of the two domains (for example, a candidate domain and any appropriate reference domain described herein) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate domain is the domain being compared to the reference domain. A candidate domain can be isolated, for example, from a microbe engineered to produce the candidate domain using recombinant techniques, or chemically or enzymatically synthesized.

Unless modified as otherwise described herein, a pairwise comparison analysis of amino acid sequences can be carried out using the BESTFIT algorithm in the GCG package (version 10.2, Madison Wis.). Alternatively, amino acid sequences may be compared using the Blastp program of the BLAST 2 search algorithm, as described by Tatiana et al. (*FEMS Microbiol Lett,* 174:247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in a protein may be selected from other members of the class to which the amino acid belongs. For example, it is well-known in the art of protein biochemistry that an amino acid belonging to a grouping of amino acids having a particular size or characteristic (such as charge, hydrophobicity, or hydrophilicity) can be substituted for another amino acid without altering the activity of a protein. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Thus, conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH$_2$.

Thus, as used herein, reference to a protein as described herein and/or reference to the amino acid sequence of one or more SEQ ID NOs can include a protein with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to the reference amino acid sequence.

Alternatively, as used herein, reference to a protein as described herein and/or reference to the amino acid sequence of one or more SEQ ID NOs can include a protein with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference amino acid sequence.

A MoLE protein that is structurally similar to a reference protein has immunological activity (including protective immunological activity, seroactive activity, and/or immunoregulatory activity). A B cell domain that is structurally similar to a reference B cell domain has B cell activity, and a T cell domain that is structurally similar to a reference T cell domain has T cell activity. A candidate B cell domain has B cell activity if antibody produced by immunizing an animal with the candidate B cell domain specifically binds to the reference B cell domain. A candidate T cell domain has T cell activity if cells from a mouse immunized with the candidate T cell are stimulated to produce cytokines when exposed to the reference T cell domain.

A protein as described herein also can be designed to include one or more additional sequences such as, for example, the addition of C-terminal and/or N-terminal amino acids. In one embodiment, additional amino acids may facilitate purification by trapping on columns or use of antibodies. Such additional amino acids include, for example, histidine-rich tags that allow purification of proteins on nickel columns. In one embodiment, additional amino acids are those that may signal for acylation or promote mucosal uptake. Such gene modification techniques and suitable additional sequences are well known in the molecular biology arts.

A protein described herein can include one or more modifications. A "modification" of a protein includes a protein that is chemically or enzymatically derivatized at one or more constituent amino acids. Such a modification can include, for example, a side chain modification, a backbone modification, an N-terminal modification, and/or a C-terminal modification such as, for example, acetylation, hydroxylation, methylation, amidation, and the attachment of a carbohydrate and/or lipid moiety, a cofactor, and the like, and combinations thereof. Modified proteins as described herein may retain the biological activity—such as, for example, immunological activity—of the unmodified protein or may exhibit a reduced or increased biological activity compared to the unmodified protein.

Polynucleotides

A protein described herein also may be identified in terms of the polynucleotide that encodes the protein. Thus, this disclosure provides polynucleotides that encode a protein as described herein or hybridize, under standard hybridization conditions, to a polynucleotide that encodes a protein as described herein, and the complements of such polynucleotide sequences.

As used herein, reference to a polynucleotide as described herein and/or reference to the nucleic acid sequence of one or more SEQ ID NOs can include polynucleotides having a sequence identity of at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an identified reference polynucleotide sequence.

In this context, "sequence identity" refers to the identity between two polynucleotide sequences. Sequence identity is generally determined by aligning the bases of the two polynucleotides, for example, aligning the nucleotide sequence of the candidate sequence and a nucleotide sequence that includes a nucleotide sequence disclosed herein, such as nucleotides 19-1569 of SEQ ID NO:7 (which encode an example of module I) or nucleotides 19-1110 of SEQ ID NO:9 (which encode an example of module II) to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate sequence is the sequence being compared to a known sequence—e.g., a nucleotide sequence that includes a nucleotide sequence described herein, for example, nucleotides 19-1569 of SEQ ID NO:7 or nucleotides 19-1110 of SEQ ID NO:9. For example, two polynucleotide sequences can be compared using the Blastn program of the BLAST 2 search algorithm, as described by Tatusova et al., (*FEMS Microbiol Lett.*, 174:247-250 (1999)), and available on the world wide web at ncbi.nlm.nih.gov/BLAST/. The default values for all BLAST 2 search parameters may be used, including reward for match=1, penalty for mismatch=-2, open gap penalty=5, extension gap penalty=2, gap x_dropoff=50, expect=10, wordsize=11, and filter on.

Finally, a polynucleotide can include any polynucleotide that encodes a protein as described herein. Thus, the nucleotide sequence of the polynucleotide may be deduced from the amino acid sequence that is to be encoded by the polynucleotide.

Compositions

A composition as described herein may include at least one protein described herein, or a number of proteins that is an integer greater than one (e.g., at least two, at least three, and so on), in any combination. Unless a specific level of sequence similarity and/or identity is expressly indicated herein (e.g., at least 80% sequence similarity, at least 85% sequence similarity, at least 90% sequence identity, etc.), reference to the amino acid sequence of an identified SEQ ID NO includes variants having the levels of sequence similarity and/or the levels of sequence identity described herein.

A recombinantly-produced protein may be expressed from a vector that permits expression of the protein when the vector is introduced into an appropriate host cell. A host cell may be constructed to produce one or more proteins described herein and, therefore can include one or more vectors that include at least one polynucleotide encoding a protein described herein. Thus, each vector can include one or more polynucleotides as described herein—i.e., a polynucleotide that encodes a protein as described herein. Examples of host cells include, but are not limited to, *E. coli*.

Optionally, a protein described herein can be covalently bound to a carrier protein to improve the immunological properties of the protein. Useful carrier proteins are known in the art, and include, for instance, cholera toxin subunit B and mutant heat labile enterotoxin. The chemical coupling of a protein described herein can be carried out using known and routine methods. For instance, various homobifunctional and/or heterobifunctional cross-linker reagents such as bis(sulfosuccinimidyl) suberate, bis(diazobenzidine), dimethyl adipimidate, dimethyl pimelimidate, dimethyl superimidate, disuccinimidyl suberate, glutaraldehyde, m-maleimidobenzoyl-N-hydroxy succinimide, sulfo-m-maleimidobenzoyl-N-hydroxysuccinimide, sulfosuccinimidyl 4-(N-maleimidomethyl) cycloheane-1-carboxylate, sulfosuccinimidyl 4-(p-maleimido-phenyl) butyrate and (1-ethyl-3-(dimethyl-aminopropyl) carbodiimide can be used (Harlow and Lane, Antibodies, A Laboratory Manual, generally and Chapter 5, Cold Spring Harbor Laboratory, Cold Spring Harbor, New York, N.Y. (1988)).

A composition described herein optionally further includes a pharmaceutically acceptable carrier. "Pharmaceutically acceptable" refers to a diluent, carrier, excipient, salt, etc., that is compatible with the other ingredients of the composition, and not deleterious to the recipient thereof. Typically, the composition includes a pharmaceutically acceptable carrier when the composition is used as described herein. Exemplary pharmaceutically acceptable carriers include buffer solutions and generally exclude blood products such as, for example, whole blood and/or plasma. The compositions as described herein may be formulated in pharmaceutical preparations in a variety of forms adapted to the chosen route of administration, including routes suitable for stimulating an immune response to an antigen. Thus, a composition as described herein can be administered via known routes including, for example, oral; parenteral including intradermal, transcutaneous and subcutaneous, intramuscular, intravenous, intraperitoneal, etc.; and topically, such as, intranasal, intrapulmonary, intramammary, intravaginal, intrauterine, intradermal, transcutaneous and rectally, etc. It is foreseen that a composition can be administered to a mucosal surface, such as by administration to the nasal or respiratory mucosa (e.g., via a spray or aerosol), in order to stimulate mucosal immunity, such as production of secretory IgA antibodies, throughout the animal's body.

A composition as described herein can also be administered via a sustained or delayed release implant. Implants suitable for use are known and include, for example, those disclosed in International Publication No. WO 2001/037810 and/or International Publication No. WO 1996/001620. Implants can be produced at sizes small enough to be administered by aerosol or spray. Implants also can include nanospheres and microspheres.

A composition is administered in an amount sufficient to provide an immunological response to a protein described herein. The amount of protein present in a composition can vary. For instance, the dosage of protein can be between 0.01 micrograms (μg) and 3000 milligrams (mg), typically between 10 μg and 2000 ug. For an injectable composition (e.g. subcutaneous, intramuscular, etc.) the protein can be present in the composition in an amount such that the total volume of the composition administered is 0.5 ml to 5.0 ml, typically 1.0-3.0 ml. The amount administered will vary depending on various factors including, but not limited to, the specific proteins or cells chosen, the weight, physical condition and age of the animal, and the route of administration. Thus, the absolute weight of the protein included in a given unit dosage form can vary, and depends upon factors such as the species, age, weight and physical condition of the animal, as well as the method of administration. Such factors can be determined by one skilled in the art.

The formulations may be conveniently presented in unit dosage form and may be prepared by methods well known in the art of pharmacy. All methods of preparing a composition including a pharmaceutically acceptable carrier include the step of bringing the active compound (e.g., a protein described herein) into association with a carrier that constitutes one or more accessory ingredients. In general, the formulations are prepared by uniformly and intimately bringing the active compound into association with, for instance, a liquid carrier, a finely divided solid carrier, or both, and then, if necessary, shaping the product into the desired formulations.

A composition including a pharmaceutically acceptable carrier can also include an adjuvant. An "adjuvant" refers to an agent that can act in a nonspecific manner to enhance an immune response to a particular antigen, thus potentially reducing the quantity of antigen necessary in any given immunizing composition, and/or the frequency of injection necessary in order to generate an adequate immune response to the antigen of interest. Adjuvants may include, for example, IL-1, IL-2, emulsifiers, muramyl dipeptides, dimethyldiocradecylammonium bromide (DDA), avridine, aluminum hydroxide, oils, saponins, alpha-tocopherol, polysaccharides, emulsified paraffins (available from under the tradename EMULSIGEN from MVP Laboratories, Ralston, Nebr.), ISA-70, RIBI and other substances known in the art.

In another embodiment, a composition can include a biological response modifier, such as, for example, IL-2, IL-4 and/or IL-6, TNF, IFN-alpha, IFN-gamma, and other cytokines that effect immune cells. A composition can also include an antibiotic, preservative, anti-oxidant, chelating agent, etc. Such components are known in the art.

Methods of Use

Also provided are methods of using the compositions described herein. The methods include administering to an animal an effective amount of a composition described herein. As used herein, an "effective amount" of a composition described herein is the amount able to elicit the desired response in the recipient. The composition can be administered at a time that maternal antibody may be present, for instance, as early as one day of age, or at a later time during the life of the animal. The animal can be, for instance, avian (including, for instance, chickens or turkeys), bovine (including, for instance, cattle), caprine (including, for instance, goats), ovine (including, for instance, sheep), porcine (including, for instance, swine), bison (including, for instance, buffalo), equine (including, for instance, horses), a companion animal (including, for instance, a dog or a cat), members of the family Cervidae (including, for instance, deer, elk, moose, caribou and reindeer), or a human. Examples of companion animals include dogs and cats. In one embodiment, an animal is a mouse. In one embodiment, an animal is a hooved animal.

The methods described herein refer to gram-negative microbes. As used herein, a gram-negative microbe includes, but is not limited to, members of the family Vibrionaceae (including, for instance, *Vibrio cholerae*), *Campylobacter* spp. (including, for instance, *C. jejuni*), members of the family Enterobacteriaceae (including, for instance, *Klebsiella* spp., *E. coli*, *Shigella* spp., *Salmonella* spp., *Proteus* spp., *Serratia* spp., and *Yersinia* spp.), members of the family Pasteurellaceae, preferably *Pasteurella* spp. (including, for instance, *P. multocida* and *P. haemolytica*), and members of the family Pseudomonadaceae, preferably *Pseudomonas* spp., (including, for instance, *Pseudomonas aeruginosa*). Examples of *Klebsiella* spp. include *K. pneumoniae* and *K. oxytoca*. Examples of *Salmonella* spp. include *Salmonella enterica* serovars Bredeney, Dublin, Agona, Blockley, Enteriditis, Typhimurium, Hadar, Heidelberg, Montevideo, Muenster, Newport senftenberg, *Salmonella cholerasuis*, and *S. typhi*. Examples of strains of *E. coli* include, for example, *E. coli* serotypes O1a, O2a, O78, and O157; different O:H serotypes including 0104, 0111, 026, 0113, 091; hemolytic strains of enterotoxigenic *E. coli* such as K88$^+$, F4$^+$, F18ab$^+$, and F18ac$^+$; enteropathogenic (EPEC), enterohemorrhagic (EHEC), enteroinvasive (EIEC) and enteroaggregative (EAEC) strains of *E. coli*; and *E. coli* able to cause extra-intestinal infections, such as uropathogenic strains. In one embodiment, the gram-negative microbe is a pathogenic microbe.

In some embodiments, a method may further include additional administrations (e.g., one or more booster administrations) of the composition to the animal to enhance or stimulate a secondary immune response. A booster can be administered at a time after the first administration, for instance, one to eight weeks, preferably two to four weeks, after the first administration of the composition. Subsequent boosters can be administered one, two, three, four, or more times annually. Without intending to be limited by theory, it is expected that in some embodiments annual boosters will not be necessary, as an animal will be challenged in the field by exposure to microbes expressing proteins having epitopes that are structurally related to epitopes present on proteins of the composition administered to the animal.

In one embodiment, a method includes making antibody to a protein described herein, for instance by inducing the production of antibody in an animal, or by recombinant techniques. The antibody produced includes antibody that specifically binds at least one protein present in the composition. In this embodiment, an "effective amount" is an amount effective to result in the production of antibody in the animal. Methods for determining whether an animal has produced antibodies that specifically bind a protein present in a composition of described herein can be determined using routine methods. Also provided is antibody that specifically binds to a protein described herein, and compositions including such antibodies.

As used herein, an antibody that can "specifically bind" a protein is an antibody that interacts with the epitope of the antigen that induced the synthesis of the antibody, or interacts with a structurally related epitope. At least some of the epitopes present in the proteins described herein are epitopes that are conserved in the proteins of different species and different genera of microbes. Accordingly, antibody produced using a protein described herein is expected to bind to proteins expressed by more than one species of microbe, and provide broad spectrum protection against gram-negative microbes.

In one embodiment, a method includes treating an infection in an animal, caused by a gram-negative microbe. As used herein, the term "infection" refers to the presence of a gram-negative microbe in an animal's body, which may or may not be clinically apparent. Treating an infection can be prophylactic or, alternatively, can be initiated after the animal is infected by the microbe. Treatment that is prophylactic—e.g., initiated before a subject is infected by a microbe or while any infection remains subclinical—is referred to herein as treatment of a subject that is "at risk" of infection. As used herein, the term "at risk" refers to an animal that may or may not actually possess the described risk. Thus, typically, an animal "at risk" of infection by a microbe is an animal present in an area where animals have been identified as infected by the microbe and/or is likely to be exposed to the microbe even if the animal has not yet manifested any detectable indication of infection by the microbe and regardless of whether the animal may harbor a subclinical amount of the microbe. Accordingly, administration of a composition can be performed before, during, or after the animal has first contact with the microbe. Treatment initiated after the animal's first contact with the microbe may result in decreasing the severity of symptoms and/or clinical signs of infection by the microbe, completely removing the microbe, and/or decreasing the likelihood of experiencing a clinically evident infection compared to an animal to which the composition is not administered. The method includes administering an effective amount of a composition described herein to an animal having, or at risk of having, an infection caused by a gram-negative microbe, and determining whether the number of microbes causing the infection has decreased. In this embodiment, an "effective amount" is an amount effective to reduce the number of the specified microbes in an animal or reduce the likelihood that the animal experiences a clinically-evident infection compared to an animal to which the composition is not administered. Methods for determining whether an infection is caused by a gram-negative microbe are routine and known in the art, as are methods for determining whether the infection has decreased. The successful treatment of a gram-negative microbial infection in an animal is disclosed in Examples 12-32, which demonstrates the protection against disease caused by *E. coli* in a mouse model by administering a composition described herein. This mouse model is a commonly accepted model for the study of disease caused by *E. coli*.

In another embodiment, a method includes treating one or more symptoms or clinical signs of certain conditions in an animal that may be caused by infection by a gram-negative microbe. The method includes administering an effective amount of a composition described herein to an animal having or at risk of having a condition, or exhibiting symptoms and/or clinical signs of a condition, and determining whether at least one symptom and/or clinical sign of the condition is changed, preferably, reduced. In one embodiment, the animal has a condition caused by an enteropathogenic (EPEC), enterohemorrhagic (EHEC), enterotoxigenic (ETEC), enteroinvasive (EIEC) and/or enteroaggregative (EAEC) strain of *E. coli*. Symptoms and/or clinical signs caused by a gram-negative microbial infection are known to the person skilled in the art. Examples of symptoms and/or clinical signs include, but are not limited to, sepsis; endotoxic shock; osteomyelitis; pneumonia; peritonitis; endocarditis; wound infection; reactive arthritis, meningitis, urinary tract infections (UTI), kidney failure, Guillian-Barre, Reiter syndrome, enteric diarrheal disease and other extra-intestinal diseases. Examples of conditions include, but are not limited to, mastitis, fecal shedding of a microbe, metritis, strangles, intrauterine infections, odema disease, enteritis, chronic reproductive infections, and laminitis.

Treatment of symptoms and/or clinical signs associated with conditions caused by infection by a gram-negative microbe can be prophylactic or, alternatively, can be initiated after the development of a condition described herein. As used herein, the term "symptom" refers to subjective evidence of a disease or condition experienced by the patient and caused by infection by a microbe. As used herein, the term "clinical sign" or, simply, "sign" refers to objective evidence of disease or condition caused by infection by a microbe. Symptoms and/or clinical signs associated with conditions referred to herein and the evaluations of such symptoms are routine and known in the art. Treatment that is prophylactic, for instance, initiated before a subject manifests symptoms or signs of a condition caused by a microbe, is referred to herein as treatment of a subject that is "at risk" of developing the condition. Thus, typically, an animal "at risk" of developing a condition is an animal present in an area where animals having the condition have been diagnosed and/or is likely to be exposed to a microbe causing the condition even if the animal has not yet manifested symptoms or signs of any condition caused by the microbe. Accordingly, administration of a composition can be performed before, during, or after the occurrence of the conditions described herein. Treatment initiated after the development of a condition may result in decreasing the severity of the symptoms or signs of one of the conditions, or completely removing the symptoms or signs. In this embodiment, an "effective amount" is an amount effective to prevent the manifestation of symptoms or signs of a disease, decrease the severity of the symptoms or signs of a disease, and/or completely remove the symptoms or signs.

Also provided is a method for decreasing colonization by a gram-negative microbe, for instance blocking the attachment sites of a gram-negative microbe, including tissues of the skeletal system (for instance, bones, cartilage, tendons and ligaments), muscular system, (for instance, skeletal and smooth muscles), circulatory system (for instance, heart, blood vessels, capillaries and blood), nervous system (for instance, brain, spinal cord, and peripheral nerves), respiratory system (for instance, nose, trachea lungs, bronchi, bronchioles, alveoli), digestive system (for instance, mouth, salivary glands, esophagus, liver, stomach, large and small intestine), excretory system (for instance, kidney, ureter, bladder, and urethra), endocrine system (for instance, hypothalamus, pituitary, thyroid, pancreas and adrenal glands), reproductive system (for instance, ovaries, oviduct, uterus, vagina, mammary glands, testes, and seminal vesicles), lymphatic/immune systems (for instance, lymph, lymph nodes and vessels, mononuclear or white blood cells, such as macrophages, neutrophils, monocytes, eosinophils, basophils, and lymphocytes, including T cells and B cells), and specific cell lineages (for instance, precursor cells, epithelial cells, stem cells), and the like.

Decreasing colonization in an animal may be performed prophylactically or, alternatively, can be initiated after the animal is colonized by the microbe. Treatment that is prophylactic—e.g., initiated before a subject is colonized by a microbe or while any colonization remains undetected—is referred to herein as treatment of a subject that is "at risk" of colonization by the microbe. Thus, typically, an animal "at risk" of colonization by a microbe is an animal present in an area where animals have been identified as colonized by the microbe and/or is likely to be exposed to the microbe even if the animal has not yet manifested any detectable indication of colonization by the microbe and regardless of whether the animal may harbor a sub-colonization number of the microbe. Accordingly, administration of a composition can be performed before, during, or after the animal has first contact with the microbe. Treatment initiated after the animal's first contact with the microbe may result in decreasing the extent of colonization by the microbe, completely removing the microbe, and/or decreasing the likelihood that the animal becomes colonized by the microbe compared to an animal to which the composition is not administered. Thus, the method includes administering an effective amount of a composition described herein to an animal colonized by, or at risk of being colonized by, a gram-negative microbe. In this embodiment, an "effective amount" is an amount sufficient to decrease colonization of the animal by the microbe, where decreasing colonization refers to one or more of: decreasing the extent of colonization by the microbe, completely removing the microbe, and/or decreasing the likelihood that the animal becomes colonized by the microbe compared to an animal to which the composition is not administered. Methods for evaluating the colonization of an animal by a microbe are routine and known in the art. For instance, colonization of an animal's intestinal tract by a microbe can be determined by measuring the presence of the microbe in the animal's feces. It is expected that decreasing the colonization of an animal by a microbe will reduce transmission of the microbe to other animals of the same or different species.

Also provided is the use of antibody to target a microbe expressing a protein having an epitope structurally related to an epitope present on a protein described herein. A composition described herein can be used to provide for active or passive immunization against bacterial infection. Generally, the composition can be administered to an animal to provide active immunization. However, the composition can also be used to induce production of immune products, such as antibodies, which can be collected from the producing animal and administered to another animal to provide passive immunity. Immune components, such as antibodies, can be collected to prepare compositions (preferably containing antibody) from serum, plasma, blood, colostrum, etc. for passive immunization therapies. Antibody compositions including monoclonal antibodies and/or anti-idiotypes can also be prepared using known methods. Chimeric antibodies include human-derived constant regions of both heavy and light chains and murine-derived variable regions that are antigen-specific (Morrison et al., Proc. Natl. Acad. Sci. USA, 1984, 81(21):6851-5; LoBuglio et al., Proc. Natl. Acad. Sci. USA, 1989, 86(11):4220-4; Boulianne et al., Nature, 1984, 312(5995):643-6). Humanized antibodies substitute the murine constant and framework (FR) (of the variable region) with the human counterparts (Jones et al., Nature, 1986, 321(6069):522-5; Riechmann et al., Nature, 1988, 332(6162):323-7; Verhoeyen et al., Science, 1988, 239(4847):1534-6; Queen et al., Proc. Natl. Acad. Sci. USA, 1989, 86(24):10029-33; Daugherty et al., Nucleic Acids Res., 1991, 19(9): 2471-6). Alternatively, certain mouse strains can be used that have been genetically engineered to produce antibodies that are almost completely of human origin; following immunization the B cells of these mice are harvested and immortalized for the production of human monoclonal antibodies (Bruggeman and Taussig, Curr. Opin. Biotechnol., 1997, 8(4):455-8; Lonberg and Huszar, Int. Rev. Immunol., 1995; 13(1):65-93; Lonberg et al., Nature, 1994, 368:856-9; Taylor et al., Nucleic Acids Res., 1992, 20:6287-95). Passive antibody compositions and fragments thereof, e.g., scFv, Fab, F(ab')$_2$ or Fv or other modified forms thereof, may be administered to a recipient in the form of serum, plasma, blood, colostrum, and the like. However, the antibodies may also be isolated from serum, plasma, blood, colostrum, and the like, using known methods for later use in a concentrated or reconstituted form such as, for instance, lavage solutions, impregnated dressings and/or topical agents and the like. Passive immunization preparations may be particularly advantageous for the treatment of acute systemic illness, or passive immunization of young animals that failed to receive adequate levels of passive immunity through maternal colostrum. Antibodies useful for passive immunization may also be useful to conjugate to various drugs or antibiotics that could be directly targeted to bacteria expressing during a systemic or localized infection a protein having an epitope structurally related to an epitope present on a protein described herein.

Animal models, in particular mouse models, are available for experimentally evaluating the compositions described herein. These mouse models are commonly accepted models for the study of disease caused by gram-negative microbes. In those cases where a gram-negative microbe causes disease in an animal, for instance a cow, the natural host can be used to experimentally evaluate the compositions described herein.

However, protection in a mouse model is not the only way to assess whether a composition can confer protection to an animal against infection by a gram-negative microbe. The adaptive immune response consists of two primary divisions: the humoral (antibody) response and the cellular (T cell) response. Following infection by a bacterial pathogen, dendritic cells at the infection site encounter microbial antigens and produce signaling molecules such as, for example, surface receptors and cytokines in response to conserved molecular patterns associated with the specific bacterium. These signals are shaped by the nature of the pathogen and ideally lead to the appropriate antibody and T cell responses that protect the host from disease. While some bacterial diseases are controlled primarily through antibody functions, others require T cell responses or both antibody and T cell responses for protection. The goal of vaccine biology is to identify the immune responses that provide protection and then design a vaccine to reproduce one or more of these responses in humans.

Antibodies can have many different functions in conferring protection against infection such as, for example, complement fixation, opsonization, neutralization, and/or agglutination. Moreover, some subclasses of antibodies are better than others at specific functions; for example, for complement fixation the following hierarchy exists for human IgG subclasses: IgG3>IgG1>IgG2>IgG4.

Antibody immunological functions can be studied in a variety of ways. For instance, Western blots are used to identify antigen-specific binding based on size of separated proteins, while the standard enzyme-linked immunosorbant assay (ELISA) is used to produce quantitative information about antibody titers within serum. Antibody surface binding studies are used to determine whether antibody in serum are able to recognize antigens on the surface of intact bacteria, an important indicator of whether the antibodies have the potential to work in vivo. Thus, one skilled in the art recognizes that antibody binding assays such as a Western blot, ELISA (e.g., using human antisera), and/or surface binding correlate positively with the specifically-bound antigens providing immunological activity against microbial infection. However, one skilled in the art further recognizes that a lack of antibody binding in an assay such as, for example, a Western blot, ELISA, or surface binding assay does not mean that the assayed antigen fails to provide immunological activity against microbial infection.

Antibodies can mediate bacterial death by blocking the acquisition of nutrients or initiating complement-mediated membrane perforation that leads to osmotic lysis. Bactericidal antibodies can be assayed by mixing serum with live cultures and measuring for the presence of viable bacteria under appropriate conditions known to those skilled in the art. Techniques such as opsonophagocytosis assays (OPA), in which antibody and complement-bound bacteria are combined with human or mouse phagocytes to determine levels of bacterial killing, are useful for studying antibody function. A similar oxidative burst assay can be used to assess the level of reactive oxygen species (ROS) by fresh human or mouse neutrophils following interaction with antibody and complement-bound bacteria.

In some cases, one can determine that a protein described herein possesses cell-mediated immunological activity against a gram-negative microbe and, therefore, the protein may exhibit immunological activity in the absence of inducing the production of antibodies. Cytotoxic or CD8 T cells primarily kill infected cells directly through various effector mechanisms, while helper CD4 T cells function to provide important signaling in the way of cytokines. These T cell classes can be further subdivided based on the cytokines they produce, and different subclasses are effective against different bacterial pathogens. T cells are often studied by assessing their phenotypes with flow cytometry, where antibodies are used to visualize the levels of specific surface markers that enable classification of the T cells as, for example, a recently activated $CD4^+$ T cell, a memory $CD8^+$ T cell, etc. In addition, cytokines and other products of T cells can be studied by isolating the T cells from lymphoid tissue and restimulating them with cognate antigen. Following antigen stimulation the T cells produce cytokines that may be visualized by, for example, intracellular cytokine staining coupled with flow cytometry, or collecting the cell supernatants and using Luminex bead technology to measure 15-25 cytokines simultaneously.

Thus, in addition to mouse models, those of ordinary skill in the art recognize that immunological activity commensurate with the methods described herein may correlate with any one or more of the following: Western blot data showing that serum from animals exposed to a microbial pathogen contains antibody that specifically binds to a protein described herein, Western blot data showing that serum from animals exposed to protein described herein contains antibody that specifically binds to a gram-negative microbe, cell surface binding assays demonstrating that antibody that specifically binds to a protein described herein specifically binds to a gram-negative microbe, opsonophagocytosis data, and cytokine induction.

Also provided is a method for detecting antibody that specifically binds proteins described herein. These methods are useful in, for instance, detecting whether an animal has antibody that specifically binds a protein described herein, and diagnosing whether an animal may have a condition caused by a microbe expressing proteins that share epitopes with the proteins described herein. Such diagnostic systems may be in kit form. The methods include contacting an antibody with a preparation that includes a protein described herein to result in a mixture. The antibody may be present in a biological sample, for instance, blood, milk, or colostrum. The method further includes incubating the mixture under conditions to allow the antibody to specifically bind the protein to form a protein:antibody complex. As used herein, the term "protein:antibody complex" refers to the complex that results when an antibody specifically binds to a protein. The preparation that includes the proteins described herein may also include reagents, for instance a buffer, that provide conditions appropriate for the formation of the protein:antibody complex. The protein:antibody complex is then detected. The detection of antibodies is known in the art and can include, for instance, immunofluorescence or peroxidase. The methods for detecting the presence of antibodies that specifically bind to proteins described herein can be used in various formats that have been used to detect antibody, including radioimmunoassay and enzyme-linked immunosorbent assay.

Kits

Also provided are kits. In one embodiment, a kit is for detecting antibody that specifically binds a protein described herein. The antibody detected may be obtained from an animal suspected of having an infection caused by a gram-negative microbe. In another embodiment, a kit is for detecting a protein described herein. In yet another embodiment, a kit is for using a protein described herein, such as using a protein to produce antibody, treat a condition, or treat an infection.

The kit includes at least one of the proteins described herein (e.g., one, at least two, at least three, etc.), or an antibody described herein in a suitable packaging material in an amount sufficient for at least one assay or use. Optionally, other reagents such as buffers and solutions are also included. For instance, a kit may also include a reagent to permit detection of an antibody that specifically binds to a protein described herein, such as a detectably labeled secondary antibody designed to specifically bind to an antibody obtained from an animal. Instructions for use of the packaged antibody or protein are also typically included. As used herein, the phrase "packaging material" refers to one or more physical structures used to house the contents of the kit. The packaging material is constructed by routine methods, generally to provide a sterile, contaminant-free environment. The packaging material may have a label which indicates that the proteins can be used for detecting antibody that specifically binds a protein described herein, or using a protein described herein. In addition, the packaging material contains instructions indicating how the materials within the kit are employed to detect the antibody or administer a protein to an animal. As used herein, the term "package" refers to a container such as glass, plastic, paper, foil, and the like, capable of holding within fixed limits the proteins, and other reagents, for instance a secondary antibody. Thus, for example, a package can be a microtiter plate well to which microgram quantities of proteins have been affixed. A package can also contain a secondary antibody. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

Exemplary Embodiments

Embodiment 1. A non-natural protein comprising an amino acid sequence having at least 80% sequence identity to the amino acid sequence of SEQ ID NO:5 or SEQ ID NO:6, wherein the protein protects an animal against infection with *E. coli*.

Embodiment 2. A non-natural protein comprising an amino acid sequence having at least 80% sequence identity to the amino acid sequence of SEQ ID NO:3, wherein the protein reacts with convalescent serum from an animal infected with *E. coli*.

Embodiment 3. The protein of any one of Embodiments 1 or 2 wherein the protein further comprises two or more copies of the amino acid sequence, wherein the two or more copies are present as a tandem repeat.

Embodiment 4. The protein of any one of Embodiments 1 to 3 wherein the protein comprises at least three copies of the amino acid sequence, wherein the three or more copies are present as a tandem repeat.

Embodiment 5. A non-natural protein comprising an amino acid sequence having at least 80% sequence identity to the amino acid sequence of SEQ ID NO:4, wherein the protein reacts with convalescent serum from an animal infected with *E. coli*.

Embodiment 6. The protein of Embodiment 5 wherein the protein further comprises two or more copies of the amino acid sequence, wherein the two or more copies are present as a tandem repeat.

Embodiment 7. The protein of Embodiment 5 or 6 wherein the protein comprises at least three copies of the amino acid sequence, wherein the three or more copies are present as a tandem repeat.

Embodiment 8. The protein of any of one of Embodiments 1-7 wherein the protein includes a linker.

Embodiment 9. The protein of Embodiment 8 wherein the protein includes a linker.

Embodiment 10. The protein of Embodiment 8 or 9 wherein at least one linker comprises the amino acid sequence GSGS (SEQ ID NO:23).

Embodiment 11. A non-natural protein comprising a B cell domain selected from the group consisting of SEQ ID NO:12, SEQ ID NO:13, and SEQ ID NO:14, and a T cell domain selected from the group consisting of SEQ ID NO:15, SEQ ID NO:16, and SEQ ID NO:17.

Embodiment 12. A non-natural protein comprising a B cell domain selected from the group consisting of SEQ ID NO:18, SEQ ID NO:19, and SEQ ID NO:20, and a T cell domain selected from the group consisting of SEQ ID NO:21 and SEQ ID NO:22.

Embodiment 13. The protein of Embodiment 11 or 12 wherein the B cell domain and T cell domain are present in the order B cell domain-T cell domain.

Embodiment 14. A non-natural protein comprising amino acids 7-518 of the amino acid sequence of SEQ ID NO:8 or amino acids 7-365 of the amino acid sequence of SEQ ID NO:10.

Embodiment 15. A non-natural protein comprising amino acids 7-422 of the amino acid sequence of SEQ ID NO:26 or amino acids 7-461 of the amino acid sequence of SEQ ID NO:28.

Embodiment 16. A non-natural protein selected from protein 1-9 of Table 1, protein 10-15 of Table 2, protein 16-51 of Table 3, protein 52-63 of Table 4, protein 64-69 of Table 5, protein 70-78 of Table 6, protein 79-90 of Table 7, or protein 91-126 of Table 8, or having at least 80% sequence identity to the amino acid sequence of protein 1-9 of Table 1, protein 10-15 of Table 2, protein 16-51 of Table 3, protein 52-63 of Table 4, protein 64-69 of Table 5, protein 70-78 of Table 6, protein 79-90 of Table 7, or protein 91-126 of Table 8.

Embodiment 17. The protein of Embodiment 16 wherein the protein further comprises a linker located between a B cell domain and a T cell domain.

Embodiment 18. The protein of Embodiment 16 wherein the protein further comprises a linker located between each B cell domain and T cell domain.

Embodiment 19. A non-natural protein comprising:
a first domain comprising an amino acid sequence having at least 80% identity to amino acids 1-33 of SEQ ID NO:1,
a second domain comprising an amino acid sequence having at least 80% identity to amino acids 34-48 of SEQ ID NO:1,
a third domain comprising an amino acid sequence having at least 80% identity to amino acids 49-88 of SEQ ID NO:1, and
a fourth domain comprising an amino acid sequence having at least 80% identity to amino acids 89-103 of SEQ ID NO:1,
a fifth domain comprising an amino acid sequence having at least 80% identity to amino acids 104-133 of SEQ ID NO:1, and a sixth domain comprising an amino acid sequence having at least 80% identity to amino acids 34-148 of SEQ ID NO:1, wherein the first, third, and fifth domains have B cell activity and the second, fourth, and sixth domains have T cell activity, and wherein the protein protects an animal against infection with *E. coli*.

Embodiment 20. A non-natural protein comprising:

a first domain comprising an amino acid sequence having at least 80% identity to amino acids 1-23 of SEQ ID NO:2, a second domain comprising an amino acid sequence having at least 80% identity to amino acids 24-38 of SEQ ID NO:2, a third domain comprising an amino acid sequence having at least 80% identity to amino acids 39-75 of SEQ ID NO:2, and a fourth domain comprising an amino acid sequence having at least 80% identity to amino acids 76-90 of SEQ ID NO:2, and a fifth domain comprising an amino acid sequence having at least 80% identity to amino acids 91-101 of SEQ ID NO:2, wherein the first, third, and fifth domains have B cell activity and the second and fourth domains have T cell activity, and wherein the protein protects an animal against infection with *E. coli*.

Embodiment 21. The protein of any one of Embodiments 1-10, 19, or 20 wherein the animal is an avian, a bovine, a caprine, an ovine, a porcine, a bison, an equine, a companion animal, a member of the family Cervidae, or a human.

Embodiment 22. The protein of any one of Embodiments 1-10, 19, or 20 wherein the *E. coli* is CFT073.

Embodiment 23. A composition comprising the protein of any one of Embodiments 1-20.

Embodiment 24. The composition of Embodiment 23 further comprising a pharmaceutically acceptable carrier.

Embodiment 25. The composition of Embodiment 23 or 24 further comprising an adjuvant.

Embodiment 26. A method comprising:

administering to a subject an amount of the composition of any one of Embodiments 23 to 25 effective to induce the subject to produce antibody that specifically binds to the protein, produce helper T cells, suppressor T cells, and/or cytotoxic T cells directed to an epitope of a protein present in the composition, or a combination thereof.

Embodiment 27. A method for treating an infection in a subject, the method comprising:

administering an effective amount of the composition of any one of Embodiments 23 to 25 to a subject having or at risk of having an infection caused by a gram-negative microbe.

Embodiment 28. A method for treating a symptom in a subject, the method comprising:

administering an effective amount of the composition of any one of Embodiments 23 to 25 to a subject having or at risk of having an infection caused by a gram-negative microbe.

Embodiment 29. A method for decreasing colonization in a subject, the method comprising:

administering an effective amount of the composition of any one of Embodiments 23 to 25 to a subject colonized by a gram-negative microbe.

Embodiment 30. A method for treating a condition in a subject, the method comprising:

administering an effective amount of the composition of any one of Embodiments 23 or 25 to a subject in need thereof, wherein the subject has or is at risk of having a condition caused by a gram-negative microbe.

Embodiment 31. The method of any one of Embodiments 26 to 30 wherein the gram-negative microbe is a pathogenic microbe that is a member of the family Vibrionaceae, a member of the family Enterobacteriaceae, a member of the family Pasteurellaceae, a member of the family Pseudomonadaceae, or a *Campylobacter* spp.

Embodiment 32. A method for treating an infection in a subject, the method comprising:

administering an effective amount of a composition to a subject having or at risk of having an infection caused by a gram-negative microbe, wherein the composition comprises antibody that specifically binds to a protein of the composition of any one of Embodiments 1 to 24.

Embodiment 33. A method for treating a symptom in a subject comprising:

administering an effective amount of a composition to a subject having or at risk of having an infection caused by a gram-negative microbe, wherein the composition comprises antibody that specifically binds to a protein of the composition of any one of Embodiments 1 to 24.

Embodiment 34. A method for decreasing colonization in a subject, the method comprising:

administering an effective amount of a composition to a subject colonized by a gram-negative microbe, wherein the composition comprises antibody that specifically binds to a protein of the composition of any one of Embodiments 1 to 24.

Embodiment 35. A method for treating a condition in a subject, the method comprising:

administering an effective amount of a composition to a subject in need thereof, wherein the composition comprises antibody that specifically binds to a protein of the composition of any one of Embodiments 1 to 24, wherein the subject has or is at risk of having a condition caused by a gram-negative microbe.

Embodiment 36. The method of any one of Embodiments 32 to 35 wherein the gram-negative microbe is a pathogenic microbe that is a member of the family Vibrionaceae, a member of the family Enterobacteriaceae, a member of the family Pasteurellaceae, a member of the family Pseudomonadaceae, or a *Campylobacter* spp.

Embodiment 37. The method of any one of Embodiments 26 to 36 wherein the subject is a mammal or an avian.

Embodiment 38. The method of Embodiment 37 wherein the mammal is a human or a bovine.

Embodiment 39. The method of Embodiment 37 wherein the avian is a domesticated fowl.

Embodiment 40. The method of Embodiment 39 wherein domesticated fowl is a chicken or a turkey.

Embodiment 41. The method of any one of Embodiments 31 or 36 wherein the member of the family Enterobacteriaceae is *E. coli* or *Klebsiella* spp.

EXAMPLES

The present invention is illustrated by the following examples. It is to be understood that the particular examples, materials, amounts, and procedures are to be interpreted broadly in accordance with the scope and spirit of the invention as set forth herein.

Example 1

Selection of *E. coli* Isolates

Four avian pathogenic strains of *E. coli* were used in the following mouse sepsis studies. The avian strains were isolated from commercial chicken and turkey flocks showing clinical signs of colibacillosis. The avian isolates were given the following designations; APEC-280 (chicken); APEC-13 (chicken); APEC-374 (chicken) and APEC-J4 (turkey).

Example 2

Preparation of *E. coli* Seed Stocks

To preserve the original isolates, a master seed stock of each isolate was prepared by inoculating the appropriate isolate into 200 ml of tryptic soy broth (TSB, Difco Laboratories, Detroit, Mich.) containing 300 µM 2,2-dipyridyl (Sigma-Aldrich St. Louis, Mo.). The culture was grown while stirring at 200 rpm for 6 hours at 37° C. and collected by centrifugation at 10,000×g. The bacterial pellet was re-suspended into 100 ml TSB broth containing 20% glycerol, and sterilely dispensed into 2 ml cryogenic vials (1 ml per vial) and stored at −90° C. until use. The master seed stock was expanded into a working seed. One vial of the previously prepared master seed was inoculated into 200 ml TSB, containing 300 µM 2,2-dipyridyl (Sigma). The culture was grown while stirring at 200 rpm for 6 hours at 37° C. and collected by centrifugation at 10,000×g. The bacterial pellet was resuspended into 100 ml TSB broth containing 20% glycerol, and sterilely dispensed into 2 ml cryogenic vials (1 ml per vial) and stored at −90° C. until use.

Example 3

Synthesis and Cloning of the Trimer-1 and Trimer-2 Proteins

The DNA coding sequences (SEQ ID NO:7 and 9) for the Trimer-1 protein (SEQ ID NO:8) and the Trimer-2 protein (SEQ ID NO:10) were produced by chemical synthesis (InVitrogen GeneArt; Life Technologies Inc., Grand Island, N.Y.) and inserted into the pMK-RQ vector using flanking NdeI and XhoI restriction sites engineered at the 5-prime and 3-prime termini, respectively. A sequence encoding a series of six histidines was engineered immediately after the AUG methionine start codon at the 5-prime terminus. Trimer-1 and Trimer-2 constructs were subcloned into the pET29b expression vector using the flanking NdeI and XhoI restriction sites and transformed into *E. coli* BL21(DE3) using standard recombinant DNA techniques. Clones were selected and verified by DNA sequencing (ACGT, Inc., Wheeling, Ill.).

Example 4

Expression and Purification of Recombinant Proteins

Recombinant polypeptides Trimer-1 and Trimer-2 were expressed in *E. coli* and purified using standard methods. In brief, frozen bacterial stocks (100 µl) were used to inoculate 20 ml of Luria-Bertani (LB) Broth containing the appropriate selective antibiotic (kanamycin for pET29b), and the culture was grown at 37° C. in a shaking incubator at 250 rpm. After 16 hours, the culture was diluted into 1 L of LB Broth containing the appropriate selective antibiotic, grown to an optical density (600 nm) of 0.6, and induced by the addition of 1 M IPTG to a final concentration of 1 mM. Alternatively, for larger batches, the culture was used to seed a 10 L fermenter that was induced with IPTG to a final concentration of 1 mM. Bacterial cell pellets were harvested by centrifugation at 4,000×g for 20 minutes at 4° C., washed in phosphate buffered saline (PBS, 8.0 g/l NaCl, 0.2 g/l KCl, 1.44 g/l Na$_2$HPO$_4$ and 0.24 g/l KH$_2$PO$_4$ pH 7.4), and stored at −80° C. until lysis. Insoluble inclusion bodies were enriched for through treatment with BUGBUSTER (Millipore) and were solubilized in an 8M urea buffer. Anion exchange (AEX) chromatography was utilized to remove endotoxin followed by a second AEX chromatography step to exchange the sample into a final buffer consisting of 20 mM sodium phosphate, 51 mM N-Octyl-β-D-glucopyranoside (nOG), 300 mM sodium chloride, and 300 mM urea (pH 9.5). The protein concentration was determined using the BCA method (Thermo Scientific, Rockford, Ill.) and polypeptide purity was measured by SDS-PAGE and densitometry (LI-COR Odyssey; LI-COR, Lincoln, Nebr.).

Example 5

Preparation of Nalidixic Acid Resistant *E. coli*

The selected *E. coli* isolates from Example 1 were made nalidixic acid resistant. The purpose of inducing resistance to a known antibiotic in the challenge strain is to be able to differentiate the challenge strain from other *E. coli* strains that may contaminate challenged samples due to their prevalence in the environment. To induce antibiotic resistance, each isolate was grown in increasing concentrations of nalidixic acid. Briefly, two 1-liter stock solutions of TSB containing 35 gm Tryptic Soy; 5 gm yeast extract and 2,2-dipyridyl at 25 µg was prepared and autoclaved for 30 minutes and subsequently cooled to 4° C. Nalidixic acid was added to one bottle of TSB by membrane filtration through a 0.2 µm filter to a final concentration of 150 µg/ml. The TSB containing 150 µg/ml nalidixic acid was diluted in 20 ml stock (50 ml conical tubes) solution using the TSB without nalidixic acid as the diluent to obtain the following concentrations: 0 (no nalidixic acid); 25 µg/ml; 50 µg/ml; 75 µg/ml; 100 µg/ml and non-diluted 150 µg/ml.

The isolates were removed from frozen storage and plated onto sheep blood agar and incubated at 37° C. for 24 hours at which point a single colony was picked and sterilely inoculated into one of the non-nalidixic acid tubes and incubated for 3 hours at 37° C. while stirring at 200 rpm. At three hours post inoculation 2 ml of the culture was transferred into 20 ml of the 25 µg/ml nalidixic acid tubes that was pre-warmed to 37° C. The cultures were allowed to grow at 37° C. while rapidly stirring at 200 rpm for 3 hours. This process was repeated two times and then transferred to the next concentration of nalidixic acid. If growth did not occur the process was repeated in the previous concentration and then transferred to the next increasing concentration. This was done for each concentration until growth was established at the highest concentration of nalidixic acid. Once growth was established at the 150 µg/ml level, the cultures were then plated onto EMB containing 150 µg/ml nalidixic acid. A single colony of each isolate was selected and transferred into 100 ml TSB containing 150 µg/ml nalidixic acid (media as described above). The cultures were allowed to grow at 37° C. for 4.5 hours or until an OD of 1.0 at 540 nm was achieved. The cultures were centrifuged at 8000 rpm for 20 minutes at which point the supernatants were discarded and the pellets re-suspended in 90 ml of TSB media as described above but containing 20% glycerol and 25 µg/ml 2,2-dipyridyl. One ml aliquots of each bacterial suspension were dispensed into 2 ml cryovials and stored at −90° C. until use.

Example 6

Preparation of E. coli Challenge Strains

In order to use these isolates as challenge strains, each isolate was dosed in mice to determine an approximate LD-80. Briefly, the nalidixic acid resistant strains previously prepared in Example 5 were subcultured from frozen stocks; 100 µl/100 ml into freshly prepared TSB containing 35 gm TSB; 5 gm yeast extract and 2,2-dipyridyl at 25 µg/liter. The cultures were stirred at 100 rpm for 14 hours at which point each was subcultured in the same media as described above that was pre-warmed to 37° C. From the overnight cultures 100 µl was sterilely transferred into 20 ml of the TSB media. The cultures were allowed to grow for 2 hours while shaking at 200 rpm at 37° C. After the 2 hour time period, 10 ml of each culture was transferred to 100 ml of pre-warmed TSB and incubated at 37° C. The cultures were allowed to grow until an OD of 1.2 at 540 nm was reached; at which point the culture was centrifuged at 8000 rpm for 15 minutes and each isolate was re-suspended into 50 ml cold PBS pH 7.2. The cultures were kept on ice until use.

Example 7

Serial Passage in Mice

To enhance the virulence of each isolate, each organism was serially passaged in the new host species (mice). Briefly, using the cultures as described above in Example 3, two mice were subcutaneously injected with either 0.1 or 0.2 cc at $1.0 \times 10^9$ CFU/ml of each isolate. Twenty-four hours post-inoculation mice were morbid but did not die. Mice were euthanized by cervical dislocation and each liver was cultured using a flamed loop that was plated onto blood agar and eosin methylene blue (EMB) agar containing 150 µg/ml nalidixic acid. Plates were incubated at 37° C. for 24 hours. A number of colonies from the 0.2 dose had grown on both the EMB and blood plate indicating the isolates had gone systemic. These colonies were streaked for isolation and again passed through mice using the same regimen. This time the 0.2 cc dose had approximately 20-50 colonies. This was repeated; livers cultured and plates had greater than 100 colonies. The liver cultured isolates were passed two additional times in mice (five serial passes total) which resulted in all mice dying at 24 hours post challenge; clearly demonstrating that each of the isolates adapted to grow in the new host species by the enhancement of virulence with death as the outcome parameter.

Example 8

Preparation of Frozen Working Seeds (Mouse Pass 5)

The nalidixic acid resistant E. coli isolates of serial mouse pass five were subcultured from EMB plates and expanded into frozen working seeds. Briefly single colonies from the EMB plates were subcultured into 20 ml of TSB containing 32 g TSB; 5 g yeast extract and 2,2-dipyridyl at 25 µg/liter. The cultures were allowed to stir at 200 rpm for 2 hours at which point they were subcultured in the same media that was pre-warmed to 37° C. After the 2 hour time period, 10 ml of each culture was transferred to 100 ml of pre-warmed TSB as described above except the concentration of 2,2-dipyridyl was 25 µg/l. These cultures were allowed to grow until they reached an OD 1.0 at 540 nm at which point they were centrifuged at 8000 rpm for 10 minutes and resuspended into 90 ml cold TSB as described above, plus the addition of 20% glycerol. One ml aliquots of each bacterial suspension were dispensed into 2 ml cryovials; labeled and stored at −90° C. until use.

Example 9

Serial Passage of APEC-280 in Chickens

The previous working seed APEC-280 of Example 1 that had been made nalidixic acid resistant as described in Example 5 was passed in chickens and expanded into a new working seed. This was done to enhance the virulence of APEC-280 isolate. Briefly, two seven week old specific pathogen free leghorn hens obtained from Valo BioMedia, (Adel, Iowa) were IV injected with either 0.1 or 0.2 cc at $1.0 \times 10^8$ CFU/ml of the APEC-280 isolate. Twenty-four hours post inoculation chickens were morbid but did not die. Chickens were euthanized by cervical dislocation and each liver was cultured using a flamed loop and plated onto blood agar and EMB agar containing 150 µg/ml nalidixic acid. Plates were incubated at 37° C. for 24 hours. A number of colonies from the 0.2 dose had grown on both the EMB and blood plate indicating the isolates had gone systemic. These colonies were streaked for isolation and again passed through chickens using the same regimen. This time the 0.2 cc dose had approximately 20-50 colonies. This was repeated; livers were cultured and plates now had greater than 100 colonies. The liver cultured isolates were again passed two more consecutive times in chickens (five serial passes total) which resulted in all chickens dying at 24 hours post challenge, clearly demonstrating that the APEC-280 isolate adapted to grow in the new host species by the enhancement of virulence with death as the outcome parameter. This seed was expanded into a new working seed using the same culture methodology of Example 8 and used as the challenge strain in chickens and turkeys as described in the following experiments.

Example 10

Sepsis Lethal Dose Preparation

The E. coli isolates, now nalidixic acid resistant and virulent in mice, were dose titrated to induce mortality in 80-100% of mice challenged subcutaneously. Briefly, 24 hours before challenge, 100 ml of TSB containing 35 g of tryptic soy; 5 g yeast extract and 25 µg/ml 2,2-dipyridyl per liter was inoculated from the frozen stocks (100 µl) of Example 8 and incubated for 14 hours at 37° C. while stirring at approximately 100 rpm. Fourteen hours post inoculation of the above culture; 100 µl was then inoculated into 20 ml of pre-warmed TSB as described above in 50 ml conical tubes; incubated at 37° C. while stirring at 200 rpm to an OD of 0.8 at 540 nm. Once the cultures reached an OD 0.8; 10 ml of each culture was sterilely inoculated into 100 ml of pre-warmed TSB containing 35 g of tryptic soy; 5 g yeast extract and 25 µg/ml 2,2-dipyridyl per liter; incubated at 37° C. while stirring at 200 rpm until an OD of 0.92-0.95 at 540 nm was reached. Immediately upon reaching the desired OD, the cultures were transferred to 250 ml centrifuge bottles at which point 100 ml of 4° C. PBS was added to stop growth. The cultures were centrifuged for 20 minutes using a JA14 Beckman rotor at 8,000×g. After centrifugation, the supernatants were removed using individual 50 ml pipets and the supernatants discarded. Then 20 ml of 4° C. PBS was added back to the individual pellets and evenly resuspended by pipetting. The bacterial suspension was transferred to a 50 ml conical tube and vortexed vigorously (30 seconds) to evenly disperse the bacterial pellets. Each bacterial suspension was transferred to a sterile 250 ml centrifuge bottle, at which point it was brought back to its original volume of 100 ml by adding 80 ml of 4° C. PBS and mixing thoroughly.

Example 11

Sepsis Lethal Dose Titration

The bacterial suspensions of Example 10 were tested in mice at different dilutions: 1) direct 0.1 cc of non-diluted stock bacterial suspension, 2) stock suspension diluted 1:2 (1 ml into 1 ml) in cold PBS pH 7.4; 3) stock suspension diluted 1:10 (1 ml into 9 ml) in cold PBS pH 7.4 and 4) stock suspension diluted 1:100 (1 ml into 99 ml) in cold PBS pH 7.4. Each dilution was given to 10 mice via subcutaneous injection using a volume of 0.1 cc. Mice were observed for 7 days post challenge for mortality. These data showed that the non-diluted bacterial stock suspension derived from isolates APEC-280, APEC-13, APEC-374 and APEC-J4 killed 100% of the mice within a 24 hour time period, as compared to the 1:2 diluted stock suspension, which killed 30% of the mice at 24 hours and 50% of the mice at the 48 hour time period. Furthermore, no mice receiving the 1:10 dilution died within the observation period. Based on this preliminary evaluation, the challenge dose of the APEC isolates was determined to be a 1:2 dilution of the stock suspension of approximately $2.0 \times 10^8$ CFU/ml. Thus, the frozen APEC isolates of Mouse Pass 5 were used at a mouse dose of approximately $2.0 \times 10^7$ CFU in a 0.1 ml volume.

Example 12

Enzyme-Linked Immunosorbent Assay (ELISA)

The immunological response to individual recombinant proteins was determined by measuring the IgG titers by ELISA. In brief, 100 µl of polypeptide at 2 µg/ml, solubilized in 5 M urea, was added to each well of a 96-well EIA/RIA plate (Corning/Costar 3590) and incubated overnight at 4° C. All remaining steps were performed at room temperature. The plate was washed three times with PBS wash buffer (PBS containing 0.05% Tween 20) followed by the addition of 200 µl/well sample buffer consisting of PBS containing 0.05% Tween 20 and 1% bovine serum albumin. After 90 minutes, the sample buffer was replaced with 100 µl/well PBS sample buffer. Serial 1:3 dilutions of the primary antisera were performed in the plate by the addition of 50 µl to the first row, mixing 10 times, and transfer of 50 µl to the next row. The plate was incubated for 90 minutes followed by three washes and addition of 100 µl/well of an HRP conjugated goat anti-mouse IgG, heavy chain specific antibody (Jackson ImmunoResearch, West Grove, Pa.). After a 90 minute incubation period the plate was washed four times followed by the addition of 100 µl TMB (BioFx; Surmodics, Eden Prairie, Minn.)/well. Color was allowed to develop for 30 minutes, and the reaction was stopped by the addition of 100 µl stop reagent (BioFx). The absorbance was measured at a wavelength of 450 nm, and the titer was calculated as the inverse of the dilution corresponding to an absorbance of 1.0. Controls included a standardized primary serum included on each plate to monitor assay variability and wells that were uncoated to subtract background. The limit of detection for the assay was the inverse of the initial serum dilution.

Example 13

Evaluation of Vaccine Efficacy in Mice Challenged with Different Strains and Serotypes of *E. coli*

Experimental Overview of Sepsis Experiments

The overall goal of the following studies was to evaluate the efficacy of Trimer-1 and Trimer-2 as vaccine antigens to control various disease conditions caused by gram-negative bacteria. Four different strains of *E. coli* were used for the following experimental challenges; APEC-280, APEC-13, APEC-J4, and APEC-374 of Example 8.

In this first study, we evaluated the efficacy of Trimer-1 against challenge with four different strains of *E. coli*: APEC-280; APEC-13; APEC-J4 and APEC-374. The outcome parameters used to evaluate vaccine efficacy were 1) efficacy of a single protein, Trimer-1, against systemic challenge and 2) ability of Trimer-1 to cross-protect against different strains and/or serotypes.

Briefly, 180 female Harlan CF-1 mice obtained from Charles River Laboratory (Wilmington, Mass.) weighing 16-22 grams were equally divided into 4 experimental groups (45 mice/group) designated as 1-4 (Table 9). Each of these groups was further divided into 3 subgroups so that each subgroup consisted of 15 mice designated now as 1 (A, D, E); 2 (F, I, J); 3 (K, N, O) and 4 (P, S, T) (Table 9). Each subgroup represented a vaccine formulation consisting of an adjuvanted placebo control and Trimer-1 formulated at 100 µg or 150 µg total protein. Thus, all groups consisted of an adjuvanted placebo and two vaccine formulations with different doses of Trimer-1.

TABLE 9

Experimental Design.

| Groups | Mice | Vaccine | Total Antigen (ug) | Adjuvant | Vaccine Volume (ul) | # Vaccines | Vaccine Route | Challenge strain |
|---|---|---|---|---|---|---|---|---|
| Group-1 | | | | | | | | |
| A | 15 | PBS | N/A | AlOH | 100 | 2 | SC | APEC-280 |
| D | 15 | Trimer-1 | 100 | AlOH | 100 | 2 | SC | APEC-280 |
| E | 15 | Trimer-1 | 150 | AlOH | 100 | 2 | SC | APEC-280 |

TABLE 9-continued

Experimental Design.

| Groups | Mice | Vaccine | Total Antigen (ug) | Adjuvant | Vaccine Volume (ul) | # Vaccines | Vaccine Route | Challenge strain |
|---|---|---|---|---|---|---|---|---|
| Group-2 | | | | | | | | |
| F | 15 | PBS | N/A | AlOH | 100 | 2 | SC | APEC-13 |
| I | 15 | Trimer-1 | 100 | AlOH | 100 | 2 | SC | APEC-13 |
| J | 15 | Trimer-1 | 150 | AlOH | 100 | 2 | SC | APEC-13 |
| Group-3 | | | | | | | | |
| K | 15 | PBS | N/A | AlOH | 100 | 2 | SC | APEC-J4 |
| N | 15 | Trimer-1 | 100 | AlOH | 100 | 2 | SC | APEC-J4 |
| O | 15 | Trimer-1 | 150 | AlOH | 100 | 2 | SC | APEC-J4 |
| Group-4 | | | | | | | | |
| P | 15 | PBS | N/A | AlOH | 100 | 2 | SC | APEC-374 |
| S | 15 | Trimer-1 | 100 | AlOH | 100 | 2 | SC | APEC-374 |
| T | 15 | Trimer-1 | 150 | AlOH | 100 | 2 | SC | APEC-374 |

Mice were housed in polycarbonate cages (Ancore Corporation, Bellmore, N.Y.) at 5 mice per cage with food and water supplied ad libitum. All mice were allowed to acclimate one week prior to the first vaccination. Mice were vaccinated two times at 21 day intervals and challenged 21 days post second vaccination. Groups were challenged with one of four challenge strains (Table 9).

Example 14

Vaccine Preparation and Vaccination

Vaccines containing recombinant Trimer-1 protein were prepared at 100 μg and 150 μg protein per dose in PBS formulated with 20 percent (v/v) ALHYDROGEL (Invivogen, San Diego, Calif.) in a final volume of 0.1 ml (Table 9). The placebo vaccines were prepared by substituting PBS for the aqueous protein suspension of the above described formulation. Mice were vaccinated two times at 21 day intervals.

Example 15

Preparation of Challenge Organisms

The four E. coli isolates APEC-280; APEC-13; APEC-J4 and APEC-374 as previously described in Example 1 were used as the challenge strains. Briefly, each isolate from a frozen stock of Example 8 was streaked onto a blood agar plate and incubated at 37° C. 18 hours. A single colony was subcultured into 50 ml of TSB (Difco) containing 25 μg per ml of 2,2' dipyridyl (Sigma). The cultures were allowed to grow for 12 hours at 37° C. while rotating at 100 rpm, at which point they were subcultured 1:100 into a final volume 50 ml of TSB as described above. The subcultures were incubated at 37° C. for 3 hours while rotating at 200 rpm, and allowed to reach an optical density (540 nm) of 0.6-0.8. Each culture was then subcultured a final time by transferring 10 ml into 90 ml of pre-warmed TSB containing 25 μg per ml of 2,2' dipyridyl and incubated at 37° C. for approximately 4 hours while rotating at 200 rpm until an optical density of 0.90-0.95 at 540 nm was reached. The growth of each culture was stopped by adding 100 ml of PBS at 4° C. The cultures were then centrifuged at 10,000×g for 15 minutes at 4° C. to pellet the bacteria. The bacterial pellets were washed once by centrifugation in PBS at 4° C. Twenty five milliliters of cold PBS was added to each bacterial pellet and vortexed vigorously for 30 seconds to thoroughly resuspend the pellets. This was followed by 75 ml of cold PBS added to each bacterial suspension for a final volume of 100 ml. Each culture was then diluted 1:2 in cold PBS and used for challenge. Just prior to challenge, 1 ml of the final bacterial suspension was serially diluted 10-fold and plated onto blood agar and EMB agar (containing 100 μg/ml of nalidixic acid) to enumerate the number of colony-forming units (CFU) per mouse dose.

Example 16

Challenge

Twenty one days after the second vaccination, all mice in groups 1 (A, D, E); 2 (F, G, J); 3 (K, N, O) and 4 (P, S, T) (Table 9) were subcutaneously challenged with 0.1 ml of the appropriate challenge strain. Group 1 (A, D, E) was challenged with APEC-280 at $1.0 \times 10^7$ colony forming units. Group 2 (F, G, J) was challenged with APEC-13 at $4.5 \times 10^7$ colony forming units. Group 3 (K, N, O) was challenged with APEC-J4 at $8.0 \times 10^7$ colony forming units; while group 4 (P, S, T) was challenged with APEC-374 at $5.5 \times 10^7$ colony forming units. Mortality was recorded daily for 10 days post-challenge. Table 10 shows the total mortality and percent survival of all groups following challenge for the 10 day observation period.

TABLE 10

Total Mortality and Percent Livability following Challenge using APEC-280, APEC 13, APEC J4 and APEC 374.

| Treatments | Number Dead on Indicated Days Post Challenge | | | | | | | | | | Challenge Strain | Total Mortality | Percent Survivability |
|---|---|---|---|---|---|---|---|---|---|---|---|---|---|
| | 1 | 2 | 3 | 4 | 5 | 6 | 7 | 8 | 9 | 10 | | | |
| Group-1 | | | | | | | | | | | | | |
| A) Placebo Adjuvanted | 0 | 15 | 0 | 0 | 0 | 0 | 0 | 0 | 0 | 0 | APEC-280 | 15/15 | 0 |
| D) Trimer-1 100 µg | 0 | 6 | 0 | 0 | 0 | 0 | 0 | 0 | 0 | 0 | APEC-280 | 6/15 | 60 |
| E) Trimer-1 150 µg | 0 | 2 | 1 | 0 | 0 | 0 | 0 | 0 | 0 | 0 | APEC-280 | 3/15 | 80 |
| Group-2 | | | | | | | | | | | | | |
| F) Placebo Adjuvanted | 0 | 7 | 2 | 0 | 2 | 2 | 0 | 0 | 0 | 0 | APEC-13 | 13/15 | 13 |
| I) Trimer-1 100 µg | 0 | 3 | 0 | 0 | 0 | 0 | 0 | 0 | 0 | 0 | APEC-13 | 3/15 | 80 |
| J) Trimer-1 150 µg | 0 | 2 | 0 | 2 | 0 | 0 | 0 | 0 | 0 | 0 | APEC-13 | 4/15 | 73 |
| Group-3 | | | | | | | | | | | | | |
| K) Placebo Adjuvanted | 4 | 4 | 2 | 0 | 0 | 0 | 0 | 0 | 0 | 0 | APEC-J4 | 10/15 | 33 |
| N) Trimer-1 100 µg | 0 | 0 | 0 | 0 | 0 | 0 | 0 | 0 | 0 | 0 | APEC-J4 | 0/15 | 100 |
| O) Trimer-1 150 µg | 0 | 1 | 0 | 0 | 0 | 0 | 0 | 0 | 0 | 0 | APEC-J4 | 1/15 | 93 |
| Group-4 | | | | | | | | | | | | | |
| P) Placebo Adjuvanted | 3 | 0 | 12 | 0 | 0 | 0 | 0 | 0 | 0 | 0 | APEC-374 | 15/15 | 0 |
| S) Trimer-1 100 µg | 10 | 0 | 0 | 0 | 0 | 0 | 0 | 0 | 0 | 0 | APEC-374 | 10/15 | 33 |
| T) Trimer-1 150 µg | 2 | 11 | 1 | 0 | 0 | 0 | 0 | 0 | 0 | 0 | APEC-374 | 14/15 | 7 |

Example 17

Challenge Results

Figure 1:
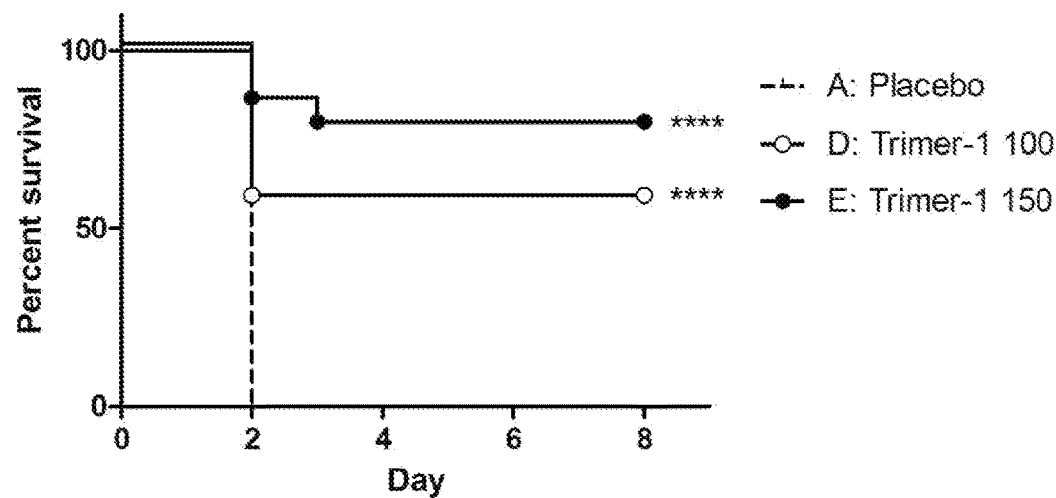
FIG. 1 shows cumulative mortality in Trimer-1 vaccinates and placebo following challenge with APEC-280. Mice received two vaccinations with Trimer-1 as indicated (100 µg or 150 µg), three weeks apart, and were challenged after a 3 week rest period. (Fisher's Exact Test; ****$P \leq 0.0001$)
Figure 2:
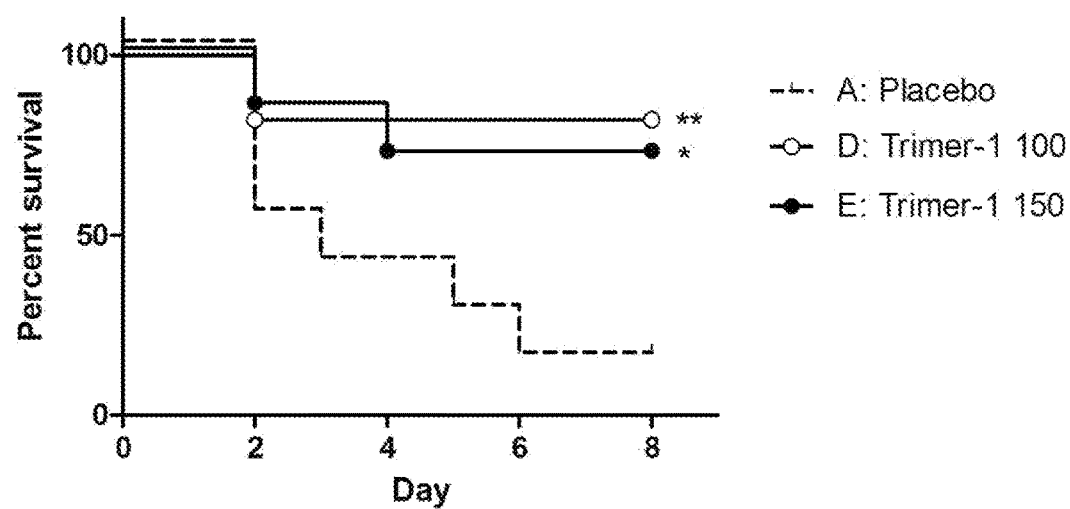
FIG. 2 shows cumulative mortality in Trimer-1 vaccinates and placebo following challenge with APEC-13. Mice received two vaccinations with Trimer-1 as indicated (100 µg or 150 µg), three weeks apart, and were challenged after a 3 week rest period. (Fisher's Exact Test; *$P<0.05$; **$P<0.01$)
Figure 3:
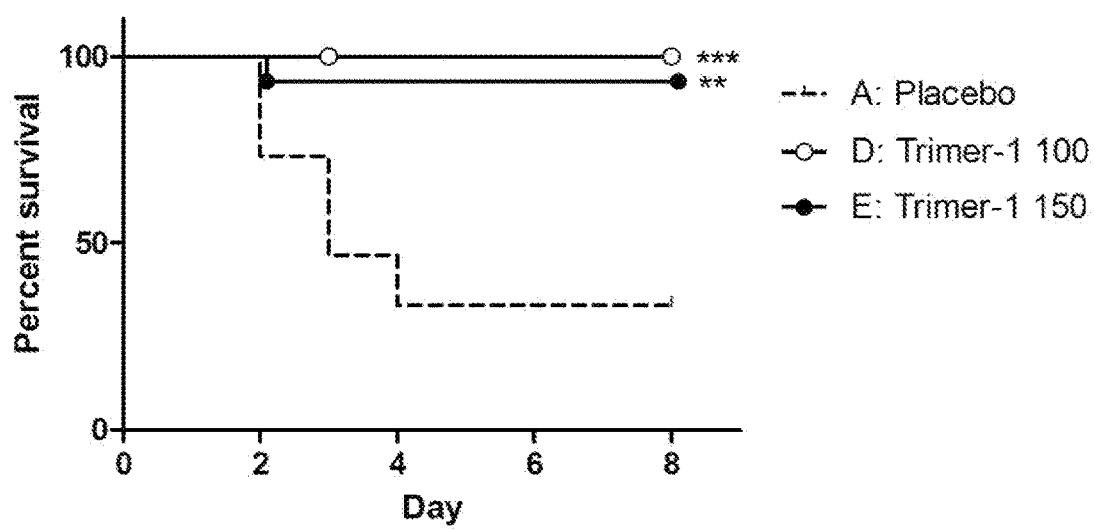
FIG. 3 shows cumulative mortality in Trimer-1 vaccinates and placebo following challenge with APEC-J4. Mice received two vaccinations with Trimer-1 as indicated (100 µg or 150 µg), three weeks apart, and were challenged after a 3 week rest period. (Fisher's Exact Test; $P<0.01$; *$P<0.001$)

Both doses of Trimer-1 showed excellent efficacy against systemic challenge using APEC-280; APEC-13 and APEC-J4 (Table 10; FIGS. 1, 2, and 3). Table 10 and FIG. 1 show the percent survival of group 1 (A, D, E); challenged with APEC-280. Both the 100 µg and 150 µg dose levels of Trimer-1 were highly protective against the APEC-280 challenge and were statistically significant in comparison to the placebo controls. The percent survival of group 1(D) at the 100 µg dose level was 60%; (6 out of 15 mice died) whereas the 150 µg dose level of group 1(E) was more efficacious, showing a percent survival of 80% (3 out of 15 mice died). All mice (15 out of 15) in placebo control group 1(A) died within 48 hours after challenge (Table 10; FIG. 1).

Results were comparable when using APEC-13 as the challenge strain. Group 2 (F, I, J) challenged with APEC 13, as illustrated in FIG. 2, showed statistically significant differences in the overall mortality between both vaccine groups compared to the placebo controls. The percent survival of the Trimer-1 group 2 (I) at the 100 µg dose level was 80%; (3 out of 15 mice died) (Table 10; FIG. 2). In comparison, Trimer-1 group 2 (J) at the 150 µg dose level was also protective, showing a percent survival of 73% and having only 4 out of 15 mice die (Table 10; FIG. 2). All vaccine groups challenged with APEC-13 survived at statistically significantly higher rates than placebo controls. Thirteen out of the fifteen placebo control mice died over a six day period with a survival rate of only 13%.

Similar results were obtained in group 3 (K, N, O) challenged with APEC J4 (Table 10; FIG. 3). The results showed statistically significant protection over the placebo controls for Trimer-1 at both the 100 µg and 150 µg dose levels. For example, FIG. 3 shows that the Trimer-1 group 3 (N) had a survival rate of 100% at a dose of 100 µg, i.e., none of the mice died in this group. The 150 µg dose level of Trimer-1 was also highly efficacious with a percent survival of 93%, having only 1 out of 15 mice die. Cumulative mortality of 67% (10 out of 15) occurred in the placebo control group 3 (K), with deaths occurring within 3 days after challenge (Table 10; FIG. 3).

Figure 4:
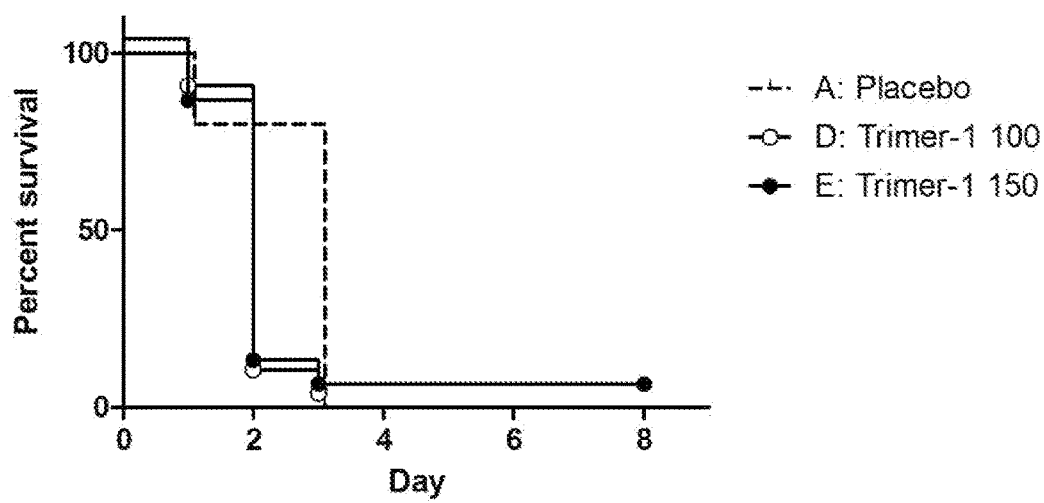
FIG. 4 shows cumulative mortality in Trimer-1 vaccinates and placebo following challenge with APEC-374. Mice received two vaccinations with Trimer-1 as indicated (100 µg or 150 µg), three weeks apart, and were challenged after a 3 week rest period. (Fisher's Exact Test; $P>0.05$)

In contrast to the other *E. coli* isolate tested, only moderate protection was achieved against challenge by APEC-374 (Table 10; FIG. 4). A greater level of investigation may be required regarding this challenge strain in contrast to the other three *E. coli* strains. For example, higher levels of protection against this strain may require a higher single antigen dose, or an additional immunization.

Overall, these studies demonstrated that Trimer-1 protected against multiple different strains of *E. coli* in a lethal murine sepsis model.

Example 18

Efficacy of Trimer-1 and Trimer-2 Against a Virulent *E. coli* Challenge in a Mouse Sepsis Model The efficacy of recombinant Trimer-1 and Trimer-2 was evaluated using a live virulent *E. coli* challenge with APEC-280 in mice, with death as the endpoint. The outcome parameters used to evaluate vaccine efficacy against APEC-280 were 1) titration of the antigenic dose of Trimer-1 and Trimer-2 to establish the range of protection against APEC-280, 2) duration of protection for Trimer-1 at both 3 and 8 weeks post-vaccination, and 3) correlation of antibody titers with survival.

Briefly, 165 female Harlan CF-1 mice obtained from Charles River Laboratory (Wilmington, Mass.) weighing 16-22 grams were equally divided into 11 treatment groups (n=15 mice/group) designated as indicated (Table 11). Mice were vaccinated two times at 21 day intervals and challenged with APEC-280 at 3 or 8 weeks post second vaccination. Mice were housed in polycarbonate cages (Ancore Corporation, Bellmore, N.Y.) at 5 mice per cage with food and water supplied ad libitum. All mice were allowed to acclimate one week prior to the first vaccination.

Example 19

Vaccine Preparation and Vaccination

Vaccines containing Trimer-1 or Trimer-2 were prepared at three different concentrations to establish an appropriate dose range of the specific recombinant protein. Trimer-1 was also evaluated to determine duration of immunity (DOI) at 3 and 8 weeks post second vaccination. Dose levels of 50 μg, 100 μg and 150 μg total protein were prepared in PBS formulated with 20 percent (v/v) ALHYDROGEL (Invivogen, San Diego, Calif.) in a final volume of 0.1 ml (Table 11). To evaluate the duration of immunity; mice were divided into two groups. Mice in groups A-I were used for establishing the duration of immunity at 3 weeks post second vaccination for Trimer-1 and Trimer-2 while mice in groups J-P were used to evaluate the duration of immunity 8 weeks post second vaccination (Table 11). Mice in groups A-I were vaccinated two times at 21 day intervals with the appropriate vaccine formulation and challenged 21 days post second vaccination; mice in groups M-P were vaccinated using the same regimen but were challenged 8 weeks post second vaccination (Table 11). Blood was taken from both groups on the day of first vaccination and again at 24 hours pre-challenge. Mice in groups A and P served as the placebo controls. The placebo vaccines of groups A and P were prepared by substituting PBS for the aqueous protein suspension as described in the above procedure.

Example 20

Preparation of Challenge Organism

The *E. coli* APEC-280 isolate previously described in Example 1 was used as the challenge strain. Briefly, the isolate from a frozen stock of Example 8 was streaked onto a blood agar plate and incubated at 37° C. 18 hours. A single colony was subcultured into 50 ml of TSB (Difco) containing 25 μg per ml of 2,2' dipyridyl (Sigma). The culture was allowed to grow for 12 hours at 37° C. while rotating at 100 rpm at which point was subcultured 1:100 into a final volume 50 ml of TSB as described above. The culture was incubated at 37° C. for 3 hours while rotating at 200 rpm, and allowed to reach an optical density (540 nm) of 0.6-0.8. The culture was then subcultured a final time by transferring 10 ml into 90 ml of pre-warmed TSB containing 25 μg per ml of 2,2' dipyridyl (Sigma) and incubated at 37° C. for approximately 4 hours while rotating at 200 rpm until an optical density of 0.92-0.95 at 540 nm was reached. The growth of the culture was stopped by adding 100 ml of PBS at 4° C. The culture was then centrifuged at 10,000×g for 15 minutes at 4° C. to pellet the bacteria. The bacterial pellet was washed once by centrifugation in PBS at 4° C. The final pellet was re-suspended back into 100 ml of cold PBS. This culture was then diluted 1:2 in cold PBS and used for challenge. Just prior to challenge, 1 ml of the final bacterial suspension was serially diluted 10-fold and plated onto blood agar and EMB agar (containing 100 μg/ml of nalidixic acid) to enumerate the number of colony-forming units (CFU) per mouse dose.

Example 21

Challenge Results

After the second vaccination, all mice in groups A-I (3 week DOI) and M-P (8 week DOI) were subcutaneously challenged with 0.1 ml at $1.0 \times 10^7$ colony forming units (CFU) of the virulent APEC-280 isolate to evaluate the protective efficacy of the recombinant proteins. Mortality was recorded daily for 10 days post-challenge. Table 12 shows the total mortality and percent survival of all groups following challenge with APEC-280 for the 10 day observation period.

TABLE 11

Experimental Design.

| Group | Mice | Vaccine | Total Antigen (μg) | Adjuvant | Vaccine Volume (ul) | # Vax | Vaccine Route | Rest Period | Challenge Strain |
|---|---|---|---|---|---|---|---|---|---|
| A | 15 | PBS | N/A | AlOH | 100 | 2 | SC | 3 | APEC-280 |
| C | 15 | Trimer-1 | 150 | AlOH | 100 | 2 | SC | 3 | APEC-280 |
| D | 15 | Trimer-1 | 100 | AlOH | 100 | 2 | SC | 3 | APEC-280 |
| E | 15 | Trimer-1 | 50 | AlOH | 100 | 2 | SC | 3 | APEC-280 |
| G | 15 | Trimer-2 | 150 | AlOH | 100 | 2 | SC | 3 | APEC-280 |
| H | 15 | Trimer-2 | 100 | AlOH | 100 | 2 | SC | 3 | APEC-280 |
| I | 15 | Trimer-2 | 50 | AlOH | 100 | 2 | SC | 3 | APEC-280 |
| M | 15 | Trimer-1 | 150 | AlOH | 100 | 2 | SC | 8 | APEC-280 |
| N | 15 | Trimer-1 | 100 | AlOH | 100 | 2 | SC | 8 | APEC-280 |
| O | 15 | Trimer-1 | 50 | AlOH | 100 | 2 | SC | 8 | APEC-280 |
| P | 15 | PBS | N/A | AlOH | 100 | 2 | SC | 8 | APEC-280 |

TABLE 12

Total Mortality and Percent Livability following Challenge using APEC-280.

| Treatments | Duration of Immunity (DOI) | Challenge Strain | Number Dead/ Number Tested (% Mortality) | Percent Survival (%) |
|---|---|---|---|---|
| A) Placebo Adjuvanted | 3 | APEC-280 | 15/15 (100) | 0 |
| C) Trimer-1 150 μg | 3 | APEC-280 | 1/15 (7) | 93 |
| D) Trimer-1 100 μg | 3 | APEC-280 | 8/14 (57) | 43 |
| E) Trimer-1 50 μg | 3 | APEC-280 | 12/15 (80) | 20 |
| G) Trimer-2 150 μg | 3 | APEC-280 | 6/13 (46) | 54 |
| H) Trimer-2 100 μg | 3 | APEC-280 | 4/15 (27) | 73 |
| I) Trimer-2 50 μg | 3 | APEC-280 | 6/15 (40) | 60 |
| M) Trimer-1 150 μg | 8 | APEC-280 | 2/15 (13) | 87 |
| N) Trimer-1 100 μg | 8 | APEC-280 | 1/14 (7) | 93 |
| O) Trimer-1 50 μg | 8 | APEC-280 | 11/14 (79) | 21 |
| P) Placebo Adjuvanted | 8 | APEC-280 | 14/15 (93) | 7 |

Figure 5:
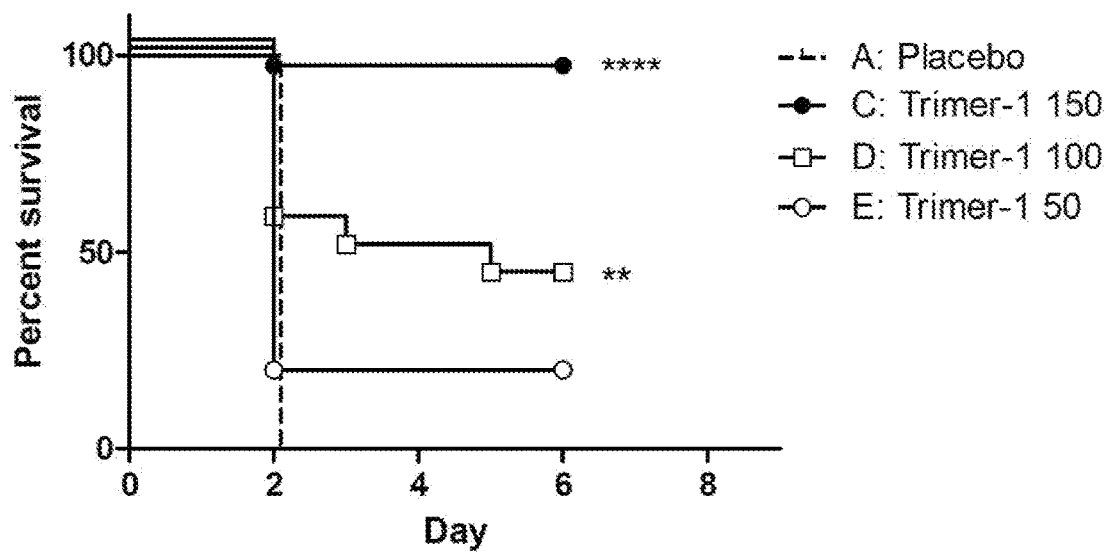
FIG. 5 shows cumulative mortality in Trimer-1 vaccinates and placebo following challenge with APEC-280. Mice received two vaccinations, 3 weeks apart, with Trimer-1 as indicated (50, 100, or 150 µg), and were challenged after a 3 week rest period. (Fisher's Exact Test; $P<0.01$; **$P \leq 0.0001$)
Figure 6:
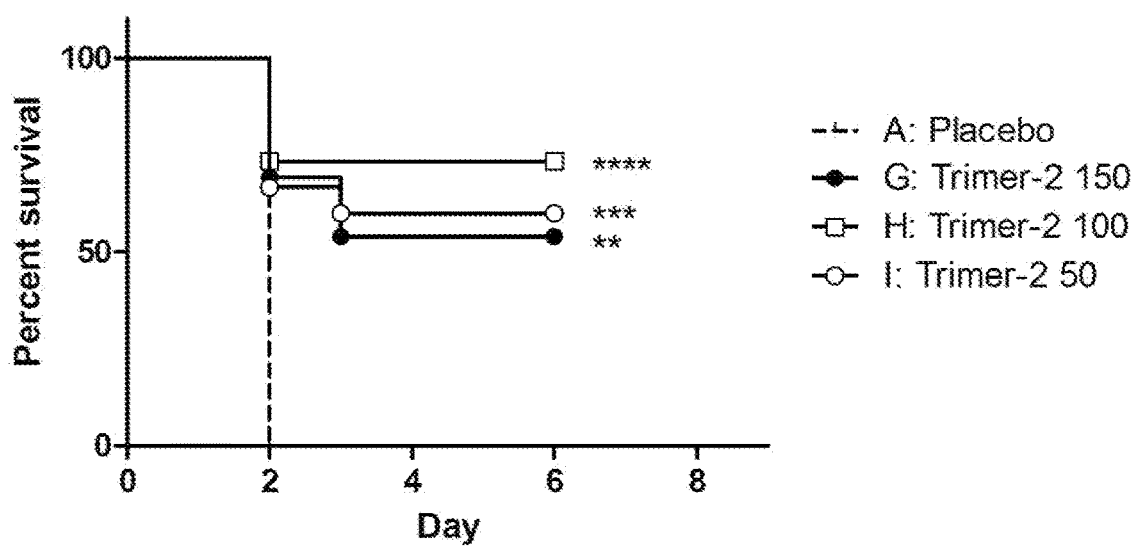
FIG. 6 shows cumulative mortality in Trimer-2 vaccinates and placebo following challenge with APEC-280. Mice received two vaccinations 3 weeks apart, as indicated (50, 100, or 150 µg), and were challenged after a 3 week rest period. (Fisher's Exact Test; $P<0.01$; *$P<0.001$; ****$P \leq 0.0001$)
Figure 7:
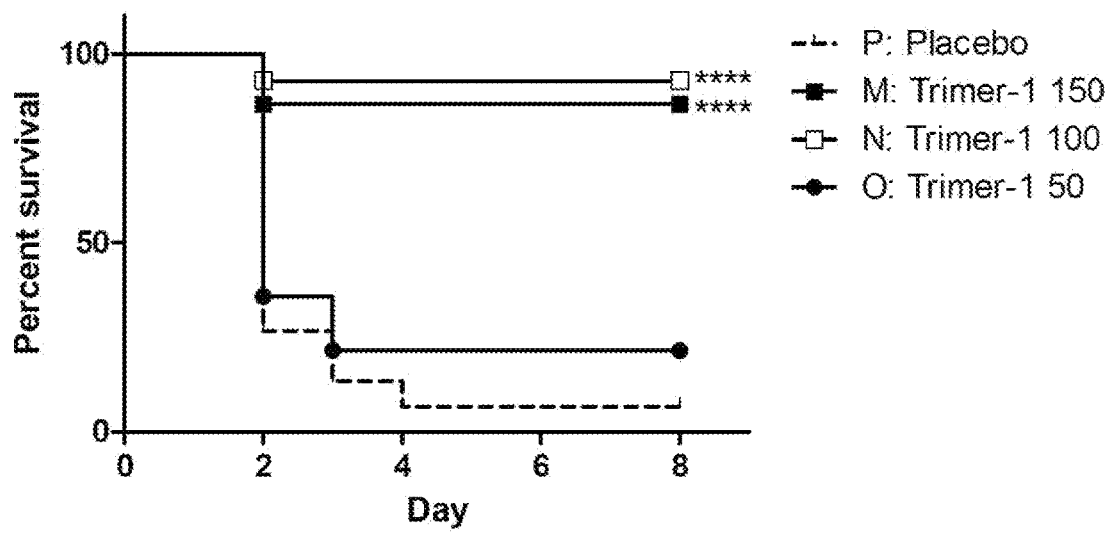
FIG. 7 shows cumulative mortality in Trimer-1 vaccinates and placebo following challenge with APEC-280 after an 8 week rest period. Mice received two vaccinations 3 weeks apart, as indicated (50, 100, or 150 µg), and were challenged after an 8 week rest period. (Fisher's Exact Test; ****$P \leq 0.0001$)

Trimer-1 showed excellent immunogenicity (FIG. 8) and efficacy against systemic challenge with APEC-280 isolate at both the 3 and 8 week resting periods following challenge (Table 12, FIGS. 5 and 7). Trimer-2 was also immunogenic (FIG. 8) and showed protection after a 3 week resting period following challenge (Table 12, FIG. 6); it was not tested after an 8 week resting period. When the challenge was administered 3 weeks post second vaccination, the results showed statistically significant protection over the placebo controls for both Trimer-1 and Trimer-2 at multiple dose levels; groups A-I (Table 12; FIGS. 5 and 6). Trimer-1 of group C at the 150 μg dose level was highly efficacious showing a percent survival of 93%, having only 1 out of 15 mice die. Trimer-1 of group E at the 50 μg dose level was the only group that was not statistically significant, showing only a 20 percent survival (Table 12; FIG. 5). In addition, protection was directly correlated to the dose of the Trimer-1 protein as illustrated in FIG. 5. As demonstrated, a well-defined dose response can be seen with Trimer-1: as the concentration of antigen decreased from 150 μg to 50 μg, mortality increased (Table 12 and FIG. 5). By comparison, mice (15 out of 15) in the placebo controls (group A) died within 48 hours after challenge (Table 12).

Trimer-2 was also efficacious when challenged at 3 weeks post second vaccination. FIG. 6 shows the percent survival for the Trimer-2 recombinant vaccine (groups G-I). All three doses of Trimer-2 showed a statistically significant difference in the overall mortality compared to the placebo controls.

The difference in these results between Trimer-1 and Trimer-2 could possibly be due to random chance or variation in the animal model at the time of challenge.

In this study, we compared the duration of immunity for Trimer-1 following challenge at both 3 and 8 week resting periods. The efficacy observed after an 8 week resting period was similar to that of the 3 week resting period, with the top two doses of 150 and 100 ug reaching statistical significance (FIG. 7).

Example 22

Serology Results

Figure 8A:
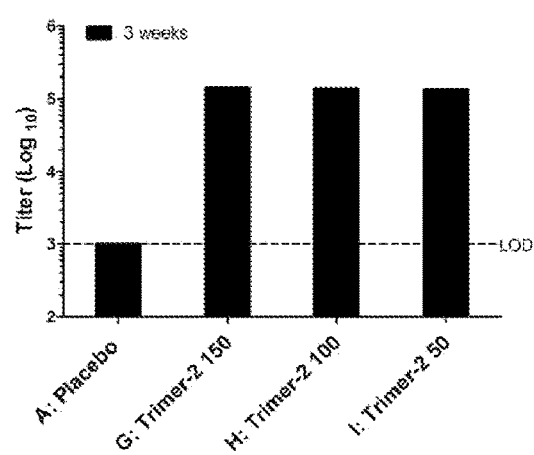
FIGS. 8A-B show serum IgG titers.
Figure 8B:
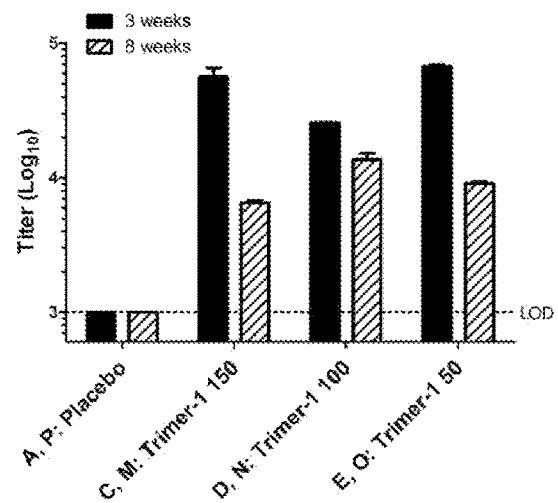

FIGS. 8A and 8B show a comparison of the antibody response to vaccination for Trimer-2 after a 3 week resting period and Trimer-1 after the 3 and 8 week resting periods. Mice were bled at 24 hours pre-challenge. The serological response to vaccination was analyzed in pooled serum using by the ELISA of Example 12, with the vaccine antigen (Trimer-1 or Trimer-2) coated on the plate. Trimer-2 induced high levels of serum IgG that were comparable regardless of the dose (FIG. 8A). Trimer-1 also induced an antibody response to the protein without a clear dosage effect (FIG. 8B). The results show a declining titer from the 3 to 8 week resting periods for each dose of Trimer-1 administered; (FIG. 8B). This is likely due to a natural decline over the 3 to 8 week time period after the second vaccination was administered. However; this decline in antibody titer did not correlate with a decrease in efficacy; since there was no statistical difference in protection from the 3 week compared to the 8 week resting period at the two optimal doses given (100 μg and 150 μg) (Table 12; FIGS. 5, 6, and 7). However, this was not the case for mice vaccinated with the 50 μg dose level even though there was a comparable antibody response to vaccination; mortality increased as the vaccine dose decreased from 150 μg to 50 μg total protein. The lack of efficacy in mice vaccinated with the 50 μg dose level indicates that protection is not completely dependent on an antibody response but may also be driven by a cell-mediated response.

Example 23

Mucosal Immunization with Trimer-1

The mucosal surface is a primary site of infection for many bacteria, including gram-negatives, whose portals of entry include the gastrointestinal tract, lung, and urinary tract. A protective immune response that includes IgA production at the mucosal surface may be critical to the design of an effective vaccine against these types of infections. However, mucosal delivery of protein antigens can be challenging in terms of protecting the antigen and enhancing its translocation to mucosa-associated lymphoid tissue. To circumvent these difficulties, a variety of delivery systems and mucosal adjuvants have been developed. Nonetheless, there is currently no way to predict whether a protein will be taken up and presented in manner that will induce a strong mucosal immune response. To test this capability, vaccines were administered intranasally using a formulation that contained cholera toxin (CT), which is an adjuvant known to promote a mucosal immune response.

Female CBA/J mice (The Jackson Laboratory, Bar Harbor, Me.) were received at 5-6 weeks of age and acclimated for 1 week prior to immunization. Mice were housed under SPF conditions at 5 mice per cage with food and water supplied ad libitum. Three immunizations of 100 μg given two weeks apart were administered in a total volume of 20 delivered intranasally (IN) at 10 μl/nare (Table 13). The vaccine antigens were diluted in PBS and admixed with cholera toxin to yield 2 μg/dose. Ovalbumin, which has been used as a model antigen by many researchers and is capable of inducing a mucosal response, was included as a comparator. Blood and urine were harvested at 2 weeks after the third vaccination and evaluated for IgG by ELISA, performed as described in Example 12 above. A HRP-conjugated goat anti-mouse IgA, heavy-chain specific secondary antibody (Jackson Immunoresearch), was substituted in the procedure to quantify levels of IgA.

TABLE 13

Experimental design for mucosal immunization with Trimer-1.

| Immunizing antigen(s) | Mice (N) | Antigen/ dose (μg) | Adjuvant | Vaccine volume (μl) | # Vax | Route |
|---|---|---|---|---|---|---|
| Placebo | 5 | NA | 2 ug CT | 20 | 3 | IN |
| Ovalbumin | 5 | 100 | 2 ug CT | 20 | 3 | IN |
| Trimer-1 | 5 | 100 | 2 ug CT | 20 | 3 | IN |

Example 24

Serology Results

Levels of IgG in serum were approximately three times higher for ovalbumin compared with Trimer-1, but a good response was observed against both antigens (Table 14). The level of serum IgA produced against Trimer-1 was comparable to that of ovalbumin. In urine, Trimer-1 induced slightly higher levels of IgA and comparable levels of IgG. No antibodies to ovalbumin or Trimer-1 were detected in the placebo. The results indicate that Trimer-1 is capable of inducing a mucosal immune response that is comparable to that of a model antigen such as ovalbumin.

TABLE 14

IgG and IgA produced in serum and urine in response to intranasal (IN) vaccination with Trimer-1.

| Immunizing antigen(s) | Dose (ug) | Adjuvant | Target protein in ELISA | IgG Serum | IgG Urine | IgA Serum | IgA Urine |
|---|---|---|---|---|---|---|---|
| Placebo | NA | CT | Ovalbumin; Trimer-1 | ND | ND | ND | ND |
| Ovalbumin | 100 | CT | Ovalbumin | $9.5 \times 10^4$ | 18 | $1.2 \times 10^3$ | 142 |
| Trimer-1 | 100 | CT | Trimer-1 | $3.1 \times 10^4$ | 14 | $2.0 \times 10^3$ | 229 |

ND, not detected

Example 25

Mucosal Immune Response and Protection Against Urinary Tract Infection by Different Formulations of Trimer-1

The objective of this study was to evaluate a variety of formulations and prime-boost immunization regimens to evaluate the potential of Trimer-1 to induce a mucosal immune response and also to protect against *E. coli* urinary tract infection (UTI). The adjuvant formulations used for the prime (first vaccination) and boost (second, third, and fourth vaccinations) is shown in Table 15. Cholera toxin (CT) and double-mutant labile toxin (dmLT) are well-established mucosal adjuvants and were employed for IN vaccinations only. Squalene forms an oil in water nanoemulsion and has been used for both mucosal and systemic vaccination, while aluminum hydroxide is typically used only for the systemic route. Monophosphoryl lipid A (MPLA) is a TLR4 agonist capable of causing a shift to a Th1 type of immune response.

TABLE 15

Prime and boost adjuvants used to test induction of a mucosal response and protection against urinary tract infection.

| Group | Prime Adjuvant | Prime Route | Boost Adjuvant | Boost Route |
|---|---|---|---|---|
| A | None (PBS) | IN | None (PBS) | IN |
| C | Cholera toxin (CT) | IN | CT | IN |
| E | CT + squalene (50%) | IN | CT + squalene (50%) | IN |
| G | Double-mutant labile toxin (dmLT) | IN | dmLT | IN |
| H | Aluminum hydroxide (20%) (AlOH) | SC | CT | IN |
| I | AlOH + monophosphoryl lipid A (MPLA) | SC | CT | IN |
| J | Squalene | SC | CT | IN |

TABLE 16

Experimental Design.

| Group | Mice (N) | Vaccine | Total Antigen/ Dose (µg) | Adjuvant | Vaccine Volume (µl) | # Vax | Rest Period | Challenge Strain |
|---|---|---|---|---|---|---|---|---|
| A | 3 | PBS (Placebo) | N/A | See Table 15 | 20 | 4 | 3 | UPEC-25 |
| C | 5 | Trimer-1 | 100 | | 20 | 4 | 3 | UPEC-25 |
| E | 4 | Trimer-1 | 100 | | 20 | 4 | 3 | UPEC-25 |
| G | 5 | Trimer-1 | 100 | | 20 | 4 | 3 | UPEC-25 |
| H | 4 | Trimer-1 | 100 | | 20 | 4 | 3 | UPEC-25 |
| I | 5 | Trimer-1 | 100 | | 20 | 4 | 3 | UPEC-25 |
| J | 5 | Trimer-1 | 100 | | 20 | 4 | 3 | UPEC-25 |

Female C3H/HeOuJ mice (The Jackson Laboratory) were received at 5-6 weeks of age and acclimated for 1 week prior to immunization. Mice were housed under SPF conditions at 5 mice per cage with food and water supplied ad libitum. Mice were immunized with 100 µg of Trimer-1 four times, with two weeks between each of the first three vaccinations and a four week interval between the third and fourth vaccinations. All vaccines were formulated and administered as described in Tables 15 and 16. The compositions included CT (Sigma, St. Louis, Mo.) at 2 µg/dose, dmLT (provided by John Clements, Tulane University, New Orleans, La.) at 2 µg/dose, squalene (Addavax; InvivoGen, San Diego, Calif.) prepared according to the manufacturer's recommendations at a final concentration of 50% (v/v), AlOH (ALHYDROGEL, InvivoGen) at a final concentration of 20% (v/v), and MPLA (InvivoGen) at 10 µg/dose. Subcutaneous (SC) immunizations were injected in a 100 µl volume, and IN immunizations were administered in a 20 µl volume (10 µl per nare).

IgG and IgA titers were evaluated by ELISA in serum, urine, and feces at two weeks after the fourth vaccination (Week 10). Blood was processed for serum and urine was collected over a period of 2-3 days. Fecal pellets were suspended in 150 µl/pellet of PBS containing a protease inhibitor cocktail, 1% bovine serum albumin, 0.05% Tween 20, 50% glycerol, 0.1% sodium azide. Pellets were processed by vortexing to obtain a homogenous slurry. Solid debris was removed by centrifugation at 12,000×g for 5-10 minutes, and the supernatant was retained for testing. All serum, urine, and fecal samples were stored at −20° C. until they were tested by ELISA (Example 12).

The mice were challenged after a 3 week rest period. In brief, mice were anesthetized with ketamine/xylazine, the bladder was catheterized using sterile polyethylene tubing (BD INTRAMEDIC™ polyethylene tubing, 0.28/0.61 mm inner/outer diameter) 1 inch in length. A 20 µl volume of bacteria was administered transurethrally (TU) using a syringe infusion pump at a rate of 1 µl per second. To increase the percentage of naïve control mice that develop chronic infection of the bladder and kidney, the challenge was delivered in two doses as a primary infection followed by superinfection containing the same number of CFU, which was delivered within 1-2 hours of the primary infection.

At 7 days after infection, the bladder and left kidney were harvested and homogenized in 200 µl and 400 µl, respectively, of PBS. Ten-fold dilutions of the homogenates were plated on Levine EMB agar and incubated at 37° C. overnight. The colonies were counted and expressed as the total CFU per bladder or kidney. Based on the dilution scheme, the calculated limit of detection (LOD) was 8 CFU for bladder and 16 CFU for kidney.

Example 26

Preparation of Challenge Organism for UTI

UPEC-25 is a clinical isolate of E. coli obtained from a patient with a urinary tract infection. Frozen stocks of UPEC-25 were prepared as follows. The isolate was plated onto blood agar and incubated at 37° C. overnight. A single colony was inoculated into 25 ml TSB followed by overnight incubation at 37° C. with agitation at 250 rpm. The next day, the organism was subcultured at a 1/100 dilution into TSB and incubated at 37° C. with agitation at 250 rpm. Growth was monitored every 1-2 hours using a spectrophotometer at a wavelength of 600 nm. At an OD of 0.6-0.8, the cells were pelleted by centrifugation at 5,000×g (4° C.) for 10 minutes. The supernatant was removed, and the cell pellet was resuspended in the original culture volume of PBS, followed by centrifugation at 5,000×g (4° C.) for 10 minutes. After removing the supernatant, the pellet was resuspended at one-tenth the original volume in TSB containing 20% glycerol, distributed into cryovials, and immediately frozen and stored at −80° C.

The challenge dose for UTI was prepared as follows. On Day 1, a cryovial aliquot was thawed quickly and mixed by vortexing, and a 20 µl volume was transferred into 10 ml LB broth in a 50 ml conical tube. The culture was incubated without agitation (i.e., stationary) at 37° C. for 20-24 hours. On Day 2, 10 µl of the culture was subcultured into 10 ml LB broth and incubated without agitation, overnight at 37° C. On Day 3, the 10 ml culture was transferred into a 1 L flask containing 500 ml pre-warmed LB broth, incubated under stationary conditions at 37° C., and allowed to grow to an OD of approximately 0.6, which typically occurred over a 2-3 hour period. The cells were harvested by centrifugation for 10 minutes at 5,000×g, 4° C., and resuspended in an appropriate volume of sterile PBS to achieve the targeted challenge dose in a volume of 20 µl. The actual challenge dose delivered was determined by serial dilution and plating on EMB agar.

Example 27

Challenge Results

All vaccinated groups showed protection against urinary tract infection at 7 days after challenge with UPEC-25, regardless of the adjuvant or vaccination regimen (FIGS. 9A and 9B). The challenge dose was $8.5 \times 10^7$ CFU for both the primary and superinfection. The median level of colonization in the bladder was reduced by nearly two logs or more, and in group E, no bacteria were recovered from two of four mice, indicating the infection had cleared. One of three mice in group H also cleared the infection. Results in the kidney paralleled those in the bladder, suggesting that Trimer-1 was capable of protection against cystitis as well as pyelonephritis using a variety of vaccine formulations and regimens.

Example 28

Serology Results

IgG and IgA titers in serum, urine, and feces are shown in FIGS. 10A, B and C, respectively. Trimer-1 induced serum IgG to titers greater than $1 \times 10^4$ in all six vaccine formulations. Serum IgA was also produced, at lower levels that were comparable across all six immunized groups. Little to no IgG could be detected in urine, whereas IgA was detected in all groups. Fecal IgG was detected only in group I, which was primed with a mixture of AlOH and MPLA. Fecal IgA was produced in groups H and I, both of which were primed with a formulation containing AlOH. The results reinforce the previous observations from Example 24 that Trimer-1 is capable of inducing a mucosal immune response, as demonstrated by IgA in serum, urine, and feces. They also extend this observation to a variety of different formulations, some of which are capable of inducing measurable levels of fecal IgA and/or IgG.

Example 29

Increased Immune Response and Protection Against Urinary Tract Infection with Escalating Doses of Trimer-1

C3H/HeOuJ mice were immunized with the group E formulation of CT+squalene as described in Example 25. The vaccine formulation contained either 25, 100, or 200 µg of Trimer-1 per dose (Table 17). The vaccines were administered IN at 10 µl/nare, with the highest dose of 200 µg administered in two successive rounds of immunization. Mice received four vaccinations, two weeks apart, with a two week rest period before challenge. Blood, urine, and feces were collected after the fourth vaccination, just prior to challenge. These samples were processed individually and evaluated for serology as described previously in Example 25. Mice were challenged with UPEC-25 and processed for CFU in the bladder and kidney as described in Examples 25 and 26.

TABLE 17

Experimental Design.

| Group | Mice (N) | Vaccine | Total Antigen/dose (μg) | Adjuvant | Vaccine Volume (μl) | # Vax | Vaccine Route | Rest Period (weeks) | Challenge Strain |
|---|---|---|---|---|---|---|---|---|---|
| A | 14 | PBS | N/A | N/A | 20 | 4 | IN | 2 | UPEC-25 |
| B | 12 | Trimer-1 | 25 | CT + squalene | 20 | 4 | IN | 2 | UPEC-25 |
| C | 12 | Trimer-1 | 100 | CT + squalene | 20 | 4 | IN | 2 | UPEC-25 |
| D | 12 | Trimer-1 | 200 | CT + squalene | 2 × 20 | 4 | IN | 2 | UPEC-25 |

Example 30

Challenge Results

Mice received a challenge dose of 2.5×10$^6$ CFU for both the primary and superinfection. At seven days after infection, vaccinated mice showed reduced colonization in the bladder (FIG. 11A). All three vaccinated groups had a positive mitigated fraction, indicating the fraction of vaccinates that had reduced CFU relative to the placebo. This was statistically significant for the 100 μg dose. The median level of colonization was reduced by more than three logs in the bladder for both the 100 μg and 200 μg doses, and colonization correlated with the vaccine dose. In the kidney, vaccination also mitigated colonization in all three groups, with both the 25 μg and 200 μg doses reaching significance (FIG. 11B). The reduction in colonization observed at the 100 μg dose was greater than that shown in Example 27, further substantiating the protective capacity of Trimer-1 in larger numbers of animals.

Example 31

Serology Results

Levels of IgG in serum and urine increased in parallel with the immunizing dose of Trimer-1 (FIG. 12A, B). Serum, urine, and fecal IgA showed a similar, dose-related trend, with the highest level observed for the 200 μg dose (FIG. 12A, B, C). Levels of antigen-specific IgG and IgA in serum, urine, and feces were below the limit of detection in the placebo (data not shown). These data further support the concept that Trimer-1 induces a mucosal immune response as indicated by IgA production in serum and feces as well as in urine, demonstrating that a mucosal response was present locally, at the site of infection.

Example 32

Hyper-Immunization of Holstein Steers with Trimer-1 and Preparation of Polyclonal Antibody Four 4-month-old Holstein Steers identified by ear tags were divided into two equal groups designated as Groups A (Tag numbers-141, 38) and Group B (Tag numbers-143, 50). Steers were vaccinated subcutaneously four times at 21 day intervals using Trimer-1 prepared in two different adjuvants: aluminum hydroxide and ENABL C3 (Vaxliant, Omaha, Nebr.). The vaccine of Group A was prepared using 400 μg per dose of total protein in PBS, formulated with 20 percent REHYDRAGEL HPA (General Chemical; Berkeley Heights; New Jersey) in a final injectable volume of 2 ml. The antigen/aluminum hydroxide suspension was stirred for 24 hours at 4° C. to allow maximum adsorption of the protein to the adjuvant.

The vaccine of Group B was prepared using 400 μg of total protein per dose in PBS, formulated with 20% ENABL C3 (Vaxliant Omaha, Nebr.) in a final injectable volume of 2 ml.

Twenty one days after the fourth vaccination, 2.0 liters of blood from each steer was pooled separately and allowed to clot at 4° C. for 24 hours. The serum was separated from whole blood by centrifugation at 3000×g for 30 minutes. The serum; approximately 800 ml per sample was again centrifuged at 10,000×g for 30 minutes to remove any contaminating cell debris and then aliquoted into 25 ml volumes in sterile 50 ml conical tubes (Fisher Scientific) and frozen at −80° C. until use. Serum titers were evaluated by ELISA as described in Example 12 with Trimer-1 coated on the plate and using a goat anti-bovine IgG HRP-conjugate (Jackson Immunoresearch) as the secondary. Each calf responded immunologically to vaccination generating high titers after the fourth vaccination.

FIG. 13 shows the immunological response of calves (#38 and #141) of group A to antigen-specific IgG antibodies as analysed by ELISA demonstrating that Trimer-1 is immunogenic in cattle. Titers for individual animals were determined pre- and post-vaccination. (LOD, limit of detection).

Example 33

Cross-Reactivity of Antibodies with Membrane Proteins from *Klebsiella pneumoniae* and Multiple Strains of *E. coli*

The hyperimmunized serum of Group B produced against the Trimer-1 protein of Example 32 was used to evaluate cross-reactivity with membrane-associated antigens of bacteria from different genera and species. Membrane proteins were derived from *Klebsiella pneumoniae* of bovine origin, *E. coli* CFT073 of human origin and an Avian Pathogenic *E. coli* isolate designated as APEC-280. The outer membrane protein profiles were examined by SDS-PAGE. Briefly, each of the isolates to be examined was inoculated into TSB containing 300 μM 2,2-dipyridyl and incubated at 37° C. Following incubation for 12 hours, the cultures were sub-cultured (1:100) into 500 ml of the same media and incubated at 37° C. After 8 hours each culture was centrifuged at 10,000×g for 20 minutes, resuspended in 40 ml of osmotic shock buffer (7.3 g/l Tris Base; 1.86 g/l EDTA, pH 8.9), and disrupted by sonication, to yield a suspension. The suspensions were centrifuged at 32,000×g for 12 minutes to clarify or remove large cellular debris. The supernatants were collected and solubilized by the addition of 4% sodium lauroyl sarcosinate at 4° C. for 24 hours. The outer membrane protein-enriched fractions were collected by centrifugation at 32,000×g for 2.5 hours at 4° C. The protein pellets were resuspended in 200 µl Tris-buffer (pH 7.2).

The purified extracts of each isolate were subjected to electrophoresis followed by western blot analysis using the Trimer-1 hyper-immunized serum of group B (as described in Example 32). In brief, the outer membrane preparations were size-fractionated on an SDS-PAGE gel using a 4% stacking gel and 7.5% resolving gel. A 10 µl sample of the outer membrane fraction was combined with 10 µl of SDS reducing sample buffer (62.5 mM Tris-HCL ph 6.8, 20% glycerol, 2% SDS, 5% β-mercaptoethanol) and boiled for 4 minutes. Samples were electrophoresed at 18 mA constant current for 5 hour at 4° C. using a Protein II xi cell and model 1000/500 power supply (BioRad Laboratories, Richmond, Calif.). FIG. 14A shows the electrophoretic outer membrane protein profiles for each isolate examined (lane 1-Molecular Weight Marker, Lane 2-Blank, Lane 3-*Klebsiella pneumoniae*, lane 4-*E. coli* APEC 280, lane 5-*E. coli* CFT073 and lane 6-blank).

Western blot analysis revealed that the Trimer-1 positive antisera reacted against multiple membrane-associated proteins of *Klebsiella pneumoniae* (lane 3), *E. coli* APEC-280 (lane 4) and *E. coli* CFT073 (lane 5) (FIG. 14B). These results suggest that antibody produced in response to the Trimer-1 protein cross-reacts with proteins from different genera and species of gram-negative bacteria.

Example 34

Efficacy of Trimer-1 as a Therapeutic Agent Against an Existing Infection of Virulent *E. coli* in a Mouse UTI Model The therapeutic efficacy of recombinant Trimer-1 was evaluated using a live virulent *E. coli* challenge with UPEC-25 in mice, with colonization of the bladder and kidney as the endpoint. The outcome parameters used to evaluate vaccine efficacy against UPEC-25 were 1) level of colonization in bladder and kidney at 14 days post-infection, and 2) correlation of antibody titers with survival.

Briefly, 30 female C3H/HeOuJ mice obtained from Jackson Laboratory (Bar Harbor, Me.) at 5-6 weeks of age were equally divided into 2 treatment groups (n=15 mice/group) designated as indicated (Table 18). Mice were vaccinated five times at 1 to 3 day intervals after being challenged with UPEC-25 at Day 0. Mice were housed in polycarbonate cages (Ancore Corporation, Bellmore, N.Y.) at 5 mice per cage with food and water supplied ad libitum. All mice were allowed to acclimate one week prior to the first vaccination.

Example 35

Vaccine Preparation and Vaccination

Vaccines contained Trimer-1 or adjuvant-only placebo. Trimer-1 was used to determine duration of therapeutic immunity (DOI) at 2 weeks post initial infection. Vaccines were prepared by combining 100 µg Trimer-1 in phosphate buffered saline PBS formulated with 2 µg double mutant heat labile toxin (dmLT) per dose in a final volume of either 0.1 ml (for SC prime immunization, including 20 percent [v/v] ALHYDROGEL [Invivogen, San Diego, Calif.]) or 0.02 ml (for IN immunization, including 50 percent [v/v] squalene [Addavax, Invivogen, San Diego, Calif.]) (Table 18). The placebo vaccines were prepared by substituting PBS for the aqueous protein suspension as described in the above procedure. Mice were vaccinated five times in total. The first vaccination was a dual vaccination at day 1 post challenge during which each mouse received one subcutaneous and one intranasal vaccination on the same day. Thereafter, mice received only a single intranasal immunization per day, starting at day 4, and repeating at 1 day intervals for three days in total (i.e., on Day 4, 5 and 6). Blood was collected from both groups on the day before challenge and at 10 days post challenge.

Example 36

Preparation of Challenge Organism

UPEC-25 is a clinical isolate of *E. coli* obtained from a patient with a urinary tract infection. The frozen stock and challenge culture of UPEC-25 were prepared as described previously in Example 26.

Example 37

Challenge Results

All mice in groups A-B were transurethrally challenged with 0.02 ml containing $1.4 \times 10^6$ colony forming units (CFU) of the virulent UPEC-25 isolate as described in Example 25, to evaluate the protective efficacy of the Trimer-1 vaccine. Colonization of the bladder and kidney were evaluated by sacrificing mice at 2 weeks post-infection and enumerating bacteria in the tissue by plating tissue homogenates on selective media.

Trimer-1 showed excellent efficacy and immunogenicity in reducing colonization following transurethral challenge with UPEC-25 isolate at 2 weeks following challenge. The reduction in colonization of both bladder (FIG. 15A) and

TABLE 18

Experimental Design.

| Group | Mice | Vaccine | Total Antigen (µg) | Adjuvant | Vaccine Volume (ul) | # Vax | Vaccine Route | Challenge Strain |
|---|---|---|---|---|---|---|---|---|
| A | 15 | PBS | N/A | AlOH + dmLT | 100 | 1 | SC | UPEC-25 |
|   |   |   |   | squalene + dmLT | 20 | 4 | IN |   |
| B | 15 | Trimer-1 | 100 | AlOH + dmLT | 100 | 1 | SC | UPEC-25 |
|   |   |   |   | squalene + dmLT | 20 | 4 | IN |   | kidney (FIG. 15B) in group B (immunization with Trimer-1) was significant by mitigated fraction in comparison with group A (placebo). These data indicate that Trimer-1 immunization of an animal with a pre-existing urinary tract infection can significantly reduce bacterial colonization in both the bladder and the kidney of the infected animals.

Example 38

Serology Results

FIGS. 16A-B show the antibody response to vaccination with Trimer-1 for serum IgG1 and 2a subclasses (panel A) and IgA in serum, and secretory IgA in urine (panel B). Mice were bled at 24 hours before challenge, and titers in pre-immune serum were at baseline, similar to the placebo titers shown in the panel. Blood and urine were also collected on Day 11, for which the results are shown. The serological response to vaccination was analyzed in individual serum and urine samples using the ELISA method of Example 12, with the vaccine antigen (Trimer-1) coated on the plate. Trimer-1 induced an antibody response to the protein, including production of serum IgG1, IgG2a, and IgA (panels A and B), and secretory IgA (panel B) in the urine. Some of the placebo mice showed production of secretory IgA to Trimer-1 in urine, in response to the infection (panel B).

Example 39

Synthesis, Cloning, Expression, and Purification of Trimer-3, Trimer-4, and Monomer-1

The DNA coding and polypeptide sequences for Trimer-3 (SEQ ID NO:25 and 26), Trimer-4 (SEQ ID NO:27 and 28), and Monomer-1 (SEQ ID NO:29 and 30) were synthesized and cloned as described in Example 3. Trimer-3 was created by replacing the B cell domains of Trimer-1 with those of Trimer-2, yielding a polypeptide with the B cell domains of Trimer-2 and the T cell domains of Trimer-1. Similarly, Trimer-4 was created by replacing the B cell domains of Trimer-2 with those of Trimer-1. An additional construct, Monomer-1, consisted of module II (SEQ ID NO: 4) with a His tag appended to the N-terminus and GSGS (SEQ ID NO:23) linkers between the B and T cell domains (SEQ ID NO:29 and 30). Recombinant polypeptides Trimer-3, Trimer-4, and Monomer-1 were expressed and purified as described in Example 4.

Example 40

Comparative Immunogenicity of Trimer-1, Trimer-2, Trimer-3, Trimer-4, and Monomer-1

A primary objective of this study was to determine whether exchanging the B cell domains between Trimer-1 and Trimer-2 would generate polypeptides (Trimer-3 and Trimer-4) capable of inducing an immune response. A second objective was to determine if a single module of the MoLE (Monomer-1) would be immunogenic.

Female CBA/J mice were procured and housed as described in Example 25. Mice were distributed into groups, and a blood sample was taken prior to immunization. The prime immunization consisted of a dose of 100 µg antigen formulated in 20% AlOH plus 2 µg dmLT and administered SC (Table 19). Three weeks later, mice were boosted with a dose of 50 antigen formulated in 50% squalene plus 2 µg dmLT and administered IN. Two weeks after the boost a blood sample was obtained, and the level of serum IgG against the immunizing antigen was determined by ELISA (Example 12).

TABLE 19

Experimental Design

| Group | Mice (N) | Immunizing antigen | Total Antigen/ dose (µg) | Adjuvant | Vaccine Route | # Vax | Vaccine Volume (µl) |
| --- | --- | --- | --- | --- | --- | --- | --- |
| B | 4 | Trimer-1 | 100 | AlOH + dmLT | SC | 1 | 100 |
|   |   |   | 50 | squalene + dmLT | IN | 1 | 20 |
| C | 3 | Trimer-2 | 100 | AlOH + dmLT | SC | 1 | 100 |
|   |   |   | 50 | squalene + dmLT | IN | 1 | 20 |
| D | 4 | Monomer-1 | 100 | AlOH + dmLT | SC | 1 | 100 |
|   |   |   | 50 | squalene + dmLT | IN | 1 | 20 |
| E | 4 | Trimer-3 | 100 | AlOH + dmLT | SC | 1 | 100 |
|   |   |   | 50 | squalene + dmLT | IN | 1 | 20 |
| F | 4 | Trimer-4 | 100 | AlOH + dmLT | SC | 1 | 100 |
|   |   |   | 50 | squalene + dmLT | IN | 1 | 20 |

Example 41

Serology Results

Immunization with Trimer-3 or Trimer-4 induced IgG antibody titers that were equivalent to those produced by Trimer-1 or Trimer-2 (FIG. 17). This indicates that immunogenicity of the B cell domains and provision of T cell help was sufficient, regardless of which B and T cell domains were encoded within the trimers. The antibody response to Monomer-1 was slightly but not significantly reduced compared with the trimers and, in particular, Trimer-2, which contains the same B cell domains as Monomer-1. A reduced response to Monomer-1 is not unexpected, considering that Monomer-1 is one-third the size of Trimer-2, and smaller proteins tend to be less immunogenic. Nonetheless, this data indicates that the B and T domains remain highly immunogenic in different combinations within the trimer configuration and also when administered in a smaller, monomer form.

Example 42

Effect of Adjuvant, Route, and Schedule on Serology, T Cell Responses, and Protection Against UTI C3H/HeOuJ mice were procured and housed as described in Example 25. Of the 15 mice per group, 3 were terminated 1 day prior to challenge and used for T cell studies, while the remaining 12 were challenged to determine vaccine efficacy. Mice in Groups B, C, and E were immunized with 100 µg Trimer-1 formulated with the adjuvant according to the routes described in Table 20. Immunized mice were evaluated in parallel with naïve mice as a negative control (Group A). Mice in Groups B and C received a total of four vaccinations two weeks apart with a two week rest. Group E was vaccinated twice, four weeks apart, with a four week rest. Blood and urine were collected after the last vaccination, just prior to challenge. Samples were processed individually (Example 23) and evaluated by ELISA as described in Example 12, with several modifications. Serum and urine IgA were measured using an anti-heavy chain IgA-specific HRP conjugate, and the samples were tested at a single dilution (1:100 for serum and 1:10 for urine) and were reported directly as optical density (OD). Mice were challenged with UPEC-25 and processed for CFU in the bladder and kidney at 14 days post-infection using methodology described in Examples 25 and 26.

Mice used for T cell studies were euthanized, and their spleens were removed and processed to lyse red blood cells. Splenic lymphocytes ($1 \times 10^6$ cells in 0.2 ml RPMI-1640 containing 10% fetal bovine serum) were cultured with 12.5 µg of antigen for 48 hours, and the release of cytokines into cell supernatants was measured according to the manufacturer's protocol (BD Cytometric Bead Array (CBA), BD Biosciences, San Jose, Calif.). For intracellular cytokine staining (ICS), splenocytes were cultured at $2 \times 10^6$ cells/well and stimulated with antigen for 6 hours. The antigen consisted of 12.5 µg Trimer-1 for CBA and ICS and also a mixture of the corresponding T cell domains from Trimer-1 for CBA. Transport was blocked by the addition of brefeldin (GolgiPlug) for 2 hours, after which cell fixation/permeabilization and staining was performed according to the manufacturer's protocol (BD Biosciences, San Jose, Calif.). Cells were analyzed by flow cytometry (FACSCanto, BD Biosciences, San Jose, Calif.) with a gating strategy to exclude B220/CD45r+, CD11c+, and CD11b+ cells and determine the percentage of antigen-specific CD3+CD4+ CD44+ and CD3+CD8+CD44+ T memory cells producing TNFα and IFNγ. For both CBA and ICS, unstimulated splenocytes served as a negative control, and these values were subtracted to calculate the net response to antigen.

Example 43

Challenge Results

Mice received a challenge dose of $1.8 \times 10^6$ CFU for both the primary and superinfection. At 14 days after infection, Groups B and C, which were immunized via the IN mucosal route and adjuvanted in squalene+dmLT for both the prime and boost (Group B) or the boost only (Group C), showed superior efficacy in terms of the mitigated and prevented fraction compared with a strictly parenteral ID vaccination adjuvanted in AlOH+dmLT (Group E) (FIG. 18). This trend was the same for colonization of both the bladder and the kidney. The median level of colonization in bladder and kidney was reduced by more than 3 logs in the bladder and 2 logs in the kidney for Groups B and C, with both groups registering at or below the LOD. These data provide evidence that use of a mucosal vaccination route may improve the efficacy of a UTI vaccine. They also further support the protective efficacy of Trimer-1 as a vaccine antigen, as demonstrated in Examples 27 and 30, to prevent UTI in this relevant clinical model.

Example 44

Serology Results

Figure 19:
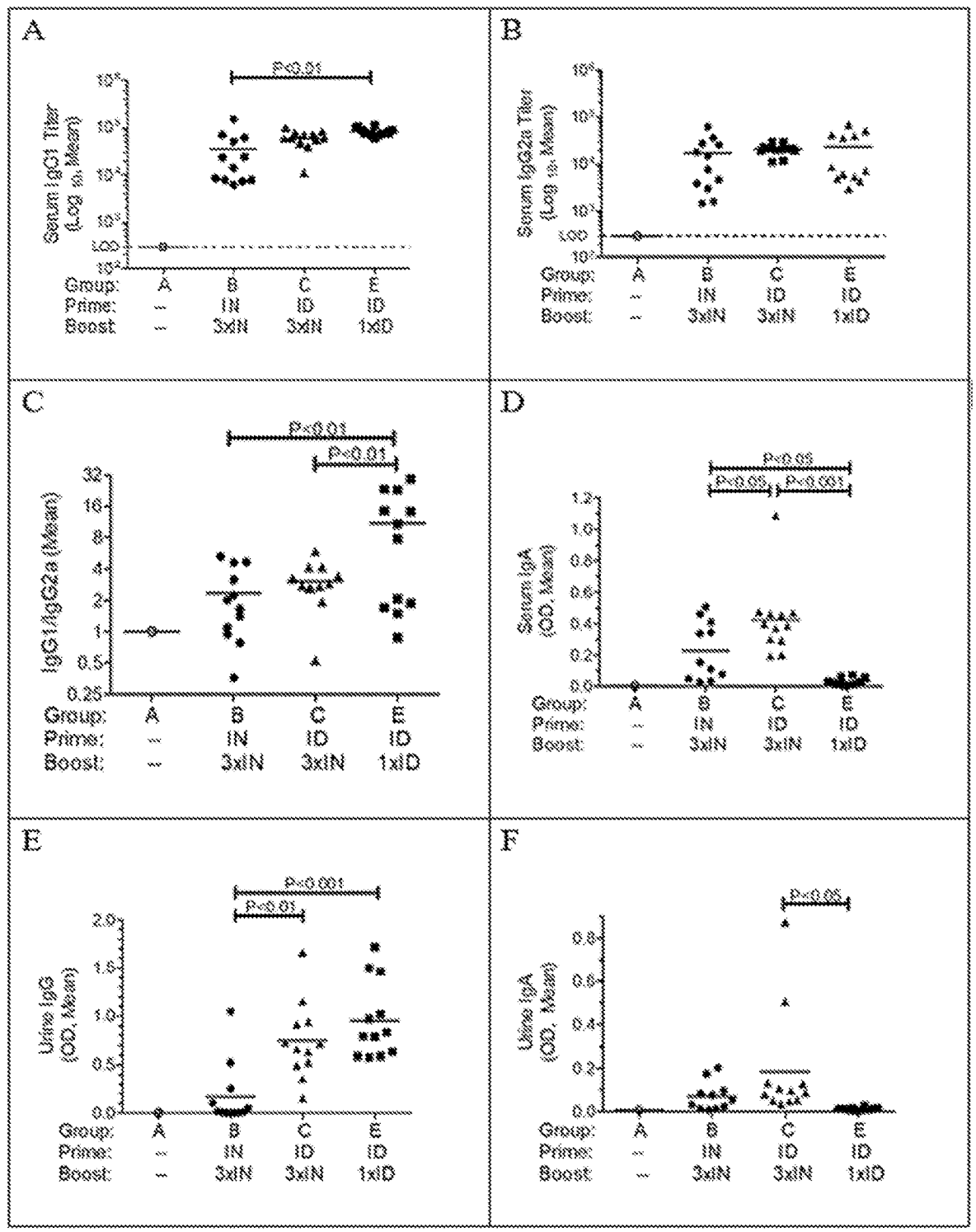

Titers of IgG1 were significantly lower in Group A compared with Group E, but mean IgG2a titers were equivalent, suggesting that class switching occurred in response to vaccination by each of the vaccine regimens used in Groups B, C, and E (FIG. 19). The ratio of IgG1 to IgG2a indicated that the Group B and C regimens induced a more polarized TH1 type of response than the Group E regimen. Differences in the induction of serum IgA were also apparent, with Group C showing the highest response, possibly due to improved delivery or immunogenicity of the ID prime followed by three mucosal IN immunizations. Also evident was the increase in serum IgA in the protected, mucosally-immunized Groups B and C, relative to parenteral immunization in Group E. The association of mucosal immunity with vaccine efficacy was further supported by the levels of IgG and IgA in urine, where IgG is derived from circulating levels in serum and was higher in Group E, but IgA is more likely to be produced locally, due to cellular communication pathways that connect IN exposure to antigen with a localized immune response in the genitourinary tract (Groups B and C). Overall, the serological data indicate that the most effective Trimer-1 vaccines (Groups B and C) corresponded with mucosal delivery initiating a TH1 polarized immune response and production of secretory IgA in urine. Thus, the ability to deliver Trimer-1 and other MoLEs mucosally

TABLE 20

Experimental Design

| Group | Mice (N) | Vaccine | Total Antigen/ Dose (µg) | Adjuvant | Vaccine Volume (µl) | # Vax | Vaccine Route | Rest Period (weeks) | Challenge Strain |
|---|---|---|---|---|---|---|---|---|---|
| A | 15 | None | N/A | N/A | N/A | 0 | N/A | N/A | UPEC-25 |
| B | 15 | Trimer-1 | 100 | Squalene + dmLT | 20 | 4 | IN | 2 | UPEC-25 |
| C | 15 | Trimer-1 | 100 | AlOH + dmLT | 50 | 1 | ID | 2 | UPEC-25 |
|   |   |   |   | Squalene + dmLT | 20 | 3 | IN |   |   |
| E | 15 | Trimer-1 | 100 | AlOH + dmLT | 50 | 2 | ID | 4 | UPEC-25 | appears to be advantageous for initiating an effective immune response at the portal of entry.

Example 45

Results for Development of Antigen-Responsive T Cells

Figure 20:
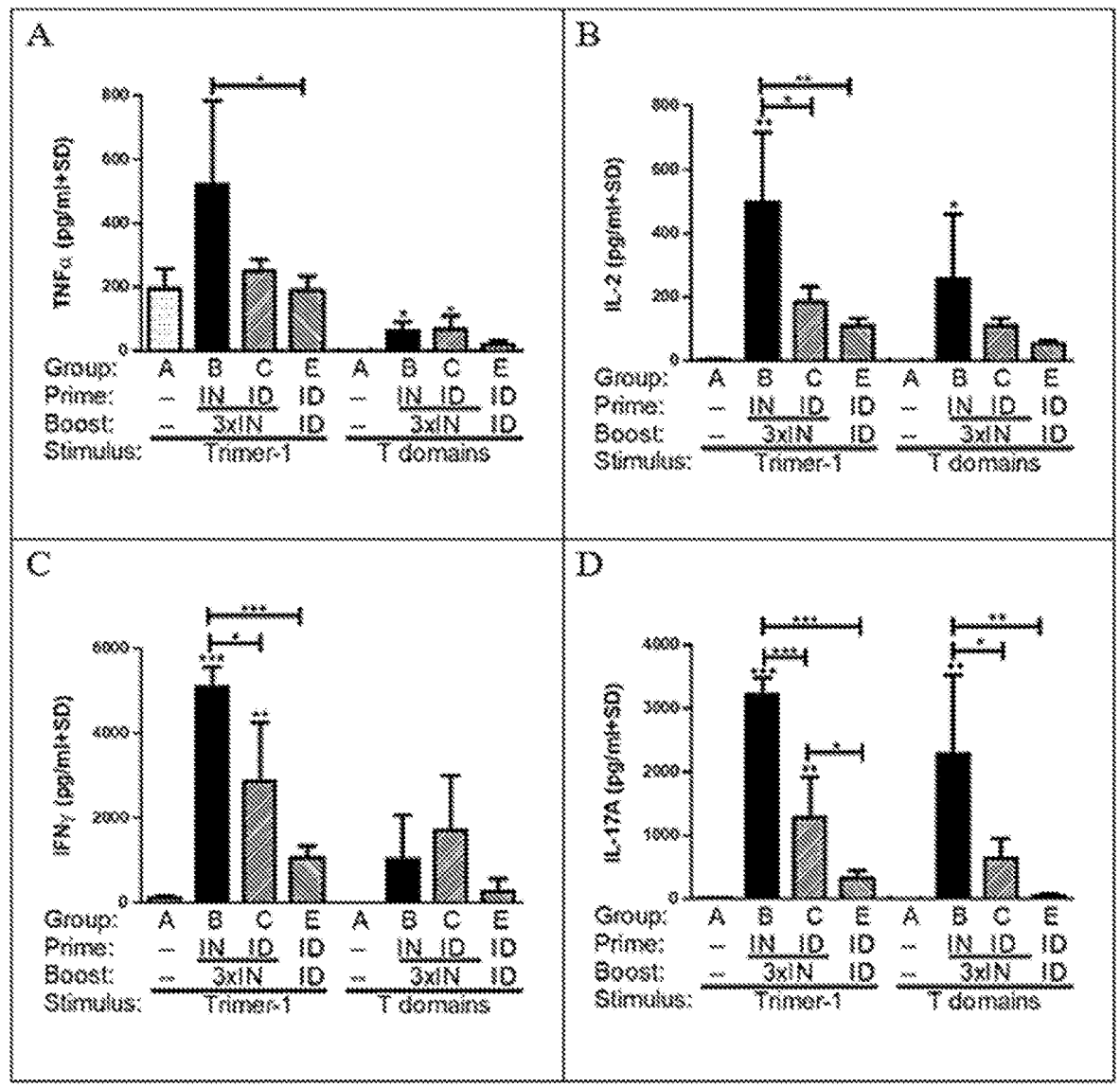

Induction of antigen-responsive T cells was evaluated as a potential indicator of vaccine efficacy. The release of TNFα, IL-2, IFNγ, and IL-17A showed distinct differences among the three vaccinated groups (FIG. 20). Splenocytes were stimulated with Trimer-1 (the vaccine antigen) or a mixture of peptides consisting of the T cell domains used in Trimer-1. In general, responses to intact Trimer-1 were higher but were mirrored by the response to the peptides, establishing that the T cell domains used to construct Trimer-1 were antigenic and were involved in the T cell response to Trimer-1. The strongest responses were observed for the Group B regimen, which corresponded with the greatest level of protection in the challenge study, whereas the weakest T cell responses and protection were observed for Group E (Example 43). TNFα and IL-2 are proinflammatory and stimulate lymphocyte proliferation, respectively. IFNγ and IL-17 promote development of a TH1 response and mucosal immunity, respectively, which corresponds with the TH1 bias and production of secretory IgA shown in Example 44. The provision of T cell help and effector T cell responses through cytokine production is well established as a protective mechanism against infection. The results show that Trimer-1, administered mucosally with an appropriate adjuvant, is capable of inducing significant, antigen-specific T cell responses that are associated with its efficacy as a vaccine antigen.

Example 46

Results for Induction of T Memory Cells

Figure 21:
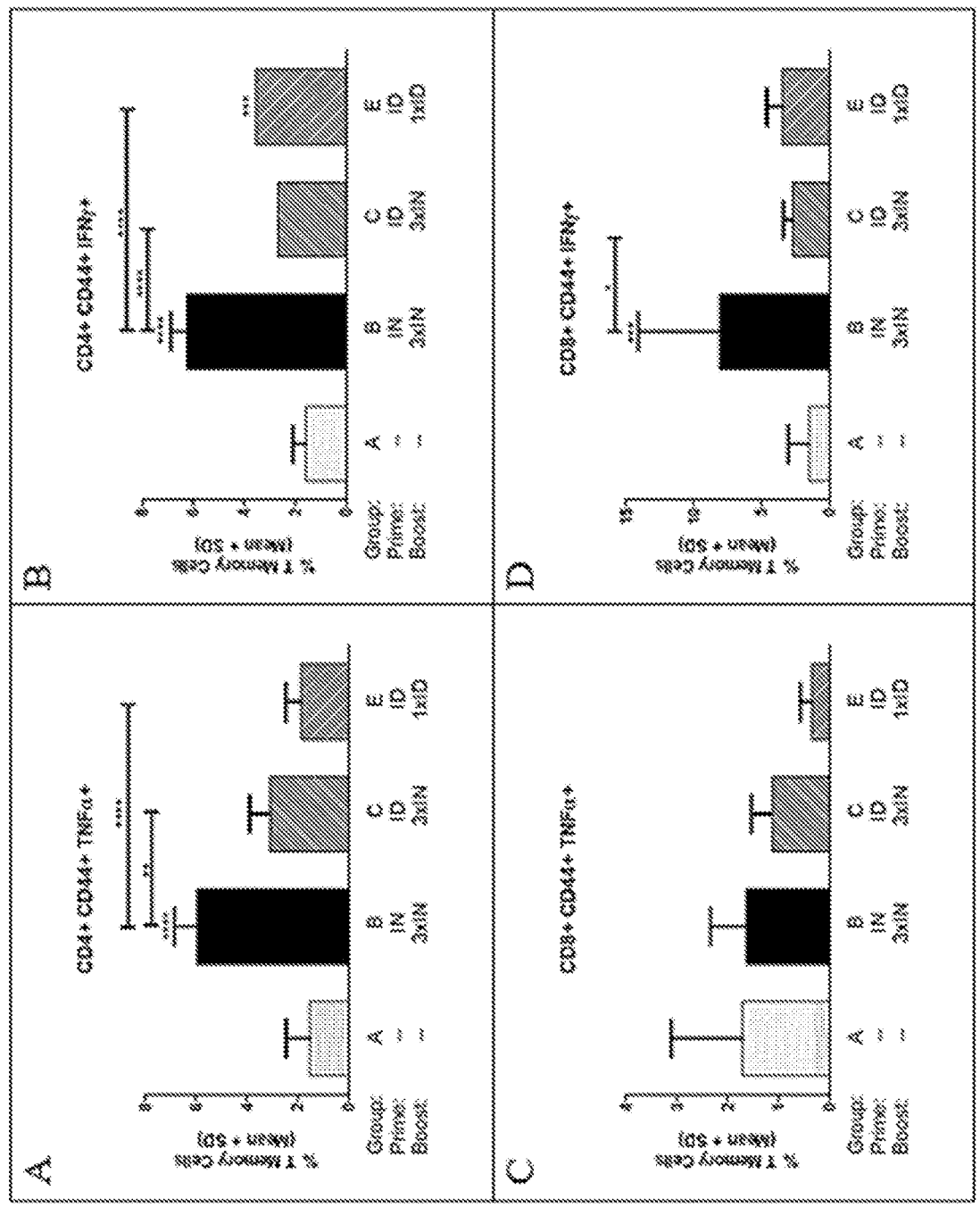

Induction of T memory cells is essential for a vaccine to induce durable, long-term adaptive immunity. In mice, CD44 is a cell surface marker for T memory cells and was used to quantify the level of antigen-specific T memory cells that were induced by Trimer-1 within the CD4 and CD8 subsets (FIG. 21). The Group B vaccine regimen induced the highest percentage of T memory cells in the CD4+ TNFα+, CD4+ IFNγ+, and CD8+ IFNγ+ subsets, and with the single exception of CD4+ IFNγ+ T cells in Group E, it was the only group to show significant levels of T memory cells compared with the naïve control (Group A) and other vaccine groups (C and E). These data further establish the importance of the vaccine regimen and, in particular, the improved efficacy that can be obtained when vaccine antigen such as Trimer-1 is capable of eliciting a mucosal immune response.

Example 47

The Serological Response to Vaccination of Trimer-1 in Turkeys

This experiment evaluated the serological response to vaccination in turkeys vaccinated with Trimer-1. Briefly, sixty (N=60) day of age Nicholas turkey poults (hens obtained from Select Genetics, Willmar Minn.) were placed in an isolation facility, comingled and grown to four weeks of age. Turkeys were vaccinated two times at 21 day intervals and on day 42 (21 days after second vaccination) blood was taken from all birds to evaluate the antibody response to Trimer-1.

Example 48

Vaccine Preparation of Trimer-1

The vaccine containing the recombinant Trimer-1 protein was prepared with 100 μg and 500 μg per dose of total protein in PBS formulated with 25% REHYDRAGEL HPA; (General Chemical; Berkeley Heights; New Jersey) in a final injectable volume of 0.5 ml. The antigen/aluminum hydroxide suspension was stirred for 24 hours at 4° C. to allow maximum adsorption of the protein to the adjuvant. The placebo vaccine was prepared as described above in PBS minus the antigen in the aqueous suspension of the final formulation. The final vaccine formulation was plated on blood agar to determine sterility of the vaccine prior to use.

TABLE 21

Experimental design.

| Group | Turkey | Vaccine | Total Antigen (μg) | Adjuvant | Vaccine Volume | Number of Vaccines | Vaccine Route |
|---|---|---|---|---|---|---|---|
| A | 20 | Placebo | N/A | AlOH | 0.5 ml | 2 | SC |
| B | 20 | Trimer-1 | 100 | AlOH | 0.5 ml | 2 | SC |
| C | 20 | Trimer-1 | 500 | AlOH | 0.5 ml | 2 | SC |

Example 49

Vaccination

At 4 weeks of age all birds were tagged with numbered wing bands and randomly allocated into three equal groups (20 birds per group) designated as Groups A through C. Turkeys in Group A were placebo-vaccinated, while birds in Groups B and C received the Trimer-1 vaccines at 100 μg and 500 μg, respectively. All birds were vaccinated subcutaneously in the lower neck region two times at 21 day intervals. Blood was taken from all birds at first vaccination (pre-immune) and again at 21 days after first vaccination. Serum was collected from coagulated blood and stored at −80° C.

Example 50

Serology Results

The serological response to vaccination was analyzed in pooled serum by ELISA with the vaccine antigen (Trimer-1) coated on the plate and calculated as the geometric mean titer. FIG. 22 shows a comparison of the antibody response to vaccination in Placebo, Trimer-1 at (100 μg), and (500 μg). The results show the serological response to vaccination at 42 days post first vaccination. The vaccines of Trimer-1 at both the 100 μg and 500 μg dose regimens induced IgG antibody, although there was no difference in the antibody response between the two different vaccine doses given.

Example 51

The Serological Response of Vaccination with Trimer-1 in Chickens

This study evaluated the serological response of vaccination of Trimer-1 in chickens. Briefly, twenty (N=20) specific pathogen free Leghorn hens were obtained from Valo BioMedia, (Adel, Iowa) and grown to 7 weeks of age prior to study initiation. The hens were tagged with numbered wing bands, randomly allocated into two equal groups (10 birds per group) designated as Groups A and B and commingled for the duration of the study. Chickens were vaccinated two times at 21 day and on day 42 (21 days after second vaccination) blood was taken from all birds.

Example 52

Vaccine Preparation and Vaccination

The vaccine containing the recombinant Trimer-1 protein was prepared at 200 μg total protein per dose in PBS. The aqueous Trimer-1 suspension was formulated into a water-in-oil emulsion. The composition of the vaccine was: 44.44% antigen suspension in PBS, 50% white mineral oil, 3% Span85 and 2.56% Tween85 to give a dose of 200 μg total protein in an injectable volume of 0.5 ml. The placebo vaccine was prepared by substituting PBS for the aqueous protein suspension of the above described formulation. Chickens in Group A were vaccinated with the placebo vaccine while chickens in Group B received the oil-adjuvanted Trimer-1 vaccine. Birds were vaccinated subcutaneously in the lower neck region two times at 21 day intervals. Blood was taken from all birds at first vaccination (preimmune), 14 days after first vaccination and again at 21 days post first vaccination or at time of challenge. Serum was collected from coagulated blood and split into two duplicate sample sets and stored at −80° C.

preimmune; lane 2, placebo 14 days; lane 3, placebo 28 days; lane 4, Trimer-1 14 days; and lane 5, Trimer-1 28 days). The Trimer-1 protein induced an immune response to vaccination in contrast to the placebo controls.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical

TABLE 22

Experimental design.

| Group | Chicken | Vaccine | Total Antigen (μg) | Adjuvant | Vaccine Volume | Number of Vaccines | Vaccine Route |
|-------|---------|---------|---------------------|----------|----------------|--------------------|---------------|
| A | 10 | Placebo | N/A | Oil Emulsion | 0.5 ml | 2 | SC |
| B | 10 | Trimer-1 | 200 | Oil Emulsion | 0.5 ml | 2 | SC |

Example 53

Serology Results

FIG. 23 shows the serological response to vaccination using Trimer-1 as the capture protein in an ELISA (lane 1, values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A non-natural protein comprising an amino acid sequence having at least 80% sequence identity to the amino acid sequence of SEQ ID NO:5 or SEQ ID NO:6.

2. A non-natural protein comprising an amino acid sequence having at least 80% sequence identity to the amino acid sequence of SEQ ID NO:3 or SEQ ID NO:4.

3. The protein of claim 2 wherein the protein further comprises two or more copies of the amino acid sequence, wherein the two or more copies are present as a tandem repeat.

4. The protein of claim 2 wherein the protein comprises at least three copies of the amino acid sequence, wherein the three or more copies are present as a tandem repeat.

5. A non-natural protein comprising amino acids 7-518 of the amino acid sequence of SEQ ID NO:8 or amino acids 7-365 of the amino acid sequence of SEQ ID NO:10.

6. A composition comprising the protein of claim 1.

7. The composition of claim 6 further comprising a pharmaceutically acceptable carrier.

8. The composition of claim 6 further comprising an adjuvant.

9. A composition comprising the protein of claim 2.

10. The composition of claim 9 further comprising a pharmaceutically acceptable carrier.

11. The composition of claim 9 further comprising an adjuvant.

* * * * *